US007943346B2

(12) United States Patent
Bergeron et al.

(10) Patent No.: US 7,943,346 B2
(45) Date of Patent: *May 17, 2011

(54) PROBES AND PRIMERS FOR DETECTION OF BACTERIAL PATHOGENS AND ANTIBIOTIC RESISTANCE GENES

(75) Inventors: Michel G. Bergeron, Sillery (CA); Marc Ouellette, Québec (CA); Paul H. Roy, Loretteville (CA)

(73) Assignee: Geneohm Sciences Canada Inc., Quebec (CA)

(*) Notice: Subject to any disclaimer, the term of this patent is extended or adjusted under 35 U.S.C. 154(b) by 93 days.

This patent is subject to a terminal disclaimer.

(21) Appl. No.: 11/416,499

(22) Filed: May 1, 2006

(65) Prior Publication Data

US 2007/0105129 A1 May 10, 2007

Related U.S. Application Data

(63) Continuation of application No. 10/121,120, filed on Apr. 11, 2002, which is a continuation of application No. 09/452,599, filed on Dec. 1, 1999, now abandoned, which is a continuation of application No. 08/526,840, filed on Sep. 11, 1995, now Pat. No. 6,001,564, which is a continuation-in-part of application No. 08/304,732, filed on Sep. 12, 1994, now abandoned.

(51) Int. Cl.
  *C12P 19/34* (2006.01)
  *C07H 21/04* (2006.01)
(52) U.S. Cl. .................. 435/91.2; 536/24.32; 536/24.33
(58) Field of Classification Search .......................... None
  See application file for complete search history.

(56) References Cited

U.S. PATENT DOCUMENTS

| 4,816,389 A | 3/1989 | Sansonetti et al. |
| 5,030,556 A | 7/1991 | Beaulieu et al. |
| 5,041,372 A | 8/1991 | Lampel et al. |
| 5,084,565 A | 1/1992 | Parodos et al. |
| 5,089,386 A | 2/1992 | Stackebrandt et al. |
| 5,162,199 A | 11/1992 | Stern et al. |
| 5,232,831 A | 8/1993 | Milliman et al. |
| 5,292,874 A | 3/1994 | Milliman |
| 5,298,392 A | 3/1994 | Atlas et al. |
| 5,334,501 A | 8/1994 | Adams et al. |
| 5,389,513 A | 2/1995 | Baquero et al. |
| 5,401,631 A | 3/1995 | Lane et al. |
| 5,437,978 A | 8/1995 | Ubukata et al. |
| 5,472,843 A | 12/1995 | Milliman |
| 5,476,929 A * | 12/1995 | Briles et al. .................. 536/24.32 |
| 5,523,205 A | 6/1996 | Cossart et al. |
| 5,523,217 A * | 6/1996 | Lupski et al. .................. 435/91.2 |
| 5,541,308 A | 7/1996 | Hogan et al. |
| 5,574,145 A | 11/1996 | Barry et al. |
| 5,595,874 A | 1/1997 | Hogan et al. |
| 5,599,665 A | 2/1997 | Barbieri et al. |
| 5,627,275 A | 5/1997 | Roll |
| 5,652,102 A | 7/1997 | Fratamico et al. |
| 5,708,160 A | 1/1998 | Goh et al. |
| 5,866,336 A | 2/1999 | Nazarenko et al. |
| 5,994,066 A | 11/1999 | Bergeron et al. |
| 6,001,564 A | 12/1999 | Bergeron et al. |
| 6,037,130 A | 3/2000 | Tyagi et al. |
| 6,582,908 B2 | 6/2003 | Fodor et al. |
| 6,610,836 B1 | 8/2003 | Breton et al. |
| 2003/0180733 A1 | 9/2003 | Bergeron et al. |
| 2004/0185478 A1 | 9/2004 | Bergeron et al. |
| 2005/0042606 A9 | 2/2005 | Bergeron et al. |
| 2006/0263810 A1 | 11/2006 | Bergeron et al. |
| 2007/0009947 A1 | 1/2007 | Bergeron et al. |
| 2009/0047671 A1 | 2/2009 | Bergeron et al. |
| 2009/0053702 A1 | 2/2009 | Bergeron et al. |
| 2009/0053703 A1 | 2/2009 | Bergeron et al. |
| 2009/0068641 A1 | 3/2009 | Bergeron et al. |
| 2010/0267012 A1 | 10/2010 | Bergeron et al. |

FOREIGN PATENT DOCUMENTS

| CA | 2052822 | 4/1992 |
| EP | 0 133 288 | 2/1985 |
| EP | 0 133 671 | 3/1985 |
| EP | 0 272 009 | 6/1988 |
| EP | 0 277 237 | 8/1988 |
| EP | 0 297 291 | 1/1989 |
| EP | 0 337 896 | 10/1989 |
| EP | 0 364 255 A2 | 10/1989 |

(Continued)

OTHER PUBLICATIONS

GenBank GI:147581 [online] Sep. 14, 1992 [retrieved on Oct. 12, 2008], retrieved from http://www.ncbi.nlm.nih.gov/entrez/viewerfcgi?147581:OLDID:114614 (4 pages).*
Jorda et al. Diagnosis of nosocomial pneumonia in mechanically ventilated patients by the blind protected telescoping catheter. Intensive Care Med 19:377-382 (1993).*
Akaboshi et al., Nucleotide sequence of the recA gene of *Proteus mirabilis*, Nucleic Acids Res. 17(11) (1989) 4390-4390.
Ashimoto et al., Molecular epidemiology of *Staphylococcus* spp. contamination in the ward environment: study on *mecA* and *femA* genes in methicillin-resistant strains, Kasenshogaku Zasshi 69 (1995) 15-20.

(Continued)

*Primary Examiner* — Samuel C Woolwine
(74) *Attorney, Agent, or Firm* — Knobbe, Martens, Olson & Bear LLP

(57) ABSTRACT

The present invention relates to methods for universal bacterial detection, for specific detection of the common bacterial pathogens, and for specific detection of commonly encountered and clinically relevant bacterial antibiotic resistance genes directly from clinical specimens or, alternatively, from a bacterial colony. The core of this invention consists primarily of the DNA sequences from all species-specific genomic DNA fragments selected by hybridization from genomic libraries or, alternatively, selected from data banks as well as any oligonucleotide sequences derived from these sequences which can be used as probes or amplification primers for PCR or any other nucleic acid amplification methods. This invention also includes DNA sequences from the selected clinically relevant antibiotic resistance genes. Diagnostic kits comprising such primers and probes are also provided.

16 Claims, No Drawings

FOREIGN PATENT DOCUMENTS

| | | |
|---|---|---|
| EP | 0 438 115 A2 | 7/1991 |
| EP | 0 466 251 | 1/1992 |
| EP | 0 527 628 | 2/1993 |
| EP | 0 577 523 | 1/1994 |
| EP | 0 630 973 A2 | 12/1994 |
| EP | 0 652 291 | 5/1995 |
| EP | 0 695 803 | 2/1996 |
| EP | 0 761 815 | 3/1997 |
| EP | 0 786 519 | 7/1997 |
| EP | 0 804 616 B1 | 6/2002 |
| FR | 2584419 | 1/1987 |
| FR | 2599743 | 12/1987 |
| FR | 2636075 | 3/1990 |
| FR | 2685334 | 6/1993 |
| FR | 2686604 A1 | 7/1993 |
| FR | 2699539 | 6/1994 |
| JP | 6-54700 | 3/1994 |
| JP | 6-90798 | 4/1994 |
| JP | 6-165681 | 6/1994 |
| JP | 7-67657 | 3/1995 |
| JP | 7-209294 | 8/1995 |
| WO | WO 90/14444 | 11/1990 |
| WO | WO 91/08305 | 6/1991 |
| WO | WO 91/11531 | 8/1991 |
| WO | WO 91/16454 | 10/1991 |
| WO | WO 91/18926 | 12/1991 |
| WO | WO 92/03455 | 3/1992 |
| WO | WO 92/11273 | 7/1992 |
| WO | WO 92/14488 | 9/1992 |
| WO | WO 93/03186 | 2/1993 |
| WO | WO 93/12245 | 6/1993 |
| WO | WO 94/02645 | 2/1994 |
| WO | WO 94/17205 | 8/1994 |
| WO | WO 95/00650 | 1/1995 |
| WO | WO 95/09025 | 4/1995 |
| WO | WO 95/20055 | 7/1995 |
| WO | WO 96/00298 | 1/1996 |
| WO | WO 96/02648 | 2/1996 |
| WO | WO 96/08582 | 3/1996 |
| WO | WO 96/18745 | 6/1996 |
| WO | WO 98/20157 | 5/1998 |
| WO | WO 99/24059 | 5/1999 |
| WO | WO 00/14274 | 3/2000 |
| WO | WO 01/23604 | 4/2001 |
| WO | WO 2004/055205 | 7/2004 |

OTHER PUBLICATIONS

Bej et al., Multiplex PCR amplification and immobilized capture probes for detection of bacterial pathogens and indicators in water, Mol. Cell. Probes, 4 (1990) 353-365.

Bell et al., Outer membrane protein H1 of *Pseudomonas aeruginosa*: purification of the protein and cloning and nucleotide sequence of the gene, J. Bacteriol. 171(6) (1989) 3211-3217.

Black et al., Detection of *Streptococcal pyrogenic* exotoxin genes by a nested polymerase chain reaction, Mol. Cell. Probes, 7 (1993) 255-259.

Chen et al., Transcription and expression of the exotoxin A gene of *Pseudomonas aeruginosa*, Gen. Microbiol. 133 (11) (1987) 3081-3091.

Cleuziat et al., Specific detection of *Escherichia coli* and *Shigella* species using fragments of genes coding for β-glucuronidase, FEMS Microbiol. Letters 72 (1990) 315-322.

Cormican et al., Multiplex PCR for identifying mycobacterial isolates, J. Clin. Pathol., 48 (1995) 203-205.

Dieffenbach et al., General concepts for PCR primer design, Genome Research (1993) 530-537.

Dutka-Malen et al., Detection of glycopeptide resistance genotypes and identification to the species level of clinically relevant *Enterococci* by PCR, J. Clin. Microbiol. 31(1)(1995) 24-27.

Experimental Protocol concerning Enablement of EP-B1 804 616, Mar. 24, 2004.

Figueroa et al., Multiplex polymerase chain reaction based assay for the detection of *Babesia bigemina, Babesia bovis* and *Anaplasma marginale* DNA in bovine blood, Vet. Parasit., 50 (1993) 69-81.

Fischer et al., Mannitol-specific phosphoenolpyruvate-dependent phosphotransferase system of *Enterococcus faecalis*: Molecular cloning and nucleotide sequences of the Enzyme III$^{Mtl}$ gene and the mannitol-1-phosphate dehydrogenase gene, expression in *Escherichia coli*, and comparison of the gene products with similar enzymes, J. Bacteriol. 173(12) (1991) 3709-3715.

Fratamico et al., Detection of *Escherichia coil* O157:H7 by multiplex PCR, J. Clin. Microbiol., 33(8) (1995) 2188-2191.

Friedland et al., Development of a polymerase chain reaction assay to detect the presence of *Streptococcus pneumoniae* DNA, Diagn. Microbiol. Infect. Dis. 20(4) (1994) 187-193.

Gray et al., Cloning, nucleotide sequence, and expression in *Escherichia coil* of the exotoxin A structural gene of *Pseudomonas aeruginosa*, Proc. Natl. Acad. Sci. USA 81(9) (1984) 2645-2649.

Griffin et al., The Design of primers for PCR, PCR Technology (1994) 5-11.

Guay et al., Detection of the pathogenic parasite *Toxoplasma gondii* by specific amplification of ribosomal sequences using comultiplex polymerase chain reaction, J. Clin Microbiol. 31(2) (1993) 203-207.

Gutierrez et al., Point mutations that reduce the expression of *malPQ*, a positively controlled operon of *Escherichia coli*, J. Mol. Biol. 177(1) (1984) 69-86.

Horii et al., Organization of the *recA* gene of *Escherichia coli*, Proc. Natl. Acad. Sci. USA 77(1) (1980) 313-317.

Hotomi et al., Detection of *Haemophilus influenzae* in middle ear of otitis media with effusion by polymerase chain reaction, Int. J. Pediatr. Otorhinolaryngol. 27(2) (1993) 19-26.

Hynes et al., PCR amplification of *Streptococcal* DNA using crude cell lysates, FEMS Microbiol. Lett. 94 (1992) 139-142.

Innis et al., Statistical refinement of primary design parameters, PCR Applications, (1999) 55-71.

Kearns, et al., Rapid detection of methicillin-resistant *Staphylococci* by multiplex PCR, Journal of Hospital Infection, (1999) 43:33-37.

Khan et al., Detection of *Pseudomonas aeruginosa* from clinical and environmental samples by amplification of the Exotoxin A gene using PCR, Appl. Environm. Microbiol. 60(10) (1994) 3739-3745.

Kong et al., Co-detection of three species of water-borne bacteria by multiplex PCR, Marine Pollution Bulletin, 31 (4-12) (1995) 317-324.

Lawrence et al., Molecular and evolutionary relationships among enteric bacteria, J. Gen. Microbiol. 137(8) (1991) 1911-1921.

Le Bouguenec et al., Rapid and specific detection of the *pap, afa,* and *sfa* adhesin-encoding operons in uropathogenic *Escherichia coli* strains by polymerase chain reaction, J. Clin. Microbiol. 30(5) (1992) 1189-1193.

Li et al., Identification of *Bordetella pertussis* infection by shared-primer PCR, J. Clin. Microbiol., 32(3) (1994) 783-789.

Lowe et al., Nucleotide sequence of the aliphatic amidase regulator gene (*amiR*) of *Pseudomonas aeruginosa*, FEBS Lett. 246 (1-2) (1989) 39-43.

McMillin et al., Simultaneous detection of toxin A and toxin B genetic determinants of *Clostridium difficile* using the multiplex polymerase chain reaction, Can. J. Microbiol., 38 (1992) 81-83.

Palm et al., Evolution of catalytic and regulatory sites in phosphorylases, Nature 313(6002) (1985) 500-502.

Post et al., Molecular analysis of bacterial pathogens in otitis media with effusion, JAMA 273(20) (1995) 1598-1604.

Pritchard et al, Possible insertion sequences in a mosaic genome organization upstream of the exotoxin A gene in *Pseudomonas aeruginosa*, J. Bacteriol. 172(4) (1990) 2020-2028.

Radstrom et al., Detection of bacterial DNA in cerebrospinal fluid by an assay for simultaneous detection of *Neisseria meningitidis, Haemophilus influenzae*, and *Streptococci* using a seminested PCR strategy, J. Clin. Microbiol. 32(11) (1994) 2738-2744.

Silvestrini et al., Nitrite reductase from *Pseudomonas aeruginosa*: sequence of the gene and the protein, FEBS Lett. 254(1-2) (1989) 33-38.

Su et al., Nucleotide sequence of the gelatinase gene (*gelE*) from *Enterococcus faecalis* subsp. *liquefaciens*, Infect. Immun. 59(1) (1991) 415-420.

Tyler et al., *Streptococcal erythrogenic* toxin genes: detection by polymerase chain reaction and association with disease in strains isolated in Canada from 1940 to 1991, J. Clin. Microbiol. 30(12) (1992) 3127-3131.

Ubukata et al., Rapid detection of the *mecA* gene in methicillin-resistant *Staphylococci* by enzymatic detection of polymerase chain reaction products, J. Clin. Microbiol. 30(7) (1992) 1728-1733.

Ueyama et al., High incidence of *Haemophilus influenzae* in nasopharyngeal secretions and middle ear effusions as detected by PCR, J. Clin. Microbiol. 33(7) (1995) 1835-1838.

Ünal, et al., Detection of Methicillin-Resistant *Staphylococci* by Using the Polymerase Chain Reaction, Journal of Clinical Microbiology, (1992) 1685-1691.

van Ketel, Detection of *Haemophilus influenzae* in cerebrospinal fluids by polymerase chain reaction DNA amplification, J. Med. Microbiol., 33 (1990) 271-276.

Vannuffel, et al., Specific Detection of Methicillin-Resistant *Staphylococcus* Species by Multiplex PCR, Journal of Clinical Microbiology, (1995) 2864-2867.

Weickmann and Weickmann, Reference D34, European Opposition for EP 0804616Spezifität der Primer, ANNEX II: Specific and ubiquitous primers for DNA amplification, 11 pages, Sep. 13, 2007.

Weickmann and Weickmann, Reference D35, European Opposition for EP 0804616, Vergleich: Bacterial species: *Escherichia coli*, Sep. 13, 2007.

Weickmann and Weickmann, Reference D40, European Opposition for EP 0804616, Comparison of Sequences TRP.OO3 and TRP.004 of WO 93/12245 with SEQ ID No. 5 of EP 804616, Sep. 13, 2007.

Weickmann and Weickmann, Reference D43, European Opposition for EP 0804616Com parison of Sequence *E. coli* malPQ operon, 5'-end of Gutierrez et al., J. Mol. Biol. 177(1) (1984) 69-86 with SEQ ID No. 6 (glycogen phosphorylase) of EP 804616; of Sequence *E.coli* recA gene, 5'-region of Zhao et al., Mol.Gen.Genet. 222(2-3) (1990) 369-376 with SEQ ID No. 7 of EP 804616, and of exotoxin A gene of Chen et al., J. Gen. Microbiol. 133(11) (1987) 3081-3091 with SEQ ID No. 18 of EP 804616, Sep. 13, 2007.

Weickmann and Weickmann, Reference D49, European Opposition for EP 0804616, Vergleich der SEQ ID No. 26 (*Haemophilus influenzae* omp P1 gene) aus EP804616 und Sonde 106b aus EP804616 mit Primer Homp1 und Homp3 aus Cote S. Et al., Mol. Cell. Probes (Feb. 1994) 8:23-37, Sep. 13, 2007.

Weickmann and Weickmann, Reference D50, European Opposition for EP 0804616, Vergleich der SEQ ID No. 27 (*Haemophilus influenzae*transformation gene cluster) und Primer 154 bzw 155b und Sonde 107b aus EP804616 mit Primer Htra3 aus Cote S. Et al., Mol. Cell. Probes (Feb. 1994) 8:23-37, Sep. 13, 2007.

Weickmann and Weickmann, Reference D52, European Opposition for EP 0804616, Comparison of SEQ ID No. 8 to 21 of EP577523 with neuraminidase nanA of *Streptococcus pneumoniae* (cf. SEQ ID No. 35 of EP804616), Sep. 13, 2007.

Weickmann and Weickmann, Reference D54, European Opposition for EP 0804616, Comparison of SEQ ID No. 1 and Primers YR2 and YR6 of FR2686604 with primers SEQ ID No. 141 and 142 of EP804616, Sep. 13, 2007.

Weickmann and Weickmann, Reference D56, European Opposition for EP 0804616, Vergleich der SEQ ID No. 33 (*Streptococcus pyogenes* Exotoxin A gene) aus EP804616 und Primern SEQ ID Nos. 143 bzw. 144b (EP804616) mit speA-Primern P1-P4 aus Black C.M. et al., Mol. Cell. Probes (1993) 7: 255-259 und speA-primern SPEA-1, SPEA-2 aus Tyler S.D. et al., J.Clin.Microbiol.Dis. (1992) 30:3127-3131, Sep. 13, 2007.

Weickmann and Weickmann, Reference, D58, European Opposition for EP 0804616, References for target genes, Sep. 13, 2007.

Weickmann and Weickmann, Reference D72, European Opposition for EP 0804616Vergleich der SEQ ID Nos. 18 und 20 (*Pseudomonas aeruginosa*) aus EP804616 und der entsprechenden Probesequenzen SEQ ID Nos. 87-90 und 94 +95 mit Primer und Probesequenzen ETA1-ETA7 aus Khan et al., Appl. Environment. Microbiol. Oct. 1994, Sep. 13, 2007.

Yanofsky et al., The complete nucleotide sequence of the tryptophan operon of *Escherichia coli*. Nucleic Acids Res. 9(24) (1981) 6647-6668.

Zakrewska-Czerwinska et al., Identification of *Staphylococcus epidermidis* using a 16S rRNA-directed oligonucleotide probe, FEMS Microbiol. Lett.100 (1992) 51-58.

Zambardi et al., Laboratory Diagnosis of Oxacillin resistance in *Staphylococcus aureus* by a multiplex-polymerase chain reaction assay, Diagn. Microbiol. Infect. Dis. 19 (1994) 25-31.

Zhao et al., DNA sequence analysis of the *recA* genes from *Proteus vulgaris, Erwinia carotovora, Shigella flexneri* and *Escherichia coli* B/r, Mol.Gen.Genet. 222(2-3) (1990) 369-376.

Abe et al. (Jul. 1992), A sensitive method for the detection of enterotoxigenic *Escherichia coil* by the polymerase chain reaction using multiple primer pairs, Zentralbl Bakteriol 277(2):170-8.

Brakstad et al. (Jul. 1992), Detection of *Staphylococcus aureus* by polymerase chain reaction amplification of the *nuc* gene, J Clin Microbiol. 30(7):1654-60.

Brakstad et al. (Sep. 1993), Multiplex polymerase chain reaction for detection of genes for *Staphylococcus aureus* thermonuclease and methicillin resistance and correlation with oxacillin resistance, APMIS 101(9):681-688.

Brakstad et al. (1993), Comparison of various methods and reagents for species identification of *Staphylococcus aureus* positive or negative for the *mecA* gene, APMIS 101:651-654.

Brakstad et al. (1995), Direct identification of *Staphylococcus aureus* in blood cultures by detection of the gene encoding the thermostable nuclease or the gene product, APMIS 103:209-218.

Buck et al. (1999), Design strategies and performance of custom DNA sequencing primers, Biotechniques 27(3):528-536.

Cote et al. (1994), Molecular typing of *Haemophilus influenzae* using a DNA probe and multiplex PCR, Mol. Cell. Probes 8:23-37.

Deneer, H.G. et al. (1991), Species-specific detection of *Listeria monocytogenes* by DNA amplification, Appl. Environ. Microbiol. 57(2):606-609.

Dopazo et al. (1993), A computer program for the design of PCR primers for diagnosis of highly variable genomes, J. Virol. Meth. 41:157-165.

Dutilh, B. et al. (1989), Specific amplification of a DNA sequence common to all *Chlamydia Trachomatis* Serovars using the polymerase chain reaction, Res. Microbiol. 140:7-16.

Edwards et al. (1994), Multiplex PCR: advantages, development, and applications, PCR Meth. Appl. 3:S65-S75.

Geha et al. (Jul. 1994), Multiplex PCR for identification of methicillin-resistant *Staphylococci* in the clinical laboratory, J Clin Microbiol. 32(7):1768-72.

Gillespie et al. (May 1994), Detection of *Streptococcus pneumoniae* in sputum samples by PCR, J Clin Microbiol. 32(5):1308-11.

Houard et al. (1989), Specific identification of *Bordetella pertussis* by the polymerase chain reaction, Res. Microbiol. 140:477-487.

Kaper, J.B. et al. (1999), Pathogenicity islands and other mobile genetic elements of Diarrheagenic *Escherichia coli*, American Society for Microbiol., Chap. 3:33-58.

Malloy, D.C. et al. (1990), Detection of *Borrelia burgdorferi* using polymerase chain reaction, J. Clin. Microbiol. 28(6)1089-1093.

McIntosh et al. (Aug. 1992), Detection of *Pseudomonas aeruginosa* in sputum from cystic fibrosis patients by the polymerase chain reaction, Mol Cell Probes 6(4):299-304.

O'Callaghan et al. (1994), Development of a PCR probe test for identifying *Pseudomonas aeruginosa* and *Pseudomonas (Burkholderia) cepacia*, J. Clin. Pathol. 47:222-226.

Pollard, D.R. et al. (1989), A polymerase chain reaction (PCR) protocol for the specific detection of *Chlamydia* spp, Mol. Cell. Probes 3:383-389.

Priebe et al. (1988), Nucleotide sequence of the hexA gene for DNA mismatch repair in *Streptococcus pneumoniae* and homology of hexA to mutS of *Escherichia coli* and *Salmonella typhimurium*, J. Bacteriol. 170:190-196.

Rosa, P.A. et al. (1989), A specific and sensitive assay for the Lyme Disease Spirochete *Borrelia burgdorferi* using the polymerase chain reaction, J. Infect. Dis. 160(6)1018-1029.

Rosa, P.A., et al. (1991), Polymerase chain reaction analyses identify two distinct classes of *Borrelia burgdorferi*, J. Clin. Microbiol. 29(3):524-532.

Ryffel C. et al. (Sep. 28, 1990), Sequence comparison of mecA genes isolated from methicillin-resistant *Staphylococcus aureus* and *Staphylococcus epidermidis*, Gene 94(1):137-8.

Schaechter, M. et al. (1989), Mechanisms of Microbial Disease. The Enteric Bacteria: Diarrhea and Dysentery, Dept. of Microbiol. and Immunol., Chap. 17:256-265.

Spierings et al. (1992), Characterization of the *Citrobacter freundii* phoE gene and development of *C. freundii*-specific oligonucleotides, FEMS Microbiol. Letters 99:199-204.

Stacy-Phipps et al. (May 1995), Multiplex PCR assay and simple preparation method for stool specimens detect enterotoxigenic *Escherichia coil* DNA during course of infection, J Clin Microbiol. 33(5):1054-59.

Wang, R.F. et al. (Apr. 1994), A 16S rDNA-based PCR method for rapid and specific detection of *Clostridium perfringens* in food, Mol. Cell. Probes 8(2):131-138.

Way et al. (1993), Specific detection of *Salmonella* spp. by multiplex polymerase chain reaction, App. Environ. Microbiol. 59:1473-1479.

White, T.J. et al. (1992), The polymerase chain reaction; clinical applications, Advances in Clinical Chemistry 29:161-196.

Wilson, I.G. et al. (1991), Detection of Enterotoxigenic *Staphylococcus aureus* in dried skimmed milk: Use of the polymerase chain reaction for amplification and detection of *Staphylococcal* Enterotoxin Genes *entB* and *entCl* and the Thermonuclease Gene *nuc*, Applied and Environmental Microbiology, 1793-1798.

Wittwer et al. (1991), Rapid cycle DNA amplification: time and temperature optimization, Biotechniques 10(1):76-83.

Murakami, et al. Identification of methicillin-resistant strains of *Staphylococci* by polymerase chain reaction. Journal of clinical Microbiology. 29(10): 2240-2244 (1991).

Abdulkarim et al., Homologous Recombination between the *tuf* Genes of *Salmonella typhimurium*, J Mol Bio.(1996) 260: 506-522.

Altschul et al., Basic Local Alignment Search Tool, J Mol Biol. (1990) 215: 403-410.

Amann et al., β-Subunit of ATP-Synthase: A Useful Marker for Studying the Phylogenetic Relationship of Eubacteria J Gen Microbiol. (1988) 134: 2815-2821.

Aminov et al., Cloning, Sequencing and Complementation Analysis of the *recA* Gene from *Prevotella ruminicola*, FEMS Microbiol Lett. (1996) 144(1): 53-59.

An et al., The Nucleotide Sequence of *tufB* and four nearby *tRNA* Structural Genes of *Escherichia coli*, Gene, (1980) 12(1-2): 33-39.

Anborgh et al., New Antibiotic that Acts Specifically on the GTP-Bound Form of Elgonation Factor Tu, EMBO J. (1991) 10(4): 779-784.

Andersson et al., Unusual Organization of the rRNA Genes in *Rickettsia prowazekii*, J Bacteriol. (1995) 177(14): 4171-4175. (See Harrison et al Eds).

Bäckman et al., Evaluation of an Extended Diagnostic PCR Assay for Detection and Verification of the Common Causes of Bacterial Meningitis in CSF and other Biological Samples, Mol Cell Probes (1999) 13: 49-60.

Balows et al., Eds. The Prokaryotes: A Handbook on the Biology of Bacteria: Ecophysiology, Isolation, Identification, Applications, 2nd Ed., Brenner, Introduction to the Family Enterobacteriaceae, Springer Verlag (1992) Chapter 141, pp. 2673-2695.

Balows et al., Eds. The Prokaryotes: A Handbook on the Biology of Bacteria: Ecophysiology, Isolation, Identification, Applications, 2nd Ed., Brenner, Additional Genera of Enterobacteriaceae, Springer Verlag (1992) Chapter 155, pp. 2922-2937.

Belay et al., Methanogenic Bacteria from Human Dental Plaque, App Environ Microbiol.(1988) 54(2): 600-603.

Belay et al., Methanogenic Bacteria in Human Vaginal Samples, J Clin Microbiol.(1990) 28(7): 1666-1668.

Bentley et al., Development of PCR-based Hybridization Protocol for Identification of *Streptococcal* Species, J Clin Microbiol. (1995) 33(5): 1296-1301.

Bercovier et al., Intra and Interspecies Relatedness of *Yersinia pestis* by DNA Hybridization and its Relationship to *Yersinia pseudotuberculosis*, Curr Microbiol. (1980) 4: 225-229.

Berg et al, Development of an Amplication and Hybridization Assay for the Specific and Sensitive Detection of *Mycoplasma fermantans* DNA. Mol Cell Probes, (1996) 10: 7-14.

Bergeron et al., Diagnosing Bacterial Infectious Diseases in One hour: An Essential Upcoming Revolution Infection (1995) 23(2): 69-72.

Bergeron et al., Preventing Antibiotic Resistance through Rapid Genotypic Identification of Bacteria and of Their Antibiotic Resistance Genes in the Clinical Microbiology Laboratory, J Clin Microbiol. (1998) 36(8): 2169-2172.

Berkenkamp et al, Infrared MALDI Mass Spectrometry of Large Nucleic Acids, Science (1998) 281: 260-262; American Association for the Advancement of science.

Birnboim, et al, A rapid alkaline extraction procedure for screening recombinant plasmid DNA, Nucleic Acids Res. (1979) 7(6): 1513-1523. (1979).

Bremaud et al Genetic and molecular analysis of the tRNA-tufB operon of the myxobacterium *Stigmatella aurantiaca*, Nucleic Acids Res. (1995)23(10): 1737-1743.

Brenner et al., Polynucleotide sequence relatedness among three groups of pathogenic *Escherichia coli* strains, Infect Immun. (1972) 6(3): 308-315.

Brenner et al., Polynucleotide sequence divergence among strains of *Escherichia coli* and closely related organisms, J Bacter. (1972) 109(3): 953-965.

Brenner et al., *Enterobacter gergoviae* sp nov.: a new species of *Enterobacteriaceae* found in clinical specimens and the environment, Int J Syst Bacter. (1980) 30(1): 1-6.

Brenner et al., *Escherichia vulneris*: a New Species of *Enterobacteriaceae* associated with human wounds, J Clin Microbiol. (1982) 15(6): 1133-1140.

Brenner et al., Attempts to classify herbicola group-*Enterobacter agglomerans* strains by deoxyribonucleic acid hybridization and phenotypic tests, Int J Sys Bacter. (1984) 34(1): 45-55.

Brenner et al., *Enterobacter asburiae* sp nov., a new species found in clinical specimens, and reassignment of *evinia dissolvens* and *ervinia nimipressuralis* to the genus *Enterobacter* as *Enterobacter dissolvens* comb nov and *Enterobacter nimipressuralis* comb nov., J Clin Microbiol. (1986) 23(6): 1114-1120.

Brenner et al., Classification of citrobacteria by DNA hybridization: Designation of *Citrobacter farmeri* sp nov., *Citrobacter youngae* sp nov., *Citrobacter braakii* sp nov., *Citrrobacter werkmanii* sp nove., *Citrobacter sedlakii* sp nove., and three unnambed *citrobacter* genomospecies, *Int J System Bacter*. (1993) 43(4): 645-658.

Brenner et al., Encoded combinatorial chemistry, Proc Natl Acad Sci. USA (1992) 89: 5381-5383.

Brenner et al., Biochemical identification of *Citrobacter* species defined by DNA hybridization and description of *Citrobacter gillenii* sp nov., J Clin Microbio. (1999) 37(8): 2619-2624.

Brisson-Noël et al. Evidence for natural gene transfer from gram-positive cocci to *Escherichia coli*, J Bacteriol. (1988) 170(4): 1739-1745.

Caldas et al., Chaperone properties of bacterial elongation factor EF-Tu, J Biol Chem. (1998) 273(19): 11478-11482.

Carlin et al., Monoclonal antibodies specific for elongation factor Tu and complete nucleotide sequence of the *tuf* gene in *Mycobacterium tuberculosis*, Infect Immun. (1992) 60(8): 3136-3142.

Chamberland et al., Antibiotic susceptibility profiles of 941 gram-negative bacteria isolated from Septicemi patients throught Canada: The Canadian Study Group, Clin Infect Dis. (1992) 15(4): 615-628.

Chen et al., Broad range DNA probes for detecting and amplifying eubacterial nucleic acids, FEMS Micro Lett. (1989) 57: 19-24.

Chiu et al., Mass spectrometry of nucleic acids, Clin Chem. (1999) 45: 1578-1579.

Christensen et al., Phylogenetic relationships of *Salmonella* based on DNA sequence comparison of atpD encoding the β subunit of ATP synthase, FEMS Micro Lett. (1998) 161: 89-96.

Cilia et al., Sequence heterogeneities among 16S Ribosomal RNA sequences, and their effect on phylogenetic analyses at the species level, Clin Chem. ((1999) 45: 451-461.

Clayton et al., Intraspecific variation in small-subunit rRNA sequences in GenBank: Why single sequences may not adequately represent prokaryotic taxa, Int J System Bacteriol. (1995) 45(3): 595-599.

Cousineau et al., On the Origin of Protein Synthesis Factors: A Gene Duplication/Fusion Model, J Mol Evol (1997) 45: 661-670.

Croizé, , Les Méthodes Automatisées d'Identification des Bactéries a l'Aube de 1995, La Lettre de L'Infectiologu (1995) 10(4): 109-113. (French Language w/ Engl Abstract).

Dickey et al., Emended description of *Enterobacter cancerogenus* comb nov. Int J System Bacteriol. (1988) 38(4): 371-374.
Dieffenbach et al. Eds. PCR Primer: A laboratory manual, Cha et al., Specificity, efficiency, and fidelity of PCR, Cold Spring Harbor Laboratory Press (1995) pp. 37-62.
Dieffenbach et al. Eds. PCR Primer: A laboratory manual, Kwok et al., Design and use of mismatched and degenerate primers, Cold Spring Harbor Laboratory Press (1995) pp. 143-155.
Drmanac et al., DNA Sequence Determination by Hybridization: A strategy for efficient large-scale sequencing, Science (1993) 260: 1649-1652.
Dutka-Malen et al., Sequence of the vanC gene of *Enterococcus gallinarum* BM 4174 encoding a D-alanin:D-alanine ligase-related protein necessary for vancomycin resistance, Gene (1992) 112: 53-58.
East et al., Cloning and Sequence Determination of six *Staphylococcus aureus* betalactamasses and their expression in *Escherichia coli* and *Staphylococcus aureus*, J Gen Microbiol. (1989) 135(4): 1001-15.
Egholm et al., PNA hybridizes to complementary oligonucleotides obeying the Watson-Crick hydrogen-bonding rules, Nature (1993) 365(10): 566-568.
Ehrlich et al., Eds. PCR-Based Diagnosis in Infectious Disease, Chapters 1, 3, Blackwell Scientific Publications (1994), pp. 3-18 and 45-55.
Emori et al., An Overview of Nosocomial Infections, Including the Role of Microbiology Laboratory. Clin Microbiol Rev. (1993) 6(4): 428-442.
Evers et al., Sequence of the *vanB* and *ddl* Genes Encoding D-alanine:D-lactate and D-alanine:D-alanine Ligases in Vancomycin-resistant *Enterococcus faecalis* V583. Gene. (1994) 140(1): 97-102.
Eykyn et al., The Causative Organisms of Septicaemia and Their Epidemiology. J Antimicrob Chemother. (1990) 25 Suppl C: 41-58.
Fani et al., Use of Random amplified polymorphic DNA (RAPD) for generating specific DNA probes for microorganisms, Mol Ecol. (1993) 2:243-250.
Farmer III et al., *Enterobacter sakazakii*: A new species of "*Enterobacteriaceae*" isolated from clinical specimens, Int J System Bacter. (1980) 30(3): 569-584.
Farmer III et al., Biochemical identification of new species and biogroups of *Enterobacteriaceae* isolated from clinical specimens, J Clin Microbiol. (1985) 21(1): 46-76.
Farmer III et al., *Escherichia fergusonii* and *Enterobacter taylorae*, two new species of *Enterobacteriaceae* isolated from clinical specimens, J Clin Microbiol. (1985) 21(1): 77-81.
Farmer III, Proposed Rewording of Rule 10C of the Bacteriological Code, Int J Syst Bacter. (1985) 35(2): 222.
Filer et al., Duplication of the *tuf*Gene, which encodes peptide chain elongation factor Tu, is widespread in gram-negative bacteria, J Bacter. (1981) 148(3): 1006-1011.
Fischer et al., Predicting structures for genome proteins, Curr Opin Struct Biol. (1999) 9: 2008-211.
Fleischmann et al., Whole-genome Random Sequencing and Assembly of *Haemophilus influenzae* Rd. Science (1995) 269(5223): 496-512.
Flores et al., Recovery of DNA from Agarose Gels Stained with Methylene Blue. Biotechniques. (1992) 13(2): 203-205.
Fox et al., How Close is Close: 16S rRNA sequence identity may not be sufficient to guarantee species identity, Int J Syst Bacter. (1992) 42(1): 166-170.
Gannon et al., Rapid and Sensitive Method for Detection of Shiga-like Toxin-producing *Escherichia coli* in Ground Beef Using the Polymerase Chain Reaction, Appl Env Microbiol. (1992) 58(12): 3809-3815.
Gavini et al., Transfer of *Enterobacter agglomerans* (Beijerinck 1999) Ewing and Fife 1972 to *Pantoea* gen. nov. as *Pantoea agglomerans* comb. Nov. and description of *Pantoea dispersa* sp nov., Int J System Bacteriol. (1989) 39(3): 337-345.
Gogarten et al., Evolution of the vacuolar $H^+$-ATPase: Implications for the origin off eukaryotes, Proc Natl Acad Sci. USA, 86: 6661-6665.

Greer, Comparative modeling of homologous proteins, Methods in Enzymology, (1991) 202: 239-252.
Greisen et al., PCR Primers and Probes for the 16S rRNA Gene of Most Species of Pathogenic Bacteria, Including Bacteria Found in Cerebospinal Fluid, J Clin Microbiol. (1994) 32(2): 335-351.
Guex et al., Protein modelling for all (Swiss-Model), TIBS 24 Computer Corner (1999) pp. 364-367.
Gupta et al., Protein phylogenies and signature sequences: a reappraisal of evolutionary relationships among *Archaebacteria*, *Eubacteria*, and *Eukaryotes*, Micro Mol Bio Rev. (1998) 62(4): 1435-1491.
Harrison et al., Eds Micro Total Analysis Systems '98, Anderson et al., Advances in Integrated Genetic Analysis, Proceedings of the uTAS '98 Workshop, Banff, Canada Oct. 13-16, 1998; Kluwer Academic Publishers, Dordrecht, The Netherlands (1998) pp. 11-16, Heller et al., An integrated microelectronic hybridization system for genomic research and diagnostic applications, pp. 221-224.
Hartl et al., The Population Genetics of *Escherichia Coli*, Ann Rev Genet. (1984) 18: 31-68.
Hedegaard et al., Identification of *Enterobacteriaceae* by partial sequencing of the gene encoding translation initiation factor 2, Int J System Bacter. (1999) 49: 1531-1538.
Hill et al., Inversions between ribosomal RNA genes of *Escherichia coli*, Proc Natl Acad Sci. USA (1981) 78(11): 7069-7072.
Ibrahim et al., The phylogeny of the genus *Yersinia* based on 16S rDNA sequences, FEMS Micro Lett. (1993) 114: 173-178.
Iwabe et al., Evolutionary relationship of archaebacteria, eubacteria, and eukaryotes inferred from phylogenetic trees of duplicated genes, Proc Natl Acad Sci. USA (1989) 86: 9355-9359.
Izard et al., Deoxyribonucleic acid relatedness between *Enterobacter cloacae* and *Enterobacter amnigenus* sp nov., Int J System Bacter. (1981) 31(1): 35-42.
Janda et al., Prototypal diarrheagenic strains of *Hafnia alvei* are actually members of the genus *Escherichia*, J Clin Microbiol. (1999) 37(8): 2399-2401.
Johnson, et al. Urinary Tract Infections in Women: Diagnosis and Treatment, Ann Intern Med. (1989) 111: 906-917.
Kamla, (1994) Database EMPRO EMBL AC: z34275.
Kaufhold et al., Identical Genes Confer High-Level Resistance to Gentamicin upon *Enterococcus faecalis, enterococcus faecium*, and *Streptococcus agalactiae*, Antimicrob Agents Chemother. (1992) 36(6): 1215-1218.
Kellogg et al., TaqStart Antibody: "hot start" PCR Facilitated by a Neutralizing Monoclonal Antibody Directed Against Taq DNA Polymerase. Biotechniques (1994) 16(6): 1134-1137.
Kimura, A simple method for estimating evolutionary rates of base substitutions through comparative studies of nucleotide sequences, J Mol Evol (1980) 16: 111-120.
Kitch et al., Evaluation of RApID onE system for identification of 379 strains in the family *Enterobacteriaceae* and oxidase negative, gram-negative nonfermenters, J Clin Microbiol. (1994) 32(4): 931-934.
Kloos et al., Siplified scheme for routine identification of human *Staphylococcus* species, J Clin Microbiol. (1975) 1(1): 82-88.
König, et al. Analyses of the Flash Track DNA Probe and UTIscreen Bioluminescence Tests for Bacteriuria, J Clin Microbiol. (1992) 30(2): 342-345.
Koshkin et al., LNA (Locked Nucleic Acids): Synthesis of the Adenine, Cytosine, Guanine, 5-Methylcytosine, Thymine and Uracil bicyclonucleoside monomers, oligomerisation, and unprecedented nucleic acid recognition, Tetrahedron (1998) 54: 3607-3630.
Kwok et al., Avoiding False Positive with PCR, Nature (1989) 339: 237-238.
Lee et al., Eds Nucleic Acid Amplification Technologies: Application to Disease Diagnosis, Chapter 5 by Carrino et al. Ligation-based nucleic acid probe methods, Biotechniques Boods, Div. Eaton Publishing (1997), pp. 61-78.
Lee et al., Eds Nucleic Acid Amplification Technologies: Application to Disease Diagnosis, Chapter 6 by Martin et al. PCR and its modifications for the detection of infectious diseases, Biotechniques Boods, Div. Eaton Publishing (1997), pp. 79-99.
Lee et al., Eds Nucleic Acid Amplification Technologies: Application to Disease Diagnosis, Chapter 7 by Olive et al. Qβ replicase assays for the clinical detection of infectious agents, Biotechniques Boods, Div. Eaton Publishing (1997), pp. 101-112.

Lee et al., Eds Nucleic Acid Amplification Technologies: Application to Disease Diagnosis, Chapter 8 by McDonough et al. Application of transcription-medicated amplification . . . , Biotechniques Boods, Div. Eaton Publishing (1997), pp. 113-122.

Lewin, Benjamin, Genes IV, Chapter 3: Genes are mutable units; Oxford University Press (1990) pp. 41-56.

Lewin, Benjamin, Genes IV, Oxford University Press (1990) pp. 497-517.

Livak et al., Oligonucleotides with fluorescent dyes at opposite ends provide a quenched probe system useful for detecting PCR product and nuclei acid hybridization, PCR Methods & Applications, (1995) Cold Spring Harbor Laboratory Press, 4: 357-362.

Loechel et al., Nucleotide Sequence of the *tuf* Gene from *Mycoplasma genitalium*, Nucleic Acids Res. (1989) 17(23): 10127.

Ludwig et al., Database EMPRO. EMPBL, AC:X76863, X76866, X76867, X76871, X76872.

Ludwig et al., Complete nucleotide sequences of seven eubacterial genes coding for the elongation factor Tu: functional, structural and phylogenetic evaluations, Arch Microbiol. (1990) 153: 241-247.

Ludwig et al., Phylogenetic relationships of *Bacteria* based on comparative sequence analysis of elongation factor Tu and ATP-synthase β-subunit genes, Antonie von Leeuwenhoek (1993) 64: 285-305.

Lüneberg et al., Detection of *Mycoplasma pneumoniae* by Polymerase Chain Reaction and Nonradioactive Hybridization in Microtiter Plates, J Clin Microbiol. (1993) 31(5): 1088-1094.

McCabe et al., Bacterial species identification after DNA amplification with a universal primer pair, Mol Gen Metabol. (1999) 66: 205-211.

Miller et al., General microbiology of *recA*: Environmental and evolutionary significance, Ann Rev Microbiol. (1990) 44: 365-394.

Mollet et al., *rpoB* sequence analysis as a novel basis for bacterial identification, Mol Microbiol. (1997) 26(5): 1005-1011.

Monod et al., Sequence and Properties of pIM13: A Macrolide-lincosamide-streptogramin B resistance Plasmid from *Bacillus subtilis*, J Bacteriol. (1986) 167(1): 138-147.

Murphy et al., (1986) Database EMPRO. EMBL. AC:X03216.

Murray et al., Eds. Manual of Clinical Microbiology; Tang et al., Molecular detection and identification of microorganisms, ASM Press, 7th Ed, (1999) Chapter 13, pp. 215-244.

Neidhardt et al., Eds. *Escherichia coli* and *Salmonella* Cellular and Molecular Biology, 2nd Ed., Grunberg-Manago, Regulation of the expression of aminoacyl-tRNA Synthetases and translation Factors, ASM Press, 2nd Ed. (1996) vol. 1, Chapt. 91: 1432-1457.

Neidhardt et al., Eds. *Escherichia coli* and *Salmonella* Cellular and Molecular Biology, Selander et al., Evolutionary Genetics of *Salmonella enterica*, ASM Press (1996) 2nd Ed., Chapt 147: 2691-2707.

Nelson et al., The Evolution of H$^+$-ATPases, TIBS (1989) 14: 113-116.

Nichols et al., A universal nucleoside for use of ambiguous sites in DNA primers, Letters to Nature (1994) 369: 492-493.

Nikiforov et al., The use of 96-well Polystyrene plates for DNA hybridization-based assays: An evaluation ot different approaches ot oligonucleotide immobilization, Anal. Biochem. (1995) 227: 201-209.

Ohama et al., Organization and Codon Usage of the Streptomycin Operon in *Micrococcus luteus*, a Bacterium with a High Genomic G+C Content, J Bacteriol. (1987) 169(10): 4770-4777.

Olcén et al., Rapid Diagnosis of Bacterial Meningitis by a Seminested PCR Strategy, Scand J Infect Dis. (1995) 27(5): 537-539.

Ouellette et al., Precise Insertion of Antibiotic Resistance Determinants into Tn*21*like Transposons: Nucleotide Sequence of the OXA-1 β-lactamase Gene, Proc Natl Acad Sci. USA (1987) 84: 7378-7383.

Perlee, et al. (1993) Database EMPRO EMBL, Translation elongation factor EF-Tu of *Borrelia burgdorferi*—CA:L23125.

Persing et al., Eds. Diagnostic Molecular Microbiology: Principles and Applications, Nucleic Acid Probes for Detection and Identification of Infectious Agents by Tenover, et al., American Society for Microbiology (1993) pp. 3-25.

Persing et al., Eds. Suppl to Diagnostic Molecular Microbiology: Principles and Applications, Genotypic Methods for microbial identification by Reiman et al., American Society for Microbiology (1996) pp. 3-31.

Pezzlo, Detection of Urinary Tract Infections by Rapid Methods, Clin Microbiol Rev. (1988) 1(2): 268-280.

Pezzlo et al., Detection of Bacteriuria and Pyuria by Urinscreen, A Rapid Enzymatic Screening Test, J Clin Microbiol. (1992) 30(3): 680-684.

Podbielski, *Streptococcus agalactiae* Camp Gene. Submitted to Genbank database on Mar. 22, 1993, Accession No. 72754.

Podzorski et al., Molecular Detection and Identification of Microorganisms in Manual of Clinical Microbiology, (1995) ASM Press, pp. 130-157.

Porcella et al., Identification of an EF-Tu Protein that is Periplasm-associated and Processed in *Neisseria gonorrhoeae*, Miocrobiology (1996) 142: 2481-2489.

Reeve, Archaebacteria then . . . archaes now (Are there really no archaeal pathogens? J Bacter. (1999) 181(12): 3613-3617.

Rudolph et al., Evaluation of Polymerase Chain Reaction for Diagnosis of Pneumococcal Pneumonia, J Clin Microbiol. (1993) 31(10): 2661-2666.

Šali, Modelling mutations and homologous proteins, Curr Opin Biotech. (1995) 6: 437-451.

Sambrook et al., Eds. Molecular Cloning: A Laboratory Manual, 2nd Ed. Cold Spring Harbor Laboratory Press, (1989) pp. 1.21-1.52, 9.31-9.62, 10.1-10.70, and 11.1-11.61.

Sambrook et al., Eds. Molecular Cloning: A Laboratory Manual, 2nd Ed. Cold Spring Harbor Laboratory Press, (1989) pp. pp. 18.35-18.39.

Sánchez et al., Advances in comparative protein-structure modelling, Curr Opin Struct Biol. (1997) 7: 206-214.

Sanger et al., DNA Sequencing with Chain-Terminating Inhibitors, P.N.A.S. (1977) 74(12):5463-5467.

Saraste et al., The atp operon: nucleotide sequence of the genes for the α, β, and ϵ subunits of *Escherichia coli* ATP synthase, Nucl Acids Res. (1981) 9(20): 5287-5296.

Sela et al., Duplication of the *tuf* Gene: a new insight into the Phylogeny of Eubacteria, J Bacteriol. (1989) 171(1): 581-584.

Sharma et al., Identification of *Yersinia* species by the API 20E, J Clin Microbio. (1990) 28(6): 1443-1444.

Shaw et al., Isolation, Characterization, and DNA Sequence Analysis of an ACC(6')-II Gene from *Pseudomonas aeruginosa*, Antimicro Agents Chimo. 33(12): 2052-2062.

Spröer et al., The phylogenetic position of *Serratia, Buttiauxella* and some other genera of the family Enterobacteriaceae, Int J System Bacteriol. (1999) 49: 1433-1438.

Stackebrandt et al., Taxonomic note: A place for DNA-DNA reassociation and 16S rRNA sequence analysis in the present species definition in bacteriology, Int J System Bacteriol. (1994) 44(4): 846-849.

Stager et al., Automated Systems for Identification of Microorganisms, Clin Microbiol Rev. (1992) 5(3): 302-327.

Stark, et al., Bacteriuria in the Catherized Patient: What Quantitative Level of Bacteriuria is Relevant? N Engl J Med. (1984) 311(9): 560-564.

Steigerwalt et al., DNA relatedness among species of *Enterobacter* and *Serratia*, Can J Microbiol. (1976) 22: 121-137.

Takezaki et al. Phylogenetic test of the molecular clock and linearized trees, Mol Biol Evol. (1995) 12(5): 823-833.

Taylor, Remotely related sequences and structures: analysis and predictive modelling, Trends Biotechnol. (1994) 12(5): 154-158.

Tyagi et al., Molecular beacons: probes that fluoresce upon hybridization, Nature Biotech. (1996) 14: 303-308.

Van Burik et al., Panfungal PCR Assay for Detection of Fungal Infection in Human Blood Specimens, J Clin Microbiol. (1998) 36(5): 1169-1175.

Vijgenboom et al., Three *tuf*-like genes in the Kirromycin producer *Streptmyc s ramocissimus*, Microbiol. (1994) 140: 983-998.

Wang et al., Phylogenetic analysis and identification of *Shigella spp by molecular probes, Mol Cell Probes* (1997) 11: 427-432.

Watson et al., Molecular Biology of the Gene, 4th Ed. The Genetic Code; The Benjamin/Cummings Publishing Company, Inc., (1976) Chapter 15, pp. 339-358.

Watson et al., Molecular Biology of the Gene, vol. I—General Principles; 4th Ed. The Benjamin/Cummings Publishing Company, Inc., (1987) pp. 431-462.

Wayne et al., Report of the Ad Hoc Committee on Reconciliation of approaches to bacterial systematics, Int J Sys Bacter. (1987) 37(4): 463-464.

Weaver et al., Incidence of methanogenic bacteria in a sigmoidoscopy population: an association of methanogenic bacteria and diverticulosis, Gut 27: 698-704.

Westin et al., Anchored multiplex amplification on a microelectronic chip array, Nature Biotech. (2000) 18: 199-204.

Whitcombe et al., Detection of PCR products using self-probing amplicons and fluorescence, Nature Biotech. (1999) 17: 804-807.

Wittwer et al., The LightCycler™: A microvolume multisample fluorimeter with rapid temperature control, Bio Techniques (1997) 22: 176-181.

York, et al, Evaluation of the autoSCAN-W/A Rapid System for Identification and Susceptibility Testing of Gram-Negative Fermentative Bacilli, J Clin Microbiol. (1992) 30(11): 2903-2910.

Yoshikawa et al., *Bacillus subtilis* Genes for RNA Polymerase beta Subunit, Ribosomal Proteins L 12 and S7, Elongation Factors G and Tu and Ribosomal Proteins S10 and L3, Submitted to DDB/EMBL/Genbank database on Apr. 15, 1995.

Aragón et al., Increase in β-lactam-resistant *Proteus mirabilis* Strains due to CTX-M- and CMY-type as well as New VEB-and Inhibitor-resistant TEM-type β-lactamases, J Antimicro Chemother. (2008) 61: 1029-1032.

Bagley et al., Significance of Fecal Coliform-positive *Klebsiella*, App Environ Microbio. (May 1977) 33(5): 1141-1148.

Duncan, Susceptibility of 1,500 Isolates of *Pseudomonas aeruginosa* to Gentamicin, Carbenicillin, Colistin, and Polymyxin B, Antimicro Agents Chemother. (Jan. 1974) 5(1): 9-15.

Feizabadi, Drug Resistant Patterns of *Enterococci Recovered from Patients in Tehran During 2000-2003, Letters to the Editor, Int J Antimicrob Agents* (2004) 24: 521-522.

Fenoll et al., Serotype Distribution and Antimicrobial Resistance of *Streptococcus pneumoniae* Isolates Causing Systemic Infections in Spain, 1979-1989, (1991) 13: 56-60.

Higashide et al., Methicillin-resistant *Staphylococcus saprophyticus* Isolates Carrying *Staphylococcal* Cassette Chromosome *mec* Have Emerged in Urogenital Tract Infections, Antimicrob Agents Chemother. (Jun. 2008) 52(6): 2061-2068.

Madico et al., Touchdown Enzyme Time Release-PCR for Detection and Identification of *Chlamydia trachomatic, C. pneumoniae*, and *C. psittaci* Using the 16S and 168-235 Spacer rRNA Genes, J Clin Microbiol., (Mar. 2000) 38(3): 1085-1093.

Metherell et al., Rapid, sensitive, mircobial detection by gene amplification using restriction endonuclease target sequences, Mol Cell Probes (1997) 11: 297-308.

NCBI Blast: Nucleotide Sequence, Attachment for Sequence Comparison between 5'-CCAGCTGTA TTAGAAGTA-3' from Seq ID No. 9 and Genomes of *Bacteria Bacillus Cereus* Q1 and AH187, (online: Apr. 12, 2009) 1 page.

NCBI Blast: Nucleotide Sequence, Attachment for Sequence Comparison between 5'CTGAACATTATC TTTGAT-3' from Seq ID No. 10 and Complete Genome of *Streptococcus Mutans* UA159, (online: Apr. 12, 2009) 1 page.

Paradis et al., The Potential of EF-Tu Sequences for Identification of Clinically Important *Enterobacteriaceae* Species (Sep. 1999) 39: 227; Abstract 1574.

Post et al., Development and Validation of a Multiplex PCR-based Assay for the Upper Respiratory Tract Bacterial Pathogens *Haemophilus influenzae, Streptococcus pneumoniae*, and *Moraxella catarrhalis*, (1996) 1(1): 29-39, Molecular Diagnosis vol. 1 No. 1.

Zhanel et al., Antimicrobial Resistance in *Haemophilus influenzae* and *Moraxella catarrhalis* Respiratory Tract Isolates: Results of the Canadian Respiratory Organizm Susceptibility Study, 1997 to 2002, Antimicrob Agents Chemother., (Jun. 2003) 47(6): 1875-1881.

Zhang et al., Cloning, Sequencing, and Expression in *Escherichia coli* of the Gene Encoding a 45-Kilodalton Protein, Elongation Factor Tu, from *Chlamydia trachomatis* Serovar F, J Bacteriol. (1994) 176(4): 1184-1187.

Ako-Nai et al., The Characterization of Clinical Isolates of *Staphylococcus aureus* in Ile-Ife, Nigeria, J Med Microbiol. (1991) 34: 109-112.

Betzl et al., Identification of *Lactococci* and *Enterococci* by Colony Hybridization with 23S rRNA-Targeted Oligonucleotide Probes, Appl Environ Microbio., (Sep. 1990) 56(9):2927-2929.

Bongaerts et al., In Vitro Activities of BAY Y3118, Ciprofloxacin, Ofloxacin, and Fleroxacin against Gram-Positive and Gram-Negative Pathogens from Respiratory Tract and Soft Tissue Infections, Antimicro Agents Chemother. (Sep. 1993) 37(9):2017-2019.

Buck, et al., Design Strategies and Performance of Custom DNA Sequencing Primers, Biotechniques (1999) 27(3): 528-536.

Derecola et al., A 5-Year Surveillance Study of 44,691 Isolates of *Haemophilus Influenzae* Project Beta-Alert 1993-1997, Antimicro Agen Chemothera. (Jan. 1999) 43(1):185-186.

GenBANK Accession No. M37185, *Enterococcus faecalis* Gelatinase (gelE) Gene, Complete CDS (Apr. 1993).

GenBANK Accession No. Z26902, Phylogenetic Analysis Using 16S rDNA Sequencing of *Staphylococci* (Oct. 1993).

Guzmàn et al., Role of Adherence in Pathogenesis of *Enterococcus faecalis* Urinary Tract Infection and Endocarditis, Infect Immun. (Jun. 1989) 57(6): 1834-1838.

Izumiya et al., Characterization of Multidrug-Resistant *Salmonella enterica* Serovar Typhimurium Isolated in Japan, J Clin Microbio. (Jul. 2001) 39(7):2700-2703.

Jenkins, F. J., Basic Methods for the Detection of PCR Products, Genome Res. (Apr. 1994) 3:S77-S82.

Kim et al., Simultaneous Detection by PCR of *Escherichia coli, Listeria Monocytogenes* and *Salmonella typhimurium* in Artificially Inoculated Wheat Grain, Inter'l J Food Microbio. (Apr. 2006) 111:21-25.

Lewis et al., Emergence of Clinical Isolates of *Staphylococcus aureus* Resistant to Gentamicin and Correlation of Resistance with Bacteriophage Type, J Infect Diseases, (Mar. 1978) 137(3): 314-317.

Miller et al., Community Acquired Lobar Pneumonia in Patients with HIV Infection and AIDS, Thorax (Apr. 1994) 49:367-368.

Mitsuhashi M., Technical Report: Part 2. Basic Requirements for Designing Optimal PCR Primers, J Clin Lab Anal., (1996) 10: 285-293.

Neu, Harold C., The Crisis in Antibiotic Resistance, Science (Aug. 1992) 257:1064-1073.

Powers, Robert D., New Directions in the Diagnosis and Therapy of Urinary Tract Infections, (1991) Am J Obstet Gynecol., 164:1387-1389.

Bej et al., Detection of coliform bacteria and *Escherichia coli* by multiplex polymerase chain reaction: Comparison with defined substrate and plating methods for water quality monitoring, Appl Environ Microbio., (Aug. 1991) 57(8): 2429-2432.

Cebula, et al., Simultaneous identification of strains of *Escherichia coli* Serotype O157:H7 and their shiga-like toxin type by mismatch amplification mutation assay-multiplex PCR, J Clin Microbio. (Jan. 1995) 33(1): 248-250.

Frankel et al., Multi-gene amplification: simultaneous detection of three virulence genes in diarrhoeal stool, Mol Microbio. (1989) 3(12): 1729-1734.

GenBank Accession No. FJ858146, *Enterococcus faecium* Strain QSE32 fsr Operon, Complete Sequence; and GelE (gelE) and SprE (sprE) Genes, Complete CDS, (Nov. 2009) http://www.ncbi.nlm.nih.gov/nuccore/226938234.

GenBank Accession No. AP000565, *Homo Sapiens* Genomic DNA, Chromosome 21Q22, clone:f79A10, D21S226-AML Region, Complete Sequence, (Nov. 1999) http://www.ncbi.nlm.nih.gov/nuccore/6015482.

Haas et al., Universal PCR primers for detection of phytopathogenic *Agrobacterium* strains, App Environ Microbio., (Aug. 1995) 61(8): 2879-2884.

Harth et al., Epidemiology of *Vibrio parahaemolyticus* Outbreaks, Southern Chile, Emerg Infect Dis., (Feb. 2009) 15(2): 163-168 and GenBank Accession No. EU185084 downloaded from http://ncbi.nlm.nih.gov/nuccore/158524083.

Kaltenboeck et al., Two-step polymerase chain reactions and restriction endonuclease analyses detect and differentiate *ompA* DNA of *Chlamydia* spp., J Clin Microbio. (May 1992) 30(5): 1098-1104.

Lucotte et al., A multiple primer pairs polymerase chain reaction for the detection of human genital papillomavirus types, Mol Cell Probes (1993) 7: 339-344.

Opposition Brief by Infectio Diagnostic (I.D.I.) Inc. dated Sep. 14, 2007 from EP Application No. 95931109.3, filed Sep. 12, 1995.

Opposition Brief by Roche Diagnostics GmbH dated Sep. 21, 2007 from EP Application No. 95931109.3, filed Sep. 12, 1995.

Reply Brief by Roche Diagnostics GmbH dated Jan. 29, 2008 to Opposition Brief by I.D.I. from EP Application No. 95931109.3, filed Sep. 12, 1995 (w/English translation).

Reply Brief by I.D.I. dated Apr. 1, 2008 to Roche's Appeal Brief from EP Application No. 95931109.3, filed Sep. 12, 1995.

EPO Notice of Summons to Oral Proceedings and Preliminary Opinion dated May 20, 2010 from EP Application No. 95931109.3, filed Sep. 12, 1995.

Reply Brief by I.D.I. dated Sep. 6, 2010 to Summons/Preliminary Opinion from EP Application No. 95931109.3, filed Sep. 12, 1995.

Reply Brief by Roche dated Sep. 6, 2010 to Summons/Preliminary Opinion from EP Application No. 95931109.3, filed Sep. 12, 1995 (w/English translation).

EPO Notice of Decision of Appeal dated Oct. 6, 2010 from EP Application No. 95931109.3, filed Sep. 12, 1995.

\* cited by examiner

SEQUENCE LISTING

<160> NUMBER OF SEQ ID NOS: 177

<210> SEQ ID NO 1
<211> LENGTH: 1817
<212> TYPE: DNA
<213> ORGANISM: Enterococcus faecalis

<400> SEQUENCE: 1

| | | | | | |
|---|---|---|---|---|---|
| acagtaaaaa | agttgttaac | gaatgaattt | gttaacaact | tttttgctat | ggtattgagt | 60 |
| tatgaggggc | aatacaggga | aaaatgtcgg | ctgattaagg | aatttagata | gtgccggtta | 120 |
| gtagttgtct | ataatgaaaa | tagcaacaaa | tatttacgca | gggaaagggg | cggtcgttta | 180 |
| acgggaaaaa | ttagggagga | taaagcaata | cttttgttgg | gaaagaaat | aaaggaaac | 240 |
| tggggaagga | gttaattgtt | tgatgaaggg | aaataaaatt | ttatacattt | taggtacagg | 300 |
| catctttgtt | ggaagttcat | gtctattttc | ttcacttttt | gtagccgcag | aagaacaagt | 360 |
| ttattcagaa | agtgaagttt | caacagtttt | atcgaagttg | aaaaggagg | caatttctga | 420 |
| ggcagctgct | gaacaatata | cggttgtaga | tcgaaaagaa | gacgcgtggg | ggatgaagca | 480 |
| tcttaagtta | gaaaagcaaa | cggaaggcgt | tactgttgat | tcagataatg | tgattattca | 540 |
| tttagataaa | aacggtgcag | taacaagtgt | tacaggaaat | ccagttgatc | aagttgtgaa | 600 |
| aattcaatcg | gttgatgcaa | tcggtgaaga | aggagttaaa | aaaattgttg | cttctgataa | 660 |
| tccagaaact | aaagatcttg | tctttttagc | tattgacaaa | cgtgtaaata | atgaagggca | 720 |
| attattttat | aaagtcagag | taacttcttc | accaactggt | gaccccgtat | cattggttta | 780 |
| taaagtgaac | gctacagatg | gaacaattat | ggaaaaacaa | gatttaacgg | aacatgtcgg | 840 |
| tagtgaagta | acgttaaaaa | actcttttca | agtaacgttt | aatgtaccag | ttgaaaaaag | 900 |
| caatacggga | attgctttac | acggaacgga | taacacaggg | gtttaccatg | cagtagttga | 960 |
| tggcaaaaat | aattattcta | ttattcaagc | gccatcacta | gcgacattaa | atcagaatgc | 1020 |
| tattgacgcc | tatacgcatg | gaaaatttgt | gaaaacatat | tatgaagatc | atttccaacg | 1080 |
| acacagtatt | gatgatcgag | ggatgcccat | cttgtcagtt | gttgatgaac | aacatccaga | 1140 |
| tgcttatgac | aatgcttttt | gggatggaaa | agcaatgcgt | tatggtgaaa | caagtacacc | 1200 |
| aacaggaaaa | acgtatgctt | cctctttaga | tgtagttggt | catgaaatga | cacatggtgt | 1260 |
| gacggaacat | actgccggtt | tagaatattt | aggacaatca | ggtgccttga | atgaatctta | 1320 |
| ttctgatttg | atgggttata | ttatttcggg | tgcatctaat | ccagaaattg | gtgcggatac | 1380 |
| tcagagtgtt | gaccgaaaaa | caggtattcg | aaatttacaa | acgccaagta | aacacggaca | 1440 |
| accagaaacc | atggctcaat | acgacgatcg | agcacggtat | aaaggaacgc | cttattatga | 1500 |
| tcaaggcggt | gttcattata | acagtggaat | tattaatcgg | attggttaca | ccattatcca | 1560 |
| gaacttaggc | attgaaaaag | cacagactat | tttctacagc | tcgttagtaa | attacttaac | 1620 |
| acctaaagca | caattcagtg | atgctcgtga | tgcgatgctt | gctgctgcaa | aagttcaata | 1680 |
| tggcgatgaa | gcagcttcag | tggtgtcagc | agcctttaac | tctgctggaa | tcggagctaa | 1740 |
| agaagacatt | caggtaaacc | aaccaagtga | atctgttctg | gtcaatgaat | gaaaaaaatt | 1800 |
| ccccaattaa | ataaaaa | | | | | 1817 |

<210> SEQ ID NO 2
<211> LENGTH: 2275
<212> TYPE: DNA
<213> ORGANISM: Enterococcus faecalis

<400> SEQUENCE: 2

```
ggtaccaaag aaaaaaacga acgccacaac caacagcctc taaagcaaca cctgcttctg      60
aaattgaggg agatttagca aatgtcaatg agattctttt ggttcacgat gatcgtgtcg     120
ggtcagcaac gatgggaatg aaagtcttag aagaaatttt agataaagag aaatttcaa     180
tgccgattcg aaaaattaat attaatgaat taactcaaca aacacaggct taattgtca     240
caaaagctga actaacggaa caagcacgta aaaagcacc gaaagcgaca cacttatcag     300
taaaaagtta tggttaatcc ccaaaaatat gaaacagtgg gtttcgctct taaaagaaag     360
tgcctagaga ggaagaaaac aatggaaaat cttacgaata tttcaattga attaaatcaa     420
cagtttaata caaaagaaga agctattcgc ttttccggcc agaaactagt cgaggcaggc     480
tgtgttgagc ccgcttatat cgaagcaatg attgaaagag accaattgct atctgcccat     540
atggggaatt ttattgccat tcctcatgga acagaagaag ccaaaaaatt agtgaaaaaa     600
tcaggaatct gtgtagtgca agtcccagag ggcgttaatt ttggcaccga agaagatgaa     660
aaaattgcta ccgtattatt tgggattgcc ggagtcggtg aagaacattt gcaattagtc     720
caacaaattg cactttattg tagtgatatg ataacgtgg tgcaacttgc cgatgcatta     780
agtaaagaag aaataacaga aaatttagcc attgcttaaa ggagagaata agaatgaacg     840
cagtacattt tggagcagga aatattggac gcggctttat tggcgaaatt ttagctaaaa     900
cgggtttcat attaccgttt gtggatgtta atggaaacca tcatcaagcg ttaaaagaac     960
gtaaaagtta tacaattgaa ttggccgatg cctcacatca acaaattaac gttgaaaatg    1020
tgaccgggtt aaataacatg acagaaccag aaaaagtagt agaagcaatt gcggaagccg    1080
atttagtcac gacggcaatt ggtcctaata ttttaccaag aattgctgaa ttaattgctc    1140
aaggaattga tgcacgtgcc gaagcaaatt gtcaaaacgg cccgctggat attatcgctt    1200
gtgaaaatat gattggtggt tcaacctttt tagcagaaga agtggccata atatttgaaa    1260
aacccagctt atctgaacaa tggattggtt ttcctgatgc ggcagttgat cggattgttc    1320
cattacaaaa acataaagat ccactttttg ttcaagttga gccttttgt gaatgggtca    1380
ttgatgatac caaccgaaaa gccaaagaga ttcagttaga aggcgtcatt acttgtcgat    1440
tagagccgta tattgaacga aaattattta gtgtaaccag tggccatgct acagttgcct    1500
atacagggc gttgttaggc tatcaaacca ttgacgaagc gatgcaggac gccttagtgg    1560
tagcgcaact caaatcagtt ttgcaggaaa ccggtaaact tttagtggcc aaatggaatt    1620
ttgatgaaca agaacatgca gcctatattg aaaaaattat caaccgtttc caaaataaat    1680
atatttcaga tgctattaca cgtgtagcac ggacaccaat cagaaaatta ggtgcgcaag    1740
aacggtttat tcgaccaatc cgtgaattac aggaacgcaa tctagtgtcg gccgcattta    1800
tagcaatgat tggtattgtc tttaattatc atgatccaga agatgaacaa agccgtcaat    1860
tacaggaaat gcttgaccaa gaaagtgttg atacagtgga tcgctgaagt aacgggcatt    1920
gaagatccag aaacggttaa aaatattaaa caaaacgtag aactgctatg cgcgaccaca    1980
agtagcataa ttaacaaaat ccttctacca agatacttca catttcttaa ttaaagaaaa    2040
aacaaccgcg cctcacctga gccgaccccc aaaagttaga cctagaaatc taacttttgg    2100
aggttttttt gtatggcaaa atacagtttt gaaatttaaa cttaaacttg ttcatgacta    2160
cttatatggt caaggaggtc taaggtttct cgcaaagaag tatgggttta aagatagtct    2220
caaataagca aatggataaa tgcctataaa gaacttggtg aagaagggg gatcc         2275
```

<210> SEQ ID NO 3

```
<211> LENGTH: 227
<212> TYPE: DNA
<213> ORGANISM: Escherichia coli

<400> SEQUENCE: 3
gatccgccat gggttgtttt ccgattgagg attttataga tggtttctgg cgacctgcac      60
aggagtacgg tgattttaa ttattgcaat tgcacaagag tcagttctcc cccaaagaca      120
gcaccggtat caatataatg caggttgcca atatccacgc gatggcgcaa aggtgtatga      180
ccaaaccaga atgatcggc cacctgcatc gccagttcgc gagtcgg                     227

<210> SEQ ID NO 4
<211> LENGTH: 278
<212> TYPE: DNA
<213> ORGANISM: Escherichia coli

<400> SEQUENCE: 4
gatctaaatc aaattaattg gttaaagata accacagcgg ggccgacata aactctgaca      60
agaagttaac aaccatataa cctgcacagg acgcgaacat gtcttctcat ccgtatgtca     120
cccagcaaaa tacccgctg gcggacgaca ccactctgat gtccactacc gatctcgctt      180
tccagcgtca tattgggggcg cgctacgttg gggcgtgggc gtaattggtc aatcaggcgc    240
ggggtcagcg gataaacatt caccattttg tcgagatc                             278

<210> SEQ ID NO 5
<211> LENGTH: 1596
<212> TYPE: DNA
<213> ORGANISM: Escherichia coli

<400> SEQUENCE: 5
atggctgaca ttctgctgct cgataatatc gactctttta cgtacaacct ggcagatcag      60
ttgcgcagca tgggcataaa cgtggtgatt taccgcaacc atataccggc gcaaaccttca    120
attgaacgct tggcgaccat gagtaatccg gtgctgatgc tttctcctgg ccccggtgtg     180
ccgagcgaag ccggttgtat gccggaactc ctcacccgct tgcgtggcaa gctgcccatt     240
attggcattt gcctcggaca tcaggcgatt gtcgaagctt acggggggcta tgtcggtcag    300
gcgggcgaaa ttctccacgg taaagcctcc agcattgaac atgacggtca ggcgatgttt    360
gccggattaa caaacccgct gccggtggcg cgttatcact cgctggttgg cagtaacatt    420
ccggccggtt taaccatcaa cgcccatttt aatggcatgg tgatggcagt acgtcacgat    480
gcggatcgcg tttgtggatt ccagttccat ccggaatcca ttctcaccac ccagggcgct    540
cgcctgctgg aacaaacgct ggcctgggcg cagcataaac tagagccagc caacacgctg    600
caaccgattc tggaaaaact gtatcaggcg cagacgctta gccaacaaga aagccaccag    660
ctgttttcag cggtggtgcg tggcgagctg aagccggaac aactggcggc ggcgctggtg    720
agcatgaaaa ttcgcggtga gcacccgaac gagatcgccg gggcagcaac cgcgctactg    780
gaaaacgcag cgccgttccc gcgcccggat tatctgtttg ctgatatcgt cggtactggc    840
ggtgacggca gcaacagtat caatatttct accgccagtg cgtttgtcgc gcggcctgt    900
gggctgaaag tggcgaaaca cggcaaccgt agcgtctcca gtaaatctgg ttcgtccgat    960
ctgctggcgg cgttcggtat taatcttgat atgaacgccg ataaatcgcg ccaggcgctg   1020
gatgagttag gtgtatgttt cctctttgcg ccgaagtatc acaccggatt ccgccacgcg   1080
atgccggttc gccagcaact gaaaacccgc accctgttca atgtgctggg gccattgatt   1140
aacccggcgc atccgccgct ggcgttaatt ggtgtttata gtccggaact ggtgctgccg   1200
```

| | |
|---|---:|
| attgccgaaa ccttgcgcgt gctggggtat caacgcgcgg cggtggtgca cagcggcggg | 1260 |
| atggatgaag tttcattaca cgcgccgaca atcgttgccg aactgcatga cggcgaaatt | 1320 |
| aaaagctatc agctcaccgc agaagacttt ggcctgacac cctaccacca ggagcaactg | 1380 |
| gcaggcggaa caccggaaga aaaccgtgac attttaacac gtttgttaca aggtaaaggc | 1440 |
| gacgccgccc atgaagcagc cgtcgctgcg aacgtcgcca tgttaatgcg cctgcatggc | 1500 |
| catgaagatc tgcaagccaa tgcgcaaacc gttcttgagg tactgcgcag tggttccgct | 1560 |
| tacgacagag tcaccgcact ggcggcacga gggtaa | 1596 |

<210> SEQ ID NO 6
<211> LENGTH: 2703
<212> TYPE: DNA
<213> ORGANISM: Escherichia coli

<400> SEQUENCE: 6

| | |
|---|---:|
| gacgacttag ttttgacgga atcagcatag ttaatcactt cactgtggaa atgaggaaa | 60 |
| tattattttt tttgcgcttc gtaattaatg gttataaggt cggccagaaa ccttcctaat | 120 |
| gcaagcgatg acgttttttt atgtgtctga atttgcactg tgtcacaatt ccaaatcttt | 180 |
| attaacaact cacctaaaac gacgctgatc cagcgtgaat actggtttcc cttatgttca | 240 |
| tcagattcat ttaagcaagg gtttcttctt cattcctgat gaaagtgcca tctaaaaaga | 300 |
| tgatcttaat aaatctatta agaatgagat ggagcacact ggatatttta cttatgaaac | 360 |
| tgtttcactc ctttacttaa tttatagagt taccttccgc ttttttgaaaa tacgcaacgg | 420 |
| ccatttttg cacttagata cagattttct gcgctgtatt gcattgattt gatgctaatc | 480 |
| ctgtggtttg cactagcttt aagtggttga gatcacattt ccttgctcat ccccgcaact | 540 |
| cctccctgcc taatcccccg caggatgagg aaggtcaaca tcgagcctgg caaactagcg | 600 |
| ataacgttgt gttgaaaatc taagaaaagt ggaactccta tgtcacaacc tattttaac | 660 |
| gataagcaat tcaggaagc gctttcacgt cagtggcagc gttatggctt aaattctgcg | 720 |
| gctgaaatga ctcctcgcca gtggtggcta gcagtgagtg aagcactggc cgaaatgctg | 780 |
| cgtgctcagc cattcgccaa gccggtggcg aatcagcgac atgttaacta catctcaatg | 840 |
| gagtttttga ttggtcgcct gacgggcaac aacctgttga atctcggctg gtatcaggat | 900 |
| gtacaggatt cgttgaaggc ttatgacatc aatctgacgg acctgctgga agaagagatc | 960 |
| gacccggcgc tgggtaacgg tggtctggga cgtctggcgg cgtgcttcct cgactcaatg | 1020 |
| gcaactgtcg gtcagtctgc gacgggttac ggtctgaact atcaatatgg tttgttccgc | 1080 |
| cagtcttttg tcgatggcaa acaggttgaa gcgccggatg actggcatcg cagtaactac | 1140 |
| ccgtggttcc gccacaacga agcactggat gtgcaggtag ggattggcgg taaagtgacg | 1200 |
| aaagacggac gctgggagcc ggagtttacc attaccggtc aagcgtggga tctccccgtt | 1260 |
| gtcggctatc gtaatggcgt ggcgcagccg ctgcgtctgt ggcaggcgac gcacgcgcat | 1320 |
| ccgtttgatc tgactaaatt taacgacggt gatttcttgc gtgccgaaca gcagggcatc | 1380 |
| aatgcggaaa aactgaccaa agttctctat ccaaacgaca accatactgc cggtaaaaag | 1440 |
| ctgcgcctga tgcagcaata cttccagtgt gcctgttcgg tagcggatat tttgcgtcgc | 1500 |
| catcatctgg cggggcgtga actgcacgaa ctggcggatt actaagttat tcagctgaac | 1560 |
| gatacccacc caactatcgc gattccagaa ctgctgcgcg tgctgatcga tgagcaccag | 1620 |
| atgagctggg atgacgcttg gccattacc agcaaaactt tcgcttacac caaccatacc | 1680 |
| ctgatgccag aagcgctgga acgctgggat gtgaaactgg tgaaaggctt actgccgcgc | 1740 |

-continued

| | |
|---|---|
| cacatgcaga ttattaacga aattaatact cgctttaaaa cgctggtaga gaaaacctgg | 1800 |
| ccgggcgatg aaaaagtgtg ggccaaactg gcggtggtgc acgacaaaca agtgcatatg | 1860 |
| gcgaacctgt gtgtggttgg cggtttcgcg gtgaacggtg ttgcggcgct gcactcggat | 1920 |
| ctggtggtga aagatctgtt cccggaatat caccagctat ggccgaacaa attccataac | 1980 |
| gtcaccaacg gtattacccc acgtcgctgg atcaaacagt gcaacccggc actggcggct | 2040 |
| ctgttggata aatcactgca aaaagagtgg gctaacgatc tcgatcagct gatcaatctg | 2100 |
| gttaaattgg ctgatgatgc gaaattccgt cagctttatc gcgtgatcaa gcaggcgaat | 2160 |
| aaagtccgtc tggcggagtt tgtgaaagtt cgtaccggta ttgacatcaa tccacaggcg | 2220 |
| attttcgata ttcagatcaa acgtttgcac gagtacaaac gccagcacct gaatctgctg | 2280 |
| cgtattctgg cgttgtacaa agaaattcgt gaaaacccgc aggctgatcg cgtaccgcgc | 2340 |
| gtcttcctct tcggcgcgaa agcggcaccg ggctactacc tggctaagaa tattatcttt | 2400 |
| gcgatcaaca aagtggctga cgtgatcaac aacgatccgc tggttggcga taagttgaag | 2460 |
| gtggtgttcc tgccggatta ttgcgtttcg gcggcggaaa aactgatccc ggcggcggat | 2520 |
| atctccgaac aaatttcgac tgcaggtaaa gaagcttccg gtaccggcaa tatgaaactg | 2580 |
| gcgctcaatg gtgcgcttac tgtcggtacg ctggatgggg cgaacgttga aatcgccgag | 2640 |
| aaagtcggtg aagaaaatat ctttattttt ggtcatacgg tcaaacaagt gaaggcaatc | 2700 |
| gac | 2703 |

<210> SEQ ID NO 7
<211> LENGTH: 1391
<212> TYPE: DNA
<213> ORGANISM: Escherichia coli

<400> SEQUENCE: 7

| | |
|---|---|
| agagaagcct gtcggcaccg tctggttttgc ttttgccact gcccgcggtg aaggcattac | 60 |
| ccggcgggat gcttcagcgg cgaccgtgat gcggtgcgtc gtcaggctac tgcgtatgca | 120 |
| ttgcagacct tgtggcaaca atttctacaa acacttgat actgtatgag catacagtat | 180 |
| aattgcttca acagaacata ttgactatcc ggtattaccc ggcatgacag gagtaaaaat | 240 |
| ggctatcgac gaaacaaac agaaagcgtt ggcggcagca ctgggccaga ttgagaaaca | 300 |
| atttggtaaa ggctccatca tgcgcctggg tgaagaccgt tccatggatg tggaaaccat | 360 |
| ctctaccggt tcgctttcac tggatatcgc gcttgggca ggtggtctgc cgatgggccg | 420 |
| tatcgtcgaa atctacggac cggaatcttc cggtaaaacc acgctgacgc tgcaggtgat | 480 |
| cgccgcagcg cagcgtgaag gtaaaacctg tgcgtttatc gatgctgaac acgcgctgga | 540 |
| cccaatctac gcacgtaaac tgggcgtcga tatcgacaac ctgctgtgct cccagccgga | 600 |
| caccggcgag caggcactgg aaatctgtga cgccctggcg cgttctggcg cagtagacgt | 660 |
| tatcgtcgtt gactccgtgg cggcactgac gccgaaagcg aaatcgaag gcgaaatcgg | 720 |
| cgactctcac atgggccttg cggcacgtat gatgagccag gcgatgcgta agctggcggg | 780 |
| taacctgaag cagtccaaca cgctgctgat cttcatcaac cagatccgta tgaaaattgg | 840 |
| tgtgatgttc ggtaacccgg aaaccactac cggtggtaac gcgctgaaat tctacgcctc | 900 |
| tgttcgtctc gacatccgtc gtatcggcgc ggtgaaagag ggcgaaaacg tggtgggtag | 960 |
| cgaaacccgc gtgaaagtgg tgaagaacaa aatcgctgcg ccgtttaaac aggctgaatt | 1020 |
| ccagatcctc tacggcgaag gtatcaactt ctacggcgaa ctggttgacc tgggcgtaaa | 1080 |
| agagaagctg atcgagaaag caggcgcgtg gtacagctac aaaggtgaga agatcggtca | 1140 |

-continued

```
gggtaaagcg aatgcgactg cctggctgaa agataacccg gaaaccgcga aagagatcga      1200
gaagaaagta cgtgagttgc tgctgagcaa cccgaactca acgccggatt tctctgtaga      1260
tgatagcgaa ggcgtagcag aaactaacga agatttttaa tcgtcttgtt tgatacacaa      1320
gggtcgcatc tgcggccctt ttgctttttt aagttgtaag gatatgccat gacagaatca      1380
acatcccgtc g                                                           1391
```

<210> SEQ ID NO 8
<211> LENGTH: 238
<212> TYPE: DNA
<213> ORGANISM: Klebsiella pneumoniae

<400> SEQUENCE: 8

```
tcgccaggaa ggcggcattc ggctgggtca gagtgacctg cagcgtggtg tcgttcagcg       60
cttttacccc caacgtctcg ggtcccttt gcccgagggc aatctcgcgg gcgttggcga       120
tatgcatatt gccagggtag ctcgcgtagg gggaggctgt tgccggcgag accagccgtt      180
gccagctcca gacgatatcc tgcgctgtaa tggccgtgcc gtcagaccag gtcagacc        238
```

<210> SEQ ID NO 9
<211> LENGTH: 385
<212> TYPE: DNA
<213> ORGANISM: Klebsiella pneumoniae

<400> SEQUENCE: 9

```
cagcgtaatg cgccgcggca taacggcgcc actatcgaca gtcagttcgt cagcctgcag       60
cctgggctga atctgggacc atggcgcctg ccgaactaca gcacctatag ccacagcgat      120
aacaacagcc gctgggagtc ggtttactcc tatcttgccc gcgatattca caccctacgc      180
agccagctgg tggtcggtaa tacgtatacc tcttccggca ttttcgacag tttgagtttt      240
accggtctgc agctcagttc gacaaagaga tgctgccgga tagcctgcat gctttgcgcc      300
gacgattcga gggatcgcgc gcaccaccgc ggaggtctcg gtttatcaga atggttacag      360
catttataaa accaccgtcg ctacc                                            385
```

<210> SEQ ID NO 10
<211> LENGTH: 462
<212> TYPE: DNA
<213> ORGANISM: Klebsiella pneumoniae

<400> SEQUENCE: 10

```
ctctatattc aggacgaaca tatctggacc tctggcgggg tcagttccgg ctttgatcgc       60
cctgcacccg cagcgggtga tcgcccctca tctgctactg cggcgctgca acaggcgacg      120
atcgatgacg ttattcctgg ccagcaaaca gcagaccaat taaggtctga tagtggctct      180
cttcctccgg cgcgcgacgg tccaggcggc tcaacagttt ggtgcatagc gctttgcggt      240
tgagatgacg cccttcgtta agaatatcca tcacgatctc cgtccatgga gagtagcgtt      300
tattccagaa tagggttttt caggatctca tggatctgcg cctgcttatc gctattttgt      360
aaccagatcg cataaagtgg acgggataac gtagcgctgt ccatgaccgt atgtaaccca      420
tgcttctctt tcgcccagcg agcaggtagc caacagcagc cg                        462
```

<210> SEQ ID NO 11
<211> LENGTH: 730
<212> TYPE: DNA
<213> ORGANISM: Klebsiella pneumoniae

<400> SEQUENCE: 11

```
gctgaccgct aaactgggtt acccgatcac tgacgatctg gacatctaca cccgtctggg    60
cggcatggtt tggcgcgctg actccaaagg caactacgct tcaaccggcg tttcccgtag   120
cgaacacgac actggcgttt ccccagtatt tgctggcggc gtagagtggg ctgttactcg   180
tgacatcgct acccgtctgg aataccagtg ggttaacaac atcggcgacg cgggcactgt   240
gggtacccgt cctgataacg gcatgctgag cctgggcgtt tcctaccgct tcggtcagga   300
agatgctgca ccggttgttg ctccggctcc ggctccggct ccggaagtgg ctaccaagca   360
cttcaccctg aagtctgacg ttctgttcaa cttcaacaaa gctaccctga aaccggaagg   420
tcagcaggct ctggatcagc tgtacactca gctgagcaac atggatccga agacggttc    480 cgctgttgtt ctgggctaca ccgaccgcat cggttccgaa gcttacaacc agcagctgtc   540
tgagaaacgt gctcagtccg ttgttgacta cctggttgct aaaggcatcc cggctggcaa   600
aatctccgct cgcggcatgg gtgaatccaa cccggttact ggcaacacct gtgacaacgt   660
gaaagctcgc gctgccctga tcgattgcct ggctccggat cgtcgtgtag agatcgaagt   720
taaaggtatc                                                          730

<210> SEQ ID NO 12
<211> LENGTH: 225
<212> TYPE: DNA
<213> ORGANISM: Proteus mirabilis

<400> SEQUENCE: 12
cgctactgtt taaatctcat ttgaaacatc gcaaagtcag tgaaccacat attcgaggat    60
ggcatgcact agaaaatatt aataagattt tagcgaaacc taatcagcgc aatatcgctt   120
aattatttta ggtatgttct cttctatcct acagtcacga ggcagtgtcg aacttgatcc   180
tcattttatt aatcacatga ccaatggtat aagcgtcgtc acata                   225

<210> SEQ ID NO 13
<211> LENGTH: 402
<212> TYPE: DNA
<213> ORGANISM: Proteus mirabilis

<400> SEQUENCE: 13
acattttaaa taggaagcca cctgataaca tccccgcagt tggatcatca gatttatagc    60
ggcatttggt atccgctaga taaaagcagt ccaacgatcc cgccaattgt tagatgaaat   120
tggactattc tttttatttg ctccgcttta tcacagtggt tttcgctttg ccgcccctgt   180
gcgccaacag ctaagaacac gcacgctctt taatgtgtta ggcccattaa ttaatccagc   240
gcgttccgcc tttagcatta attggtgttt atagtcctga attattaatg cctattgcag   300
ataccttaaa tgtcttgggc tacaaacgtg cggcagtggt ccatagtggt ggaatggatg   360
aagtgtcatt acatgctccc acacaagtgg ctgagttaca ca                     402

<210> SEQ ID NO 14
<211> LENGTH: 157
<212> TYPE: DNA
<213> ORGANISM: Proteus mirabilis

<400> SEQUENCE: 14
ctgaaacgca tttatgcggg agtcagtgaa atcatcactc aattttcacc cgatgtattt    60
tctgttgaac aagtctttat ggcaaaaaat gcagactcag cattaaaatt aggccaagca   120
agaggtgtgg cgattttagc ggcagtcaat aatgatc                           157

<210> SEQ ID NO 15
```

```
<211> LENGTH: 1348
<212> TYPE: DNA
<213> ORGANISM: Proteus mirabilis

<400> SEQUENCE: 15
tttctcttta aaatcaattc ttaaagaaat tattaataat taacttgata ctgtatgatt      60
atacagtata atgagtttca acaagcaaaa tcatatacgt tttaatggta gtgacccatc     120
tttatgcttc actgcccaga gggagataac atggctattg atgaaaacaa acaaaaagca     180
ttggccgcag cacttggtca aattgaaaag caatttggta aaggttctat catgcgtctg     240
ggcgaagacc gttccatgaa cgtagaaact atctctacag gatctttatc attagacgtt     300
gctttaggtg caggtggatt gccacgtggc cgtattgttg aaatctatgg ccctgaatct     360
tctggtaaaa caaccttgac tctacaagtt attgcctctg ctcagcgtga aggaaaaatt     420
tgtgcattta ttgatgctga acatgcatta gacccaattt atgctcaaaa gctaggtgtc     480
gatatcgata atctactctg ctctcaacct gacacaggtg aacaagctct ggaaatttgt     540
gatgcattat ctcgctctgg tgcggtcgat gttattgtcg tggactccgt ggcagcatta     600
acaccaaaag ctgaaattga aggtgaaatt ggtgattcac acgttggttt agccgcacgt     660
atgatgagcc aagctatgcg taaactagcg ggtaacctta aaaactctaa tacactgctg     720
atttcatta accaaattcg tatgaaaatc ggtgttatgt ttggtaaccc agaaaccacg     780
accggtggta atgcgcttaa attctatgct tctgttcgtt tagacattcg tcgcattggc     840
tctgtcaaaa atggtgatga agtcattggt agtgagactc gcgttaaagt tgttaaaaat     900
aaagtggctg caccgtttaa acaagctgaa ttccaaatta tgtacggtga aggtattaat     960
acctatggcg aactgattga tttaggtgtt aaacataagt tagtagagaa agcaggtgct    1020
tggtatagct acaatggcga aaaaattggt caaggtaaag ctaacgcaac caattactta    1080
aaagaacatc ctgaaatgta caatgagtta aacactaaat tgcgtgaaat gttgttaaat    1140
catgctggtg aattcacaag tgctgcggat tttgcaggtg aagagtcaga cagtgatgct    1200
gacgacacaa aagagtaatt agctggttgt catgctgttt gtgtgaaaat agaccttaaa    1260
tcattggcta ttatcacgac agcatcccat agaataactt gtttgtataa atttttattca   1320
gatggcaaag gaagccttaa aaaagctt                                        1348

<210> SEQ ID NO 16
<211> LENGTH: 2167
<212> TYPE: DNA
<213> ORGANISM: Pseudomonas aeruginosa

<400> SEQUENCE: 16
ggtaccgctg gccgagcatc tgctcgatca ccaccagccg ggcgacggga actgcacgat      60
ctacctggcg agcctggagc acgagcgggt tcgcttcgta cggcgctgag cgacagtcac     120
aggagaggaa acgatgggaa tcgcaccagg agcggccgct gatcggcctg ctgttctccg     180
aaaccggcgt caccgccgat atcgagcgct cgcacgcgta tggcgcattg ctcgcggtcg     240
agcaactgaa ccgcgagggc ggcgtcgcg gtcgcccgat cgaaacgctg tcccaggacc     300
ccggcggcga cccggaccgc tatcggctgt gcgccgagga cttcattcgc aaccgggggg     360
tacggttcct cgtgggctgc tacatgtcgc acacgcgcaa ggcggtgatg ccggtggtcg     420
agcgcgccga cgcgctgctc tgctacccga ccccctacga gggcttcgag tattcgccga     480
acatcgtcta cggcggtccg gcgccgaacc agaacagtgc gccgctggcg gcgtacctga     540
ttcgccacta cggcgagcgg gtggtgttca tcggctcgga ctacatctat ccgcgggaaa     600
```

-continued

```
gcaaccatgt gatgcgccac ctgtatcgcc agcacggcgg cacggtgctc gaggaaatct    660
acattccgct gtatccctcc gacgacgact tgcagcgcgc cgtcgagcgc atctaccagg    720
cgcgcgccga cgtggtcttc tccaccgtgg tgggcaccgg caccgccgag ctgtatcgcg    780
ccatcgcccg tcgctacggc gacggcaggc ggccgccgat cgccagcctg accaccagcg    840
aggcggaggt ggcgaagatg gagagtgacg tggcagaggg gcaggtggtg gtcgcgcctt    900
acttctccag catcgatacg cccgccagcc gggccttcgt ccaggcctgc catggtttct    960
tcccggagaa cgcgaccatc accgcctggg ccgaggcggc ctactggcag accttgttgc   1020
tcggccgcgc cgcgcaggcc gcaggcaact ggcgggtgga agacgtgcag cggcacctgt   1080
acgacatcga catcgacgcg ccacaggggc cggtccgggt ggagcgccag aacaaccaca   1140
gccgcctgtc ttcgcgcatc gcggaaatcg atgcgcgcgg cgtgttccag gtccgctggc   1200
agtcgcccga accgattcgc cccgaccctt atgtcgtcgt gcataacctc gacgactggt   1260
ccgccagcat gggcggggga ccgctcccat gagcgccaac tcgctgctcg gcagcctgcg   1320
cgagttgcag gtgctggtcc tcaacccgcc ggggaggtc agcgacgccc tggtcttgca    1380
gctgatccgc atcggttgtt cggtgcgcca gtgctggccg ccgccggaag ccttcgacgt   1440
gccggtggac gtggtcttca ccagcatttt ccagaatggc caccacgacg agatcgctgc   1500
gctgctcgcc gccgggactc cgcgcactac cctggtggcg ctggtggagt acgaaagccc   1560
cgcggtgctc tcgcagatca tcgagctgga gtgccacggc gtgatcaccc agccgctcga   1620
tgcccaccgg gtgctgcctg tgctggtatc ggcgcggcgc atcagcgagg aaatggcgaa   1680
gctgaagcag aagaccgagc agctccagga ccgcatcgcc ggccaggccc ggatcaacca   1740
ggccaaggtg ttgctgatgc agcgccatgg ctgggacgag cgcgaggcgc accagcacct   1800
gtcgcgggaa gcgatgaagc ggcgcgagcc gatcctgaag atcgctcagg agttgctggg   1860
aaacagcccg tccgcctgag cgatcccggc cgaccagaac aataacaaga ggggtatcgt   1920
catcatgctg gactggttc tgctgtacgt tggcgcggtg ctgtttctca atgccgtctg    1980
gttgctgggc aagatcagcg gtcgggaggt ggcggtgatc aacttcctgg tcggcgtgct   2040
gagcgcctgc gtcgcgttct acctgatctt ttccgcagca gccgggcagg gctcgctgaa   2100
ggccggagcg ctgaccctgc tattcgcttt tacctatctg tgggtggccg ccaaccagtt   2160
cctcgag                                                             2167
```

<210> SEQ ID NO 17
<211> LENGTH: 1872
<212> TYPE: DNA
<213> ORGANISM: Pseudomonas aeruginosa

<400> SEQUENCE: 17

```
gaattcccgg gagttcccga cgcagccacc cccaaaacac tgctaaggga gcgcctcgca     60
gggctcctga ggagatagac catgccattt ggcaagccac tggtgggcac cttgctcgcc    120
tcgctgacgc tgctgggcct ggccaccgct cacgccaagg acgacatgaa agccgccgag    180
caataccagg gtgccgcttc cgccgtcgat cccgctcacg tggtgcgcac caacggcgct    240
cccgacatga gtgaaagcga gttcaacgag gccaagcaga tctacttcca acgctgcgcc    300
ggttgccacg gcgtcctgcg caagggcgcc accggcaagc cgctgacccc ggacatcacc    360
cagcaacgcg gccagcaata cctggaagcg ctgatcacct acggcacccc gctgggcatg    420
ccgaactggg gcagctccgg cgagctgagc aaggaacaga tcaccctgat ggccaagtac    480
atccagcaca ccccgccgca accgccggag tggggcatgc cggagatgcg cgaatcgtgg    540
```

```
aaggtgctgg tgaagccgga ggaccggccg aagaaacagc tcaacgacct cgacctgccc      600
aacctgttct cggtgaccct gcgcgacgcc gggcagatcg ccctggtcga cggcgacagc      660
aaaaagatcg tcaaggtcat cgataccggc tatgccgtgc atatctcgcg gatgtccgct      720
tccggccgct acctgctggt gatcggccgc gacgcgcgga tcgacatgat cgacctgtgg      780
gccaaggagc cgaccaaggt cgccgagatc aagatcggca tcgaggcgcg ctcggtggaa      840
agctccaagt tcaagggcta cgaggaccgc tacaccatcg ccggcgccta ctggccgccg      900
cagttcgcga tcatggacgg cgagaccctg gaaccgaagc agatcgtctc caccccgcggc     960 atgaccgtag acacccagac ctaccacccg gaaccgcgcg tggcggcgat catcgcctcc     1020
cacgagcacc ccgagttcat cgtcaacgtg aaggagaccg gcaaggtcct gctggtcaac     1080
tacaaggata tcgacaacct caccgtcacc agcatcggtg cggcgccgtt cctccacgac     1140
ggcggctggg acagcagcca ccgctacttc atgaccgccg ccaacaactc caacaaggtt     1200
gccgtgatcg actccaagga ccgtcgcctg tcggccctgg tcgacgtcgg caagaccccg     1260 caccggggc gtggcgccaa cttcgtgcat cccaagtacg gccggtgtg gagcaccagc      1320 cacctggggcg acggcagcat ctcgctgatc ggcaccgatc cgaagaacca tccgcagtac     1380
gcctggaaga agtcgccga actacagggc cagggcggcg gctcgctgtt catcaagacc     1440
catccgaagt cctcgcacct ctacgtcgac accaccttca accccgacgc caggatcagc     1500
cagagcgtcg cggtgttcga cctgaagaac ctcgacgcca gtaccaggt gctgccgatc     1560 gccgaatggg ccgatctcgg cgaaggcgcc aagcgggtgg tgcagcccga gtacaacaag     1620
cgcggcgatg aagtctggtt ctcggtgtgg aacggcaaga cgacagctc cgcgctggtg     1680 gtggtggacg acaagaccct gaagctcaag gccgtggtca aggacccgcg gctgatcacc     1740
ccgaccggta agttcaacgt ctacaacacc cagcacgacg tgtactgaga cccgcgtgcg     1800
gggcacgccc cgcacgctcc cccctacgag gaaccgtgat gaaaccgtac gcactgcttt     1860
cgctgctcgc ca                                                       1872

<210> SEQ ID NO 18
<211> LENGTH: 3451
<212> TYPE: DNA
<213> ORGANISM: Pseudomonas aeruginosa

<400> SEQUENCE: 18
tcgagacggg aagccactct ctacgagaag acagaagccc ctcacagagg cctctgtcta       60
cgcctactaa agctcggctt attcatatgt atttatattc tttcaataga tcactcagcg      120
ctattttaag ttcaccctct gtaagttcac ctgggcgctc tttctttcct tcggtaaagc      180
tgtcggccag accaaacatt aaactcaagc atctcccaag cgatgcatca tcttgggcca      240
gcatccctga atcgcgcgtc ggacctccaa gtcttaaaaa attcttcgct gaaggttttc      300
ccatcaatcg atgaggctaa tagcttcttt gcaatatcta tcatttccat gctcacctta      360
aagcacctca tttttcatgt aaaaattgta ttgatccgtg ccagactcaa tcctccaccc      420
agaaacaaac atcccatcct ctccaatgat aacaacaata ttagtcctgg cattgtaatg     480 tactttgag tttacttcgg agtggtaagt ccctttttct acggttgcag gatcagcaag      540
gtgctcaaga attttatccc taaactctgc aagcgttcca ttgttggcgc ttttttcacc      600
cagcccaaaa tcatatttgt ggctatcaaa ttttttctgt agttgcctcc gtgtgaagat      660
accactatca agaggactac tgagcattac ataaacaggt ttgactccag aatccgccgg      720
gaaaatcacg atcagatcgt ttaggtccag tagcattccc ggataggact ccgggccggt     780
```

```
cttcaacggt gtgagggccg ctccctcata taccggcacc ggcttcggta tgaccggagt    840
ggtactcgaa gggttctggt ttcctggagg actcgccggc gtccaagtca ggatcagtgg    900
cggcgcttct gcgaccgtag agggaaccgt aacctcgtac agtcctgttg cggcgttata    960
ggccccatcc ggaccggaac gctttcggaa cgctcacacc atcggtctga ccaccgaaag   1020
gtcgtcgtgt tgcctcgcgc ctcgttggtc aggcgcatcg gcagatcgac ggtaccgctg   1080
gcttttgcaa ccgcgttcag gtttacgctt ggggaagcc ccaatttagc ggcatccatg    1140
cccagggcgt aacgaacgct atcgggcgtt tggtcctgcc attgctcggc agtccgggag   1200
agtaggtcag actggcaagc cacgccatc accgaggtgc tgaagccagg accgccagga    1260
cggcaatcgc atcggagatc gcttgagcaa gggatgcggc gcctgtgcga cctggatcag   1320
accccgctgc ggcggtggcg cacccgctgc cattggctgg catggcataa gtattggcag   1380
ccctgatcgc cgcttgacga gcgatttcct tgcgccttgc cgtttcggcg ttcagcttgt   1440
ccagccgtgt ttgcaggctg gcgatttcat ccactaggta ggacatcggc gttgtaggtt   1500
gccttttgtt tctccagtgc attgggtgcc ttggcaatca aggcattgtt tgcagtctgc   1560
aattcttctt attgcgatcg cctgcgtaag gagttgagta gcgcgttcaa gccactgctc   1620
tggcgttgga ttggtcagtt gaggcaaagc attcccagcc tggtcaagct cggactgcac   1680
tttttctcg acatttgcct tcctggcctt gtagtccgcc tccacctcag cagcggctcg    1740
ctgggcttct gcttccaatg accgggcttt attctccagc tcttgagacg tttgtttcaa   1800
gatagcgatt tgcgccttat agatatcggc gctgtacgct ttggccagct cactcatatg   1860
gcgatccagg aactctccat agaattttcg gctggccagc aactgactct ggtacatcga   1920
ctctgacttc tgaggaaagt ctgaagccgt ataagattg gccgggcgat cctcaatgac    1980
ctttagcgat tttgctttgg catccatgag tgcatcaacg atactctttt catcgcggat   2040
gtcattggca ctgaccgctt tacctggcaa ccccgcttca ctcttgagtt catcaacctc   2100
cttcagggtt tcatttttca ggttttctt gagttctgaa tgggacttat caagcgtact    2160
tcttagcttc ctgtactcct gcattccagt accgacatac ggacttggtc ctggtgggac   2220
aaatggtgga gtaccgtagc ttgatcgagc aggaatatac tggattatgt cacgcccacc   2280
accctgcaca tgtgtaataa ccatcgaacc aggttcgtaa tcattgacag ccatagatcg   2340
cccctacatt aatttgaaag tgtaatgtat tgagcgactc ccacctagag aaccctctcc   2400
cagtcaataa gccccaatgc atcggcaata cactgcaatc aacttcaata tcccgtgttt   2460
agatgatcca gaaggtgcgc tctctcgcct cttataatcg cgcctgcgtc aaacggtcat   2520
ttccttaacg cacacctcat ctaccccggc cagtcacgga agccgcatac cttcggttca   2580
ttaacgaact cccactttca aaattcatcc atgccgcccc ttcgcgagct ccggacaaa    2640
gccacgctga ttgcgagccc agcgttttg attgcaagcc gctgcagctg gtcaggccgt    2700
ttccgcaacg cttgaagtcc tggccgatat accggcaggg ccagccatcg ttcgacgaat   2760
aaagccacct cagccatgat gccctttcca tccccagcgg aaccccgaca tggacgccaa   2820
agccctgctc ctcggcagcc tctgcctggc cgccccattc gccgacgcgg cgacgctcga   2880
caatgctctc tccgcctgcc tcgccgcccg gctcggtgca ccgcacacgg cggagggcca   2940
gttgcacctg ccactcaccc ttgagggccg gcgctccacc ggcgaatgcg gctgtacctc   3000
ggcgctggtg cgatatcggc tgctggccag gggcgccagc ccgacagcc tcgtgcttca    3060
agagggctgc tcgatagtcg ccaggacacg ccgcgcacgc tgaccctggc ggcggacgcc   3120
ggcttggcga gcggccgcga actggtcgtc accctgggtt gtcaggcgcc tgactgacag   3180
```

```
gccgggctgc caccaccagg ccgagatgga cgccctgcat gtatcctccg atcggcaagc   3240
ctcccgttcg cacattcacc actctgcaat ccagttcata atcccataaa agccctctt    3300 ccgctccccg ccagcctccc cgcatcccgc acctagacg ccccgccgct tccgccggc     3360 tcgcccgaca agaaaaacca accgctcgat cagcctcatc cttcacccat cacaggagcc   3420
atcgcgatgc acctgatacc ccattggatc c                                 3451

<210> SEQ ID NO 19
<211> LENGTH: 744
<212> TYPE: DNA
<213> ORGANISM: Pseudomonas aeruginosa

<400> SEQUENCE: 19
gggttcagca agcgttcagg ggcggttcag taccctgtcc gtactctgca agccgtgaac    60
gacacgactc tcgcagaacg gagaaacacc atgaaagcac tcaagactct cttcatcgcc   120
accgccctgc tgggttccgc cgccggcgtc caggccgccg acaacttcgt cggcctgacc   180
tggggcgaga ccagcaacaa catccagaaa tccaagtcgc tgaaccgcaa cctgaacagc   240
ccgaacctcg acaaggtgat cgacaacacc ggcacctggg gcatccgcgc cggccagcag   300
ttcgagcagg gccgctacta cgcgacctac gagaacatct ccgacaccag cagcggcaac   360
aagctgcgcc agcagaacct gctcggcagc tacgacgcct tcctgccgat cggcgacaac   420
aacaccaagc tgttcggcgg tgccaccctc ggcctggtca agctggaaca ggacggcaag   480
ggcttcaagc gcgacagcga tgtcggctac gctgccgggc tgcaggccgg tatcctgcag   540
gagctgagca agaatgcctc gatcgaaggc ggctatcgtt acctgcgcac caacgccagc   600
accgagatga ccccgcatgg cggcaacaag ctgggctccc tggacctgca cagcagctcg   660
caattctacc tgggcgccaa ctacaagttc taaatgaccg cgcagcgccc gcgagggcat   720
gcttcgatgg ccgggccgga aggt                                          744

<210> SEQ ID NO 20
<211> LENGTH: 2760
<212> TYPE: DNA
<213> ORGANISM: Pseudomonas aeruginosa

<400> SEQUENCE: 20
ctgcagctgg tcaggccgtt ccgcaacgc ttgaagtcct ggccgatata ccggcagggc     60
cagccatcgt tcgacgaata aagccacctc agccatgatg ccctttccat ccccagcgga   120
accccgacat ggacgccaaa gcctgctcc tcggcagcct ctgcctggcc gccccattcg    180
ccgacgcggc gacgctcgac aatgctctct ccgcctgcct cgccgcccgg ctcggtgcac   240
cgcacacggc ggagggccag ttgcacctgc cactcaccct tgaggccggg cgctccaccg   300
gcgaatgcgg ctgtacctcg gcgctggtgc gatatcggct gctggccagg ggcgccagcg   360
ccgacagcct cgtgcttcaa gagggctgct cgatagtcgc caggacacgc gcgcacgct    420 gaccctggcg gcggacgccg gcttggcgag cggccgcgaa ctggtcgtca ccctgggttg   480
tcaggcgcct gactgacagg ccgggctgcc accaccaggc cgagatggac gccctgcatg   540
tatcctccga tcggcaagcc tcccgttcgc acattcacca ctctgcaatc cagttcataa   600
atcccataaa agccctcttc cgctccccgc cagcctcccc gcatcccgca cctagacgc    660 ccgccgctc tccgccggct cgcccgacaa gaaaaaccaa ccgctcgatc agcctcatcc   720
ttcacccatc acaggagcca tcgcgatgca cctgataccc cattggatcc cctggtcgc   780 cagcctcggc ctgctcgccg gcggctcgtc cgcgtccgcc gccgaggaag ccttcgacct   840
```

```
ctggaacgaa tgcgccaaag cctgcgtgct cgacctcaag gacggcgtgc gttccagccg    900
catgagcgtc gacccggcca tcgccgacac caacggccag ggcgtgctgc actactccat    960
ggtcctggag gcggcaacg acgcgctcaa gctggccatc gacaacgccc tcagcatcac   1020
cagcgacggc ctgaccatcc gcctcgaagg cggcgtcgag ccgaacaagc cggtgcgcta   1080
cagctacacg cgccaggcgc gcggcagttg gtcgctgaac tggctggtac cgatcggcca   1140
cgagaagccc tcgaacatca aggtgttcat ccacgaactg aacgccggca accagctcag   1200
ccacatgtcg ccgatctaca ccatcgagat gggcgacgag ttgctggcga agctggcgcg   1260
cgatgccacc ttcttcgtca gggcgcacga gagcaacgag atgcagccga cgctcgccat   1320
cagccatgcc ggggtcagcg tggtcatggc ccagacccag ccgcgccggg aaaagcgctg   1380
gagcgaatgg ccagcggca aggtgttgtg cctgctcgac ccgctggacg gggtctacaa   1440
ctacctcgcc cagcaacgct gcaacctcga cgatacctgg gaaggcaaga tctaccgggt   1500
gctcgccgga aacccggcga agcatgacct ggacatcaaa cccacggtca tcagtcatcg   1560
cctgcacttt cccgagggcg gcagcctggc cgcgctgacc gcgcaccagg cttgccacct   1620
gccgctggag actttcaccc gtcatcgcca gccgcgcggc tgggaacaac tggagcagtg   1680
cggctatccg gtgcagcggc tggtcgccct ctacctggcg gcgcggctgt cgtggaacca   1740
ggtcgaccag gtgatccgca acgccctggc cagccccggc agcggcggcg acctgggcga   1800
agcgatccgc gagcagccgg agcaggcccg tctggccctg accctggccg ccgccgagag   1860
cgagcgcttc gtccggcagg gcaccggcaa cgacgaggcc ggcgcggcca cgccgacgt   1920 ggtgagcctg acctgcccgg tcgccgccgg tgaatgcgcg ggcccggcgg acagcggcga   1980
cgccctgctg gagcgcaact atcccactgg cgcggagttc ctcggcgacg gcggcgacgt   2040
cagcttcagc cccgcggca cgcagaactg gacggtggag cggctgctcc aggcgcaccg   2100
ccaactggag gagcgcggct atgtgttcgt cggctaccac ggcaccttcc tcgaagcggc   2160
gcaaagcatc gtcttcggcg gggtgcgcgc gcgcagccag gacctcgacg cgatctggcg   2220
cggtttctat atcgccggcg atccggcgct ggcctacggc tacgcccagg accaggaacc   2280
cgacgcacgc ggccggatcc gcaacggtgc cctgctgcgg gtctatgtgc cgcgctcgag   2340
cctgccgggc ttctaccgca ccagcctgac cctggccgcg ccggaggcgg cgggcgaggt   2400
cgaacggctg atcggccatc cgctgccgct gcgcctggac gccatcaccg gccccgagga   2460
ggaaggcggg cgcctggaga ccattctcgg ctggccgctg gccgagcgca ccgtggtgat   2520
tccctcggcg atccccaccg acccgcgcaa cgtcggcggc gacctcgacc cgtccagcat   2580
ccccgacaag gaacaggcga tcagcgcct gccggactac gccagccagc ccggcaaacc   2640
gccgcgcgag gacctgaagt aactgccgcg accggccggc tcccttcgca ggagccggcc   2700
ttctcggggc ctggccatac atcaggtttt cctgatgcca gcccaatcga atatgaattc   2760

<210> SEQ ID NO 21
<211> LENGTH: 172
<212> TYPE: DNA
<213> ORGANISM: Staphylococcus saprophyticus

<400> SEQUENCE: 21
ttgatgaaat gcatcgatta ataaattttc atgtacgatt aaaacgtttt taccttacc      60 ttttcgtact acctctgcct gaagttgacc acctttaaag tgattcgttg aaatccatta    120
tgctcattat taatacgatc tataaaaaca aatggaatgt gatgatcgat ga           172

<210> SEQ ID NO 22
```

```
<211> LENGTH: 155
<212> TYPE: DNA
<213> ORGANISM: Staphylococcus saprophyticus

<400> SEQUENCE: 22
gttccattga ctctgtatca cctgttgtaa cgaacatcca tatgtcctga aactccaacc      60
acaggtttga ccacttccaa tttcagacca ccaagtttga cacgtgaaga ttcatcttct     120
aatatttcgg aattaatatc atattattta aatag                                155

<210> SEQ ID NO 23
<211> LENGTH: 145
<212> TYPE: DNA
<213> ORGANISM: Staphylococcus saprophyticus

<400> SEQUENCE: 23
acatagaaaa actcaaaaga tttacttttt tcaaatggaa aataagggta cacacgatat      60
ttcccgtcat cttcagttac cggtacaaca tcctctttat taacctgcac ataatctgac     120
tccgcttcac tcatcaaact actaa                                           145

<210> SEQ ID NO 24
<211> LENGTH: 266
<212> TYPE: DNA
<213> ORGANISM: Staphylococcus saprophyticus

<400> SEQUENCE: 24
tttcactgga attacatttc gctcattacg tacagtgaca atcgcgtcag atagtttctt      60
ctggttagct tgactcttaa caatcttgtc taaattttgt ttaattcttt gattcgtact     120
agaaatttta cttctaattc cttgtaattc ataacttgca ttatcatata aatcataagt     180
atcacatttt tgatgaatac tttgatataa atctgacaat acaggcagtt gctccattct     240
atcgttaaga atagggtaat taatag                                          266

<210> SEQ ID NO 25
<211> LENGTH: 845
<212> TYPE: DNA
<213> ORGANISM: Haemophilus influenzae

<400> SEQUENCE: 25
tgttaaattt ctttaacagg gattttgtta tttaaattaa acctattatt ttgtcgcttc      60
tttcactgca tctactgctt gagttgcttt ttctgaaacc gcctctttca tttcacttgc     120
tttttctgat gctgcttctt tcatttcgcc tactttttct gacgctgctt ctgttgctga     180
tttaattact tctttcgcat cttccacttt ctctgctact ttattttttca cgtctgtaga    240 aagctgctgt gcttttttcct ttacttcagt cattgtatta gctgcagcat cttttgtttc    300
tgatgcgact gatgctacag tttgcttcgt atcctcaact ttttgttttg cttcttgctt    360
atcaaaacaa cctgtcacga ctaaagctga acctaaaacc aatgctaatg ttaatttttt    420
cattattttc tccatagaat aatttgattg ttacaaagcc ctattacttt gatgcagttt     480
agtttacggg aattttcata aaagaaaaa cagtaatagt aaaactttac cttctcttaa      540
aaagattact ttataaaaaa acatctaaga tattgatttt taatagatta taaaaaacca    600
ataaaaattt tatttttttgt aaaaaaaaag aatagtttat tttaaataaa ttacaggaga    660
tgcttgatgc atcaatattt ctgatttatt accatcccat aataattgag caatagttgc    720
aggataaaat gatattggat ttcgttttcc atacagttca gcaacaattt ctcccactaa    780
gggcaaatgg gaaacaatta atacagattt aacgccctcg tcttttagca cttctaaata    840
```

```
atcaa                                                                845
```

<210> SEQ ID NO 26
<211> LENGTH: 1598
<212> TYPE: DNA
<213> ORGANISM: Haemophilus influenzae
<400> SEQUENCE: 26

```
gaatagagtt gcactcaata gattcgggct ttataattgc ccagatttt atttataaca       60
aagggttcca aatgaaaaaa tttaatcaat ctctattagc aactgcaatg ttgttggctg     120
caggtggtgc aaatgcggca gcgtttcaat tggcggaagt ttctacttca ggtcttggtc     180
gtgcctatgc gggtgaagcg gcgattgcag ataatgcttc tgtcgtggca actaacccag     240
ctttgatgag tttatttaaa acggcacagt tttccacagg tggcgtttat attgattcta     300
gaattaatat gaatggtgat gtaacttctt atgctcagat aataacaaat cagattggaa     360
tgaaagcaat aaaggacggc tcagcttcac agcgtaatgt tgttcccggt gcttttgtgc     420
caaatcttta tttcgttgcg ccagtgaatg ataaattcgc gctgggtgct ggaatgaatg     480
tcaatttcgg tctaaaaagt gaatatgacg atagttatga tgctggtgta tttggtggaa     540
aaactgactt gagtgctatc aacttaaatt taagtggtgc ttatcgagta acagaaggtt     600
tgagcctagg tttaggggta aatgcggttt atgctaaagc ccaagttgaa cggaatgctg     660
gtcttattgc ggatagtgtt aaggataacc aaataacaag cgcactctca acacagcaag     720
aaccattcag agatcttaag aagtatttgc cctctaagga caaatctgtt gtgtcattac     780
aagatagagc cgcttggggc tttggctgga atgcaggtgt aatgtatcaa tttaatgaag     840
ctaacagaat tggtttagcc tatcattcta aagtggacat tgattttgct gaccgcactg     900
ctactagttt agaagcaaat gtcatcaaag aaggtaaaaa aggtaattta acctttacat     960
tgccagatta cttagaactt tctggttttc atcaattaac tgacaaactt gcagtgcatt    1020
atagttataa atatacccat tggagtcgtt taacaaaatt acatgccagc ttcgaagatg    1080
gtaaaaaagc ttttgataaa gaattacaat acagtaataa ctctcgtgtt gcattagggg    1140
caagttataa tctttatgaa aaattgacct tacgtgcggg tattgcttac gatcaagcgg    1200
catctcgtca tcaccgtagt gctgcaattc cagataccga tcgcacttgg tatagtttag    1260
gtgcaaccta taaattcacg ccgaattat ctgttgatct tggctatgct tacttaaaag    1320
gcaaaaaagt tcacttttaaa gaagtaaaaa caataggtga caaacgtaca ttgacattga    1380
atacaactgc aaattatact tctcaagcac acgcaaatct ttacgtttg aatttaaatt    1440
atagtttcta atccgttaaa aaatttagca taataaagca caattccaca ctaagtgtgc    1500
ttttcttta taaacaagg cgaaaaatga ccgcacttta ttacattat taccctcgc    1560
cagtcggacg gcttttgatt ttatctgacg gcgaaaca                             1598
```

<210> SEQ ID NO 27
<211> LENGTH: 9100
<212> TYPE: DNA
<213> ORGANISM: Haemophilus influenzae
<400> SEQUENCE: 27

```
gtcaaaaatt gcgtgcattc tagcgaaaaa atgggctttt gggaactgtg ggatttattt       60
aaaatcttag aaaatcttac cgcactttta agctataaag tgcggtgaaa tttagtggcg     120
tttataatgg agaattactc tggtgtaatc cattcgactg tccagcttcc agtaccttct     180
ggaactaatg ttttttgtgag ataaggcaaa atttctttca tttgggtttc taatgtccaa     240
```

```
ggtggattaa ttaccaccat accgctcgca gtcattcctc gttgatcgct atctgggcga    300
acggcgagtt caattttag aatttttcta attcccgttg cttctaaacc cttaaaata     360
cgtttagttt gttggcgtaa tacaacagga taccaaatcg cataagtgcc agtggcaaaa   420
cgtttatagc cctcttcaat ggctttaaca acgagatcat aatcatcttt taattcataa   480
ggcggatcga tgagtactaa gcctcggcgt tcttttggcg aagcgttgc tttgacttgt    540
tgaaagccat tgtcacattt tacggtgaca ttttttgtcgt cgctaaaatt attgcgaaga  600
attggataat cgctaggatg aagctcggtc aatagtgcgc gatcttgtga gcgcaacaat   660
tccgcggcaa ttaatggaga acccgcgtaa taacgtagtt ctttgccacc ataattgagt   720
ttttttgatca ttttacata acgagcaata tcttcgggta aatctgtttg atcccacagg   780
cgtccaatac cttctttata ttccccgtt tttttctgatt catttgagga taaacgataa   840
cgccccacac cagagtgcgt atccaaataa aaaagcctt tttctttgag tttaagattt    900
tccaaaatga gcattaaaac aatatgtttc aagacatcgg catgattgcc agcgtgaaat   960
gagtgatgat aactcagcat aatatattcc ttatatattc cttatttgtt taataacgaa  1020
ggcgagccaa ttgactcgcc cgattacaca ctaaagtgcg gtcatttta gaagagttct   1080
tgtggttgcg tcgctggcgt attgccttca ttatttaagc gttgctgtaa ctcagtagga  1140
acataataac cacgctcttg catttccgaa agataggtac gtgtcggttc tgttcccgca  1200
ataaaatatt ctttgcgccc accgtttgga gaaagcaaac ctgtcaaagt atcaatgttt  1260
ttttccacaa tttttggcgg tagcgacaat ttacgttctg gcttatcact caaagccgtt  1320
ttcatataag tgatccaagc aggcattgct gttttttgctc ctgcttctcc acgcccaagt 1380
actcgtttgt tatcatcaaa cccgacataa gttgtggtta ctaagtttgc accaaatccc  1440
gcataccaag ccactttga actgttggta gtacctgttt taccgcctat atcgctacgt   1500
ttaatgcttt gtgcaatacg ccagctggtg cctttccagt ctaaaccttg ttcgccataa  1560
attgccgtat ttaaggcact acgaatgaga aaagcaagtt cgccactaat gacacgtggc  1620
gcatattcta ttttcgacga agcattttt gcagcagcca ttaaatcaat cgcatcttct   1680
ttaagtgcgg tcatatttga ttgtaattct ggcagttcag gcacagtttc aggttgttga  1740
tctaattctt cgccattggt gctgtcatct gttggttta aggcattctc gcctaaagga   1800
atattggcaa agccgttgat tttgtctttg gtttcgccat aaattacagg tatatcatta  1860
cattcaatgc aagcaatttt agggtttgca ataaataagt ctttacccgt gttatcttga  1920
atttttcaa tgatataagg ttcaatgagg aagccaccat tatcaaacac cgcataagct   1980
cgcgccattt ctaatggtgt gaaagaggct gcgccaagtg ctaaggcttc actggcaaaa  2040
tattgatcac gttaaaacc aaaacgttgt aaaaattctg ctgtgaaatc aatacctgcc   2100
gtttggatag cacgaatagc aattatattt ttggattgac ctaatcctac gcgtaaacgc  2160
atcgggccat cataacgatc aggcgagttt tcggttgcc acatttttg tcccggtttt    2220
tgaatagaaa tcgggctgtc ttgtaatacg cttgaaagtg ttaagccttt ttctaatgct  2280
gccgcgtaaa taaatggttt gatagaagaa cccacttgaa ctaaagactg tgtggctcga  2340
ttgaatttac tttgttcata gctaaagcca ccgaccactg cttcaatcgc accattatct  2400
gaattaagag aaactaatgc tgaatttgct gcgggaattt gtcctaattg ccattcccca  2460
ttagcacgct gatgaatcca aatttgctcg ccgactttca caggattgct tctgcctgtc  2520
caacgcattg cattggttga taaggtcatt ttttccccag aagcgagcaa tatatcagca  2580
ccgcctttta caattccaat cactgccgca ggaataaatg gctctgaatc aggtagtttg  2640
```

```
cgtagaaaac cgacaatgcg atcattgtcc caagcggctt cattttttg ccataatggc      2700 gcgccaccgc gataaccgtg acgcatatcg taatcaatca agttattacg cacagctttt      2760
tgggcttcag cttggtcttt tgaaagtaca gtggtaaata ctttataacc actggtgtaa      2820
gcattttctt cgccaaaacg acgcaccatt tcttgacgca ccatttcagt gacataatcg      2880
gctcgaaatt caaattttgc gccgtgatag ctcgccacaa tcggctcttt caatgcagca      2940
tcatattctt ctttgctgat gtattttca tctaacatac ggcttagcac cacattgcgg       3000
cgttcttctg aacgttttaa agaataaagc gggttcattg ttgaaggtgc tttaggtaaa      3060
ccagcaataa tcgccatttc cgataaggtc aattcattca atgatttacc gaaataggtt      3120
tgtgctgccg ctgcaacacc ataagaacga tagcctaaaa agattttgtt taaataaagc      3180
tctaatattt cttgtttgtt gagagtattt tcgatttcta ccgcaagcac ggcttcacga      3240
gctttacgaa taatggtttt ttctgaggtt aagaaaaagt tacgcgctaa ttgttgagta      3300
atcgtacttg cgccttgtga tgcaccgcca ttactcactg cgacaaacaa tgcacgggca      3360
atgccgatag ggtctaatcc gtgatgatcg taaaaacgac tgtcttccgt cgctaaaaat      3420
gcgtcaatta agcgttgtgg cacatcggct aatttcactg gaatacggcg ttgctcaccc      3480
acttcgccaa ttaatttacc gtcagccgta taaatctgca ttggttgctg taattcaacg      3540
gtttttaatg tttctactga gggcaattca gattttaagt ggaaatacaa cattccgcct      3600
gctactaaac ctaaaataca taagttaat agggtgttta atattaattt tgcgatccgc       3660
atcgtaaaat tctcgcttcg ttaatgaata ttcttgtcaa gagacctatg atttggctgt      3720
taagtataaa agattcagcc tttaaagaat aggaaagaat atgcaattct ccctgaaaaa      3780
ttaccgcact ttacaaatcg gcattcatcg taagcgagt tattttgatt ttgtgtggtt       3840
tgatgatctc gaacagccac aaagttatca aatctttgtt aatgatcgtt attttaaaaa      3900
tcgtttttta caacagctaa aaacacaata tcaagggaaa acctttcctt tgcagttttgt     3960 agcaagcatt cccgcccact taacttggtc gaaagtatta atgttgccac aagtgttaaa      4020
tgcgcaagaa tgtcatcaac aatgtaaatt tgtgattgaa aaagagctgc ctattttttt      4080
agaagaattg tggtttgatt atcgttctac cccgttaaag caaggttttc gattagaggt      4140
tactgcaatt cgtaaaagta gcgctcaaac ttatttgcaa gatttcagc catttaatat       4200 taatatattg gatgttgcgt caaatgctgt tttgcgtgca tttcaatatc tgttgaatga      4260
acaagtgcgg tcagaaaata ccttattttt atttcaagaa gatgactatt gcttggcgat      4320
ttgtgaaaga tctcagcaat cacaaatttt acaatctcac gaaaatttga ccgcacttta      4380
tgaacaattt accgaacgtt ttgaaggaca acttgaacaa gtttttgttt atcaaattcc      4440
ctcaagtcat acaccattac ccgaaaactg gcagcgagta gaaacagaac tcccttttat     4500
tgcgctgggc aacgcgctat ggcaaaaaga tttacatcaa caaaaagtgg gtggtaaaat     4560
gtcgatgaat ttattgcctt ggcgtactta tcaacatcaa aagcgtttac gtcgtttagc      4620
tttttatatc gctttattta tcttgcttgc tattaattta atgttggctt ttagcaattt     4680
gattgaacaa cagaaacaaa atttgcaggc acagcaaaag tcgtttgaac aacttaatca      4740
acagcttcat aaaactacca tgcaaattga tcagttacgc attgcggtga agttggtga      4800 agttttgaca tctattccca acgagcaagt aaaaaagagt ttacaacagc taagtgaatt      4860
accttttcaa caaggagaac tgaataaaatt taaacaagat gccaataact taagcttgga      4920
aggtaacgcg caagatcaaa cagaatttga actgattcat caattttaa agaaacattt      4980 tcccaatgtg aaattaagtc aggttcaacc tgaacaagat acattgtttt ttcactttga      5040
```

```
tgtggaacaa ggggcggaaa aatgaaagct ttttttaacg atccttttac tccttttgga      5100
aaatggctaa gtcagccttt ttatgtgcac ggtttaacct ttttattgct attaagtgcg      5160
gtgattttc gccccgtttt agattatata gagggagtt cacgtttcca tgaaattgaa       5220
aatgagttag cggtgaaacg ttcagaattg ttgcatcaac agaaaatttt aacctcttta      5280
caacagcagt cggaaagtcg aaaactttct ccagaactgg ctgcacaaat tattcctttg      5340
aataaacaaa ttcaacgttt agctgcgcgt aacggtttat ctcagcattt acgttgggaa      5400
atggggcaaa agcctatttt gcatttacag cttacaggtc attttgaaaa aacgaagaca      5460
ttttttatccg cacttttggc taattcgtca cagcttctg taagtcggtt gcaatttatg      5520
aaacccgaag acggcccatt gcaaaccgag atcatttttc agctagataa ggaaacaaaa      5580
tgaaacattg ttttttcctg attatattat ttttatgaa ttgcagttgg ggacaagatc      5640
ctttcgataa acacagcgt aaccgttctc agtttgataa cgcacaaaca gtaatggagc      5700
aaacagaaat aatttcctca gatgtgccta ataatctatg cggagcggat gaaaatcgcc      5760
aagcggctga aattcctttg aacgctttaa aattggtggg ggtagtgatt tctaaagata      5820
aagcctttgc cttgttgcaa gatcaaggtt tgcaagttta cagcgtttta gagggcgttg      5880
atgtggctca agagggctat attgtagaaa aaatcaacca aaacaatgtt caatttatgc      5940
gtaagctagg agagcaatgt gatagtagtg aatggaaaaa attaagtttt taaggaaga      6000
ttatgaagaa atatttttta aagtgcggtt attttttagt atgttttgt ttgccattaa      6060
tcgttttgc taatcctaaa acagataacg aacgtttttt tattcgttta tcgcaagcac      6120
ctttagctca aacactggag caattagctt ttcaacaaga tgtgaattta gtgattggag      6180
atatattgga aaacaagatc tctttgaaat taaacaatat tgatatgcca cgtttgctac      6240
aaataatcgc aaaagtaag catcttactt tgaataaga tgatgggatt tattatttaa      6300
acggcagtca atctggcaaa ggtcaggttg caggaaatct tacgacaaat gaaccgcact      6360
tagtgagtca cacggtaaaa ctccattttg ctaaagcttc tgaattaatg aaatccttaa      6420
caacaggaag tggctctttg ctttctcccg ctgggagcat tacctttgat gatcgcagta      6480
atttgctggt tattcaggat gaacctcgtt ctgtgcaaaa tatcaaaaaa ctgattgctg      6540
aaatggataa gcctattgaa cagatcgcta ttgaagcgcg aattgtgaca attacggatg      6600
agagtttgaa agaacttggc gttcggtggg ggattttaa tccaactgaa aatgcaagac      6660
gagttgcggg cagccttaca ggcaatagct ttgaaaatat tgcggataat cttaatgtaa      6720
attttgcgac aacgacgaca cctgctggct ctatagcatt acaagtcgcc aaaattaatg      6780
ggcgattgct tgatttagaa ttgagtgcgt tggagcgtga aataatgta gaaattattg      6840
caagccctcg cttactcact accaataaga aaagtgcgag cattaaacag gggacagaaa      6900
ttccttacat cgtgagtaat actcgtaacg atacgcaatc tgtggaattt cgtgaggcgg      6960
tgcttggttt ggaagtgacg ccacatattt ctaaagataa caatatctta cttgatttat      7020
tggtaagtca aaattcccct ggttctcgtg tcgcttatgg acaaaatgag gtggtttcta      7080
ttgataaaca agaaattaat actcaggttt ttgccaaaga tgggaaaacc attgtgcttg      7140
gcggcgtatt tcacgataca atcacgaaaa gcgaagataa agtgccattg cttggcgata      7200
tacccgttat taaacgatta tttagcaaag aaagtgaacg acatcaaaaa cgtgagctag      7260
tgattttcgt cacgccacat attttaaaag caggagaaaa cgttagaggc gttgaaacaa      7320
aaaagtgagg gtaaaaaata acttttttaaa tgatgaattt ttttaatttt cgctgtatcc      7380
actgtcgtgg caatcttcat atcgcaaaaa atgggttatg ttcaggttgc caaaaacaaa      7440
```

-continued

```
ttaaatctttt tccttattgc ggtcattgtg gttcggaatt gcaatattat gcgcagcatt     7500
gtgggaattg tcttaaacaa gaaccaagtt gggataagat ggtcattatt gggcattata     7560
ttgaacctct ttcgatattg attcagcgtt ttaaatttca aaatcaattt tggattgacc     7620
gcactttagc tcggctttta tatcttgcgg tacgtgatgc taaacgaacg catcaactta     7680
aattgccaga ggcaatcatt ccagtgcctt tatatcattt tcgtcagtgg cgacggggtt     7740
ataatcaggc agatttatta tctcagcaat taagtcgttg gctggatatt cctaatttga     7800
acaatatcgt aaagcgtgtg aaacacacct atactcaacg tggtttgagt gcaaaagatc     7860
gtcgtcagaa tttaaaaaat gccttttctc ttgctgtttc gaaaaatgaa tttccttatc     7920
gtcgtgttgc gttggtggat gatgtgatta ctactggttc tacactcaat gaaatctcaa     7980
aattgttgcg aaaattaggt gtggaggaga ttcaagtgtg ggggctggca cgagcttaat     8040
ataaagcact ggaaaaaaaa gcgcgataag cgtattattc ccgatacttt ctctcaagta     8100
tttaggacat aattatggaa caagcaaccc agcaaatcgc tatttctgat gccgcacaag     8160
cgcattttcg aaaacttta gacacccaag aagaaggaac gcatattcgt attttcgcgg     8220
ttaatcctgg tacgcctaat gcggaatgtg gcgtatctta ttgccccccg aatgccgtgg     8280
aagaaagcga tattgaaatg aaatataata cttttctgc atttattgat gaagtgagtt     8340
tgcctttctt agaagaagca gaaattgatt atgttaccga agagcttggt gcgcaactga     8400
ccttaaaagc accgaatgcc aaaatgcgta aggtggctga tgatgcgcca ttgattgaac     8460
gtgttgaata tgtaattcaa actcaaatta cccacagct tgcaaatcac ggtggacgta     8520
taaccttaat tgaaattact gaagatggtt acgcagtttt acaatttggt ggtggctgta     8580
acggttgttc aatggtggat gttacgttaa aagatggggt agaaaaacaa cttgttagct     8640
tattcccgaa tgaattaaaa ggtgcaaaag atataactga gcatcaacgt ggcgaacatt     8700
cttattatta gtgagttata aaagaagatt tataatgacc gcactttga aagtgcggtt     8760
atttttatgg agaaaaaatg aaaatacttc aacaagatga ttttggttat tggttgctta     8820
cacaaggttc taatctgtat ttagtgaata atgaattgcc ttttggtatc gctaaagata     8880
ttgatttgga aggattgcag gcaatgcaaa ttggggaatg gaaaaattat ccgttgtggc     8940
ttgtggctga gcaagaaagt gatgaacgag aatatgtgag tttgagtaac ttgctttcac     9000
tgccagagga tgaattccat atattaagcc gaggtgtgga aattaatcat tttctgaaaa     9060
cccataaatt ctgtggaaag tgcggtcata aaacacaaca                           9100
```

<210> SEQ ID NO 28
<211> LENGTH: 525
<212> TYPE: DNA
<213> ORGANISM: Moraxella catarrhalis

<400> SEQUENCE: 28

```
aaaaatcgac tgccgtcatt ttcaaccacc acatagctca tattcgcaag ccaatgtatt      60
gaccgttggg aataataaca gccccaaaac aatgaaacat atggtgatga ccaaacata     120
ctttcctgca gattttggaa tcatatcgcc atcagcacca gtatggtttg accagtattt     180
aacgccatag acatgtgtaa aaaaattaaa taacggtgca agcatgagac caacggcacc     240
tgatgtacct tgtacgatga cctcacctgc tgtggcaacc ataccaagtc cattgcctgt     300
gatattttg cgaaaagaca aacttaccac acagaccaag ccgatgattg agatgacaaa     360
ataaaaccaa tccaaatgcg tgtgagctgt tgtggtccaa aatccagtaa atagtgcaat     420
aaatccgcaa acaaaccaaa gtagcaccca gcttgttgtc caatcttttt taccaaagcc     480
```

```
tgtgatgtta tctaaaatat caattttcat cagattttcc ctaat              525
```

<210> SEQ ID NO 29
<211> LENGTH: 466
<212> TYPE: DNA
<213> ORGANISM: Moraxella catarrhalis

<400> SEQUENCE: 29

```
taatgataac cagtcaagca agctcaaatc agggtcagcc tgttttgagc ttttatttt    60
ttgatcatca tgcttaagat tcactctgcc attttttac aacctgcacc acaagtcatc   120
atcgcatttg caaaaatggt acaaacaagc cgtcagcgac ttaaacaaaa aaaggctcaa   180
tctgcgtgtg tgcgttcact tttacaaatc accatgcacc gctttgacat tgttggtgaa   240
tttcatgacc atgcacaccc ttattatatt aactcaaata aaatacgcta ctttgtcagc   300
tttagccatt cagataatca agtcgctctc atcatcagct taacaccttg tgccattgac   360
atagaagtta acgatattaa atacagtgtg gttgaacgat actttcatcc caatgaaatt   420
tatctactta ctcaatttag ctctactgat aggcaacagc ttatta              466
```

<210> SEQ ID NO 30
<211> LENGTH: 631
<212> TYPE: DNA
<213> ORGANISM: Streptococcus pneumoniae

<400> SEQUENCE: 30

```
gatctttgat tttcattgag tattactctc tcttgtcact tctttctatt ttaccataaa    60
gtccagcctt tgaagaactt ttactagaag acaaggggct tctgtctcta tttgccatct   120
taggcatcaa aaaagagggg tcatccctct ttacgaattc aatgctacta gggtatccaa   180
atactggttg ttgatgactg ccaaaatata ggtatctgct ttcaagaggt catctggtcc   240
aaattcaaca tccaatgggg aattttcctg ctctcggaaa cccaaaatat tcagattgta   300
tttgccacgg aggtctaatt tacttcagac tttgacctgc caagactga ggaattttca   360
tctccacgat agacacattt ttatccaact gaaagacatc aacactatta tgaaaagaat   420
ggtctgtgct agagactgcc ccatttcata ctctggcgag ataaccgagt cagctccaat   480
cttttctagc actttcttag cggtctgact tttgacctta gcaataacag tcggtacccc   540
caaactctta cagtgcataa ccgcaagcac actcgactcc agattttcac ctgtcgcgac   600
tacaacggta tcgcaggtat caatccctgc t                        631
```

<210> SEQ ID NO 31
<211> LENGTH: 3754
<212> TYPE: DNA
<213> ORGANISM: Streptococcus pneumoniae

<400> SEQUENCE: 31

```
ccaatatttt ggtcagcata gtgttctttt tcagtggtaa cagcttgcaa tacttgagca    60
gaaatggcag atttatcaag gaaaaagtta acgtaaggtc ctgttgcgac aacttttttca   120
aaggcttggc tgttcatttt ttcagccagt tcagccgcaa tcatttgtgg tgctttacgt   180
tcgactttg caagagaaaa agcagggaaa gcaatgtctc ccatttctga gtttttaggg   240
gtttccagta actttaaaat agcctcttgg tccaggctat caatgatgct agataattcg   300
ctagcaatca attcttttgt attcattaag agctcctttt tggactttc tactatttta   360
tcacaatttt aaagaaagaa gaaaaaattt ttgaaatctc ctgttttttt ggtataatat   420
ggttataaat atagttataa atatagtat aaatatgcac gcaagaggat tttatgagaa   480
```

-continued

```
aaagagatcg tcatcagtta ataaaaaaaa tgattactga ggagaaatta agtacacaaa     540
aagaaattca agatcggttg gaggcgcaca atgtttgtgt gacgcagaca accttgtctc     600
gtgatttgcg cgaaatcggc ttgaccaagg tcaagaaaaa tgatatggtg tattatgtac     660
tagtaaatga gacagaaaag attgatttgg tggaattttt gtctcatcat ttagaaggtg     720
ttgcaagagc agagtttacc ttggtgcttc ataccaaatt gggagaagcc tctgttttgg     780
caaatattgt agatgtaaac aaggatgaat ggattttagg aacagttgct ggtgccaata     840
ccttattggt tatttgtcga gatcagcacg ttgccaaact catggaagat cgtttgctag     900
atttgatgaa agataagtaa ggtcttggga gttgctctca agacttattt ttgaaaagga     960
gagacagaaa atggcgatag aaaagctatc acccggcatg caacagtatg tggatattaa    1020
aaagcaatat ccagatgctt ttttgctctt tcggatgggt gattttatg aattatttta     1080 tgaggatgcg gtcaatgctg cgcagattct ggaaatttcc ttaacgagtc gcaacaagaa    1140
tgccgacaat ccgatcccta tggcgggtgt tccctatcat tctgcccaac agtatatcga    1200
tgtcttgatt gagcagggtt ataaggtggc tatcgcagag cagatggaag atcctaaaca    1260
agcagttggg gttgttaaac gagaggttgt tcaggtcatt acgccaggga cagtggtcga    1320
tagcagtaag ccggacagtc agaataattt tttggtttcc atagaccgcg aaggcaatca    1380
atttggccta gcttatatgg atttggtgac gggtgacttt tatgtgacag gtcttttgga    1440
tttcacgctg gtttgtgggg aaatccgtaa cctcaaggct cgagaagtgg tgttgggtta    1500
tgacttgtct gaggaagaag aacaaatcct cagccgccag atgaatctgg tactctctta    1560 tgaaaagaa agctttgaag accttcattt attggatttg cgattggcaa cggtggagca     1620
aacggcatct agtaagctgc tccagtatgt tcatcggact cagatgaggg aattgaacca    1680
cctcaaacct gttatccgct acgaaattaa ggatttcttg cagatggatt atgcgaccaa    1740
ggctagtctg gatttggttg agaatgctcg ctcaggtaag aaacaaggca gtcttttctg    1800
gcttttggat gaaaccaaaa cggctatggg gatgcgtctc ttgcgttctt ggattcatcg    1860 cccccttgatt gataaggaac gaatcgtcca acgtcaagaa gtagtgcagg tcttctctcga   1920 ccatttcttt gagcgtagtg acttgacaga cagtctcaag ggtgtttatg acattgagcg    1980
cttggctagt cgtgtttctt ttggcaaaac caatccaaag gatctcttgc agttggcgac    2040
taccttgtct agtgtgccac ggattcgtgc gattttagaa gggatggagc aacctactct    2100
agcctatctc atcgcacaac tggatgcaat ccctgagttg gagagtttga ttagcgcagc    2160
gattgctcct gaagctcctc atgtgattac agatggggga attatccgga ctggatttga    2220
tgagacttta gacaagtatc gttgcgttct cagagaaggg actagctgga ttgctgagat    2280
tgaggctaag gagcgagaaa actctggtat cagcacgctc aagattgact acaataaaaa    2340
ggatggctac tattttcatg tgaccaattc gcaactggga aatgtgccag cccacttttt    2400
ccgcaaggcg acgctgaaaa actcagaacg ctttggaacc gaagaattag cccgtatcga    2460
gggagatatg cttgaggcgc gtgagaagtc agccaacctc gaatacgaaa tatttatgcg    2520
cattcgtgaa gaggtcggca agtacatcca gcgtttacaa gctctagccc aaggaattgc    2580
gacggttgat gtcttacaga gtctggcggt tgtggctgaa acccagcatt tgattcgacc    2640
tgagtttggt gacgattcac aaattgatat ccggaaaggg cgccatgctg tcgttgaaaa    2700
ggttatgggg gctcagacct atattccaaa tacgattcag atggcagaag ataccagtat    2760
tcaattggtt acagggccaa acatgagtgg gaagtctacc tatatgcgtc agttagccat    2820
gacggcggtt atggcccagc tgggttccta tgttcctgct gaaagcgccc atttaccgat    2880
```

-continued

```
ttttgatgcg attttttaccc gtatcggagc agcagatgac ttggtttcgg gtcagtcaac    2940
ctttatggtg gagatgatgg aggccaataa tgccatttcg catgcgacca agaactctct    3000
cattctcttt gatgaattgg acgtggaac tgcaacttat gacgggatgg ctcttgctca    3060
gtccatcatc gaatatatcc atgagcacat cggagctaag accctctttg cgacccacta    3120
ccatgagttg actagtctgg agtctagttt acaacacttg gtcaatgtcc acgtggcaac    3180
tttggagcag gatgggcagg tcaccttcct tcacaagatt gaaccgggac cagctgataa    3240
atcctacggt atccatgttg ccaagattgc tggcttgcca gcagacccttt tagcaagggc    3300 ggataagatt ttgactcagc tagagaatca aggaacagag agtcctcctc ccatgagaca    3360
aactagtgct gtcactgaac agatttcact ctttgatagg gcagaagagc atcctatcct    3420
agcagaatta gctaaactgg atgtgtataa atgacacct atgcaggtta tgaatgtctt    3480
agtagagtta aaacagaaac tataaaacca agactcacta gttaatctag ctgtatcaag    3540
gagacttctt tgacaattct ccactttttt gctagaataa catcacacaa acagaatgaa    3600
aagggctgac gcattgtcgc tccctttgt ctatttttta aggagaaagt atgctgattc    3660
agaaaataaa aacctacaag tggcaggccc tgcttcgctc ctgatgacag gcttgatggt    3720
tgctagttca cttctgcaac cgcgttatct gcag                                3754
```

<210> SEQ ID NO 32
<211> LENGTH: 1337
<212> TYPE: DNA
<213> ORGANISM: Streptococcus pyogenes

<400> SEQUENCE: 32

```
aacaaaataa aagaacttac ctattttcca tccaaaatgt ttagcaatca tcatctgcaa     60
ggcaacgtat tgcatggcat tgatgtgatg agcaactaat atgtcattag aacgttgcgt    120
caaactagca tctaaataaa gatcgaaatg cagttatcaa aaatgcaagc tcctatcggc    180
ccttgtttta attattactc acattgcctt aatgtattta cttgcttatt attaacttttt    240 ttgctaagtt agtagcgtca gttattcatt gaaaggacat tattatgaaa attcttgtaa    300
caggctttga tcccttttggc ggcgaagcta ttaatcctgc ccttgaagct atcaagaaat    360
tgccagcaac cattcatgga gcagaaatca aatgtattga agttccaacg gttttttcaaa    420 aatctgccga tgtgctccag cagcatatcg aaagctttca acctgatgca gtcctttgta    480
ttgggcaagc tggtggccgg actggactaa cgccagaacg cgttgccatt aatcaagacg    540
atgctcgcat tcctgataac gaagggaatc agcctattga tacacctatt cgtgcagatg    600
gtaaagcagc ttatttttca accttgccaa tcaaagcgat ggttgctgcc attcatcagg    660
ctgggcttcc tgcttctgtt tctaatacag ctggtacctt tgtttgcaat catttgatgt    720
atcaagccct ttacttagtg gataaatatt gtccaaatgc caaagctggg tttatgcata    780 ttcccttttat gatggaacag gttgttgata aacctaatac agctgccatg aacctcgatg    840
atattacaag aggaattgag gctgctattt ttgccattgt cgatttcaaa gatcgttccg    900
atttaaaacg tgtaggggc gctactcact gactgtgacg ctactaaacc tatttttaaaa    960 aaacagagat atgaactaac tctgtttttt ttgtgctaaa aatgaaagac ctagggaaac    1020
ttttcatcgg tctttctcaa ttgtcatctt aatctaatac tacttctaac atcagcgggt    1080
atagtttgcc agtaattaag aaacgttgtt gatctaaatg agcaatccca ttcaaaacat    1140
taaggtcagg gtaatgggac ttatcaagat ttaaggcttt taacaaagga ctaatatcat    1200
aggtggctac caccttttcca gaatcaggtt ggagtttgac aatagtattg gtttgccaaa    1260
```

```
tattggcata gagataacca tctacatact ctaattcgtt aagcattgag atagggacac   1320
tttctatagc aactagt                                                  1337

<210> SEQ ID NO 33
<211> LENGTH: 1837
<212> TYPE: DNA
<213> ORGANISM: Streptococcus pyogenes

<400> SEQUENCE: 33
tcatgtttga cagcttatca tcgataagct tactttcga atcaggtcta tccttgaaac    60
aggtgcaaca tagattaggg catggagatt taccagacaa ctatgaacgt atatactcac   120
atcacgcaat cggcaattga tgacattgga actaaattca atcaatttgt tactaacaag   180
caactagatt gacaactaat tctcaacaaa cgttaattta acaacattca agtaactccc   240
accagctcca tcaatgctta ccgtaagtaa tcataactta ctaaaacctt gttacatcaa   300
ggttttttct ttttgtcttg ttcatgagtt accataactt tctatattat tgacaactaa   360
attgacaact cttcaattat ttttctgtct actcaaagtt ttcttcattt gatatagtct   420
aattccacca tcacttcttc cactctctct accgtcacaa cttcatcatc tctcactttt   480
tcgtgtggta acacataatc aaatatcttt ccgttttac gcactatcgc tactgtgtca    540
cctaaaatat accccttatc aatcgcttct ttaaactcat ctatatataa catatttcat   600
cctcctacct atctattcgt aaaaagataa aaataactat tgttttttt gttattttat    660 aataaaatta ttaatataag ttaatgtttt ttaaaaatat acaattttat tctatttata   720
gttagctatt ttttcattgt tagtaatatt ggtgaattgt aataacctttt ttaaatctag   780 aggagaaccc agatataaaa tggaggaata ttaatggaaa acaataaaaa agtattgaag    840
aaaatggtat tttttgtttt agtgacattt cttggactaa caatctcgca agaggtattt    900
gctcaacaag accccgatcc aagccaactt cacagatcta gtttagttaa aaaccttcaa    960
aatatatatt ttctttatga gggtgaccct gttactcacg agaatgtgaa atctgttgat  1020
caacttttat ctcacgattt aatatataat gtttcagggc caaattatga taaattaaaa  1080
actgaactta agaaccaaga gatggcaact ttatttaagg ataaaaacgt tgatatttat  1140
ggtgtagaat attaccatct ctgttattta tgtgaaaatg cagaaaggag tgcatgtatc  1200
tacgaggggg taacaaatca tgaagggaat catttagaaa ttcctaaaaa gatagtcgtt  1260
aaagtatcaa tcgatggtat ccaaagccta tcatttgata ttgaaacaaa taaaaaaatg  1320
gtaactgctc aagaattaga ctataaagtt agaaatatc ttacagataa taagcaacta  1380
tatactaatg gaccttctaa atatgaaact ggatatataa agttcatacc taagaataaa  1440
gaaagttttt ggtttgattt tttcccctgaa ccagaattta ctcaatctaa atatcttatg  1500
atatataaag ataatgaaac gcttgactca acacaagcc aaattgaagt ctacctaaca   1560
accaagtaac tttttgcttt tggcaacctt acctactgct ggatttagaa attttattgc  1620 aattcttta ttaatgtaaa aaccgctcat ttgatgagcg ttttgtctt atctaaagga    1680 gctttacctc ctaatgctgc aaaattttaa atgttggatt tttgtatttg tctattgtat  1740
ttgatgggta atcccatttt tcgacagaca tcgtcgtgcc acctctaaca ccaaaatcat  1800
agacaggagc ttgtagctta gcaactattt tatcgtc                          1837

<210> SEQ ID NO 34
<211> LENGTH: 841
<212> TYPE: DNA
<213> ORGANISM: Streptococcus pneumoniae
```

<400> SEQUENCE: 34

```
gatcaatatg tccaagaaac cacatgttcc taagacaaga gctaacagac tggccgtcaa      60
taatagtatt gttctttttt tcatcattac tccttaacta gtgtttaact gattaattag     120
ccagtaaata gtttatcttt atttacacta tctgttaaga tatagtaaaa tgaaataaga     180
acaggacagt caaatcgatt tctaacaatg ttttagaagt agaggtatac tattctaatt     240
tcaatctact atattttgca cattttcata aaaaaaatga aactagaac tcacattctg      300
ctctcatttt tcgttttccc gttctcctat cctgttttta ggagttagaa atgctgcta     360
cctttactta ctctccttta ataaagccaa tagttttca gcttctgcca taatagtatt     420
gttgtcctgg gtgccaaata gtaaattatt ttttaatcct gtgagagtct ctttggcatt     480
ggacttgata attggattct ggattttcc aagtaaatct tcagcctctc tcagttttct      540
taacctttca gtctcgacct gaggttcttc tgattcctct ggtgattctt ctggtgattc     600
ttcttctggt tcctctgttg gttttggaga ctctggtttc tcgctttgcg gtttctcttc     660
tcgaggggtt tcttcctcag ttttttctgt ctgaggtttc tcctcgtttg gttttttccgt    720
ttgattggta tcagcttgac catttttgtt tctttgaaca tggtcgctag cgttaccaaa     780
accattatct gaatgcgacg ttcgtttgga tgttcgacat agtacttgac agtcgccaaa     840
a                                                                      841
```

<210> SEQ ID NO 35
<211> LENGTH: 4500
<212> TYPE: DNA
<213> ORGANISM: Streptococcus pneumoniae

<400> SEQUENCE: 35

```
gatcaggaca gtcaaatcga tttctaacaa tgttttagaa gtagatgtgt actattctag      60
tttcaatcta ttatatttat agaattttt gttgctagat tgtcaaatt gcttaaaata      120
attttttca gaaagcaaaa gccgatacct atcgagtagg gtagttcttg ctatcgtcag     180
gcttgtctgt aggtgttaac acttttcaaa aatctcttca aacaacgtca gctttgcctt     240
gccgtatata tgttactgac ttcgtcagtt ctatctgcca cctcaaaacg gtgttttgag     300
ctgacttcgt cagttctatc cacaacctca aaacagtgtt ttgagctgac ttcgtcagtt     360
ctatccacaa cctcaaaaca gtgttttgag ctgactttgt cagtcttatc tacaacctca     420
aaacagtgtt ttgagcatca tgcggctagc ttcttagttt gctctttgat tttcattgag     480
tataaaaaca gatgagtttc tgttttcttt ttatggacta taaatgttca gctgaaacta     540
ctttcaagga cattattata taaagaatt ttttgaaact aaaatctact atattacact      600
atattgaaag cgttttaaaa atgaggtata ataaatttac taacacttat aaaagtgat      660
agaatctatc tttatgtata tttaaagata gattgctgta aaaatagtag tagctatgcg     720
aaataacaga tagagagaag ggattgaagc ttagaaaagg ggataatat gatatttaag      780
gcattcaaga caaaaaagca gagaaaaaga caagttgaac tacttttgac agttttttc      840
gacagttttc tgattgattt atttcttcac ttatttggga ttgtccccctt taagctggat    900
aagattctga ttgtgagctt gattatattt cccattattt ctacaagtat ttatgcttat     960
gaaaagctat ttgaaaaagt gttcgataag gattgagcag gaagtatggt gtaaatagca    1020
taagctgatg tccatcattt gcttataaag agatatttta gtttaattgc agcggtgtcc    1080
tggtagataa actagattgg caggagtctg attggagaaa ggagagggga aatttggcac    1140
caatttgaga tagtttgttt agttcatttt tgtcatttaa atgaactgta gtaaaagaaa    1200
```

-continued

```
gttaataaaa gacaaactaa gtgcattttc tggaataaat gtcttatttc agaaatcggg      1260
atatagatat agagaggaac agtatgaatc ggagtgttca agaacgtaag tgtcgttata      1320
gcattaggaa actatcggta ggagcggttt ctatgattgt aggagcagtg gtatttggaa      1380
cgtctcctgt tttagctcaa gaaggggcaa gtgagcaacc tctggcaaat gaaactcaac      1440
tttcggggga gagctcaacc ctaactgata cagaaaagag ccagccttct tcagagactg      1500
aactttctgg caataagcaa gaacaagaaa ggaaagataa gcaagaagaa aaaattccaa      1560
gagattacta tgcacgagat ttggaaaatg tcgaaacagt gatagaaaaa gaagatgttg      1620
aaaccaatgc ttcaaatggt cagagagttg atttatcaag tgaactagat aaactaaaga      1680
aacttgaaaa cgcaacagtt cacatggagt ttaagccaga tgccaaggcc ccagcattct      1740
ataatctctt ttctgtgtca agtgctacta aaaaagatga gtacttcact atggcagttt      1800
acaataatac tgctactcta gagggcgtg gttcggatgg gaaacagttt tacaataatt      1860
acaacgatga acccttaaaa gttaaaccag gtcagtggaa ttctgtgact ttcacagttg      1920
aaaaaccgac agcagaacta cctaaaggcc gagtgcgcct ctacgtaaac ggggtattat      1980
ctcgaacaag tctgagatct ggcaatttca ttaaagatat gccagatgta acgcatgtgc      2040
aaatcggagc aaccaagcgt gccaacaata cggtttgggg gtcaaatcta cagattcgga      2100
atctcactgt gtataatcgt gctttaacac cagaagaggt acaaaaacgt agtcaacttt      2160
ttaaacgctc agatttagaa aaaaaactac ctgaaggagc ggctttaaca gagaaaacgg      2220
acatattcga agcgggcgt aacggtaaac caaataaaga tggaatcaag agttatcgta      2280
ttccagcact tctcaagaca gataaaggaa ctttgatcgc aggtgcagat gaacgccgtc      2340
tccattcgag tgactggggt gatatcggta tggtcatcag acgtagtgaa gataatggta      2400
aaacttgggg tgaccgagta accattacca acttacgtga caatccaaaa gcttctgacc      2460
catcgatcgg ttcaccagtg aatatcgata tggtgttggt tcaagatcct gaaaccaaac      2520
gaatcttttc tatctatgac atgttcccag aagggaaggg aatctttgga atgtcttcac      2580
aaaaagaaga agcctacaaa aaaatcgatg gaaaaaccta tcaaatcctc tatcgtgaag      2640
gagaaaaggg agcttatacc attcgagaaa atggtactgt ctatacacca gatggtaagg      2700
cgacagacta tcgcgttgtt gtagatcctg ttaaaccagc ctatagcgac aagggggatc      2760
tatacaaggg taaccaatta ctaggcaata tctacttcac aacaaacaaa acttctccat      2820
ttagaattgc caaggatagc tatctatgga tgtcctacag tgatgacgac gggaagacat      2880
ggtcagcgcc tcaagatatt actccgatgg tcaaagccga ttggatgaaa ttcttgggtg      2940
taggtcctgg aacaggaatt gtacttcgga atgggcctca caagggacgg attttgatac      3000
cggtttatac gactaataat gtatctcact taaatggctc gcaatcttct cgtatcatct      3060
attcagatga tcatggaaaa acttggcatg ctggagaagc ggtcaacgat aaccgtcagg      3120
tagacggtca aaagatccac tcttctacga tgaacaatag acgtgcgcaa aatacagaat      3180
caacggtggt acaactaaac aatggagatg ttaaactctt tatgcgtggt ttgactggag      3240
atcttcaggt tgctacaagt aaagacggag gagtgacttg ggagaaggat atcaaacgtt      3300
atccacaggt taaagatgtc tatgttcaaa tgtctgctat ccatacgatg cacgaaggaa      3360
aagaatacat catcctcagt aatgcaggtg gaccgaaacg tgaaaatggg atggtccact      3420
tggcacgtgt cgaagaaaat ggtgagttga cttggctcaa acacaatcca attcaaaaag      3480
gagagtttgc ctataattcg ctccaagaat taggaaatgg ggagtatggc atcttgtatg      3540
aacatactga aaaaggacaa aatgcctata ccctatcatt tagaaaattt aattgggact      3600
```

```
ttttgagcaa agatctgatt tctcctaccg aagcgaaagt gaagcgaact agagagatgg    3660
gcaaaggagt tattggcttg gagttcgact cagaagtatt ggtcaacaag gctccaaccc    3720
ttcaattggc aaatggtaaa acagcacgct tcatgaccca gtatgataca aaaaccctcc    3780
tatttacagt ggattcagag gatatgggtc aaaaagttac aggtttggca gaaggtgcaa    3840
ttgaaagtat gcataattta ccagtctctg tggcgggcac taagctttcg aatggaatga    3900
acggaagtga agctgctgtt catgaagtgc agaatacac aggcccatta gggacatccg     3960
gcgaagagcc agctccaaca gtcgagaagc cagaatacac aggcccacta gggacatccg    4020
gcgaagagcc agccccgaca gtcgagaagc cagaatacac aggcccacta gggacagctg    4080
gtgaagaagc agctccaaca gtcgagaagc cagaatttac aggggagtt aatggtacag      4140 agccagctgt tcatgaaatc gcagagtata agggatctga ttcgcttgta actcttacta    4200
caaaagaaga ttatacttac aaagctcctc ttgctcagca ggcacttcct gaaacaggaa    4260
acaaggagag tgacctccta gcttcactag gactaacagc tttcttcctt ggtctgttta    4320
cgctagggaa aaagagagaa caataagaga agaattctaa acatttgatt ttgtaaaaat    4380
agaaggagat agcaggtttt caagcctgct atctttttt gatgacattc aggctgatac      4440
gaaatcataa gaggtctgaa actactttca gagtagtctg ttctataaaa tatagtagat    4500

<210> SEQ ID NO 36
<211> LENGTH: 705
<212> TYPE: DNA
<213> ORGANISM: Staphylococcus epidermidis

<400> SEQUENCE: 36
gatccaagct tatcgatatc atcaaaaagt tggcgaacct tttcaaattt tggttcaaat      60
tcttgagatg tatagaattc aaaatattta ccatttgcat agtctgattg ctcaaagtct     120
tgatactttt ctccacgctc ttttgcaatt tccattgaac gttcgatgga ataatagttc     180
ataatcataa agaatatatt agcaaagtct tttgcttctt cagattcata gccaattta     240 tttttagcta gataaccatg taagttcatt actcctagtc caacagaatg tagttcacta    300
ttcgcttttt ttacacctgg tgcattttga atatttgctt catcacttac aactgtaaga    360
gcatccatac ctgtgaacac agaatctctg aatttacctg attccataac attcactata    420
ttcaatgagc ctaagttaca tgaaatatct cttttaattt catcttcaat tccatagtcg    480
ttaattactg atgtctcttg taattggaaa atttcagtac ataaattact cattttaatt    540
tgcccaatat ttgaattcgc atgtactttg tttgcattat ctttaaacat aagatatgga    600
taaccagact gtaattgtgt ttgtgcaatc atatttaaca tttcacgtgc gtctttttc    660 tttttatcga tttcgaaccc ggggtaccga attcctcgag tctag                    705

<210> SEQ ID NO 37
<211> LENGTH: 442
<212> TYPE: DNA
<213> ORGANISM: Staphylococcus aureus

<400> SEQUENCE: 37
gatcaatctt tgtcggtaca cgatattctt cacgactaaa taaacgctca ttcgcgattt     60
tataaatgaa tgttgataac aatgttgtat tatctactga atctcatta cgttgcatcg     120 gaaacattgt gttctgtatg taaaagccgt cttgataatc tttagtagta ccgaagctgg    180
tcatacgaga gttatatttt ccagccaaaa cgatattttt ataatcatta cgtgaaaaag    240
gtttcccttc attatcacac aaatattta gcttttcagt ttctatatca actgtagctt    300
```

```
ctttatccat acgttgaata attgtacgat tctgacgcac catcttttgc acacctttaa    360
tgttatttgt tttaaaagca tgaataagtt tttcaacaca acgatgtgaa tcttctaaga    420
agtcaccgta aaatgaagga tc                                             442
```

```
<210> SEQ ID NO 38
<211> LENGTH: 20
<212> TYPE: DNA
<213> ORGANISM: Enterococcus faecalis

<400> SEQUENCE: 38
gcaatacagg gaaaaatgtc                                                20

<210> SEQ ID NO 39
<211> LENGTH: 20
<212> TYPE: DNA
<213> ORGANISM: Enterococcus faecalis

<400> SEQUENCE: 39
cttcatcaaa caattaactc                                                20

<210> SEQ ID NO 40
<211> LENGTH: 20
<212> TYPE: DNA
<213> ORGANISM: Enterococcus faecalis

<400> SEQUENCE: 40
gaacagaaga agccaaaaaa                                                20

<210> SEQ ID NO 41
<211> LENGTH: 20
<212> TYPE: DNA
<213> ORGANISM: Enterococcus faecalis

<400> SEQUENCE: 41
gcaatcccaa ataatacggt                                                20

<210> SEQ ID NO 42
<211> LENGTH: 19
<212> TYPE: DNA
<213> ORGANISM: Escherichia coli

<400> SEQUENCE: 42
gctttccagc gtcatattg                                                 19

<210> SEQ ID NO 43
<211> LENGTH: 19
<212> TYPE: DNA
<213> ORGANISM: Escherichia coli

<400> SEQUENCE: 43
gatctcgaca aaatggtga                                                 19

<210> SEQ ID NO 44
<211> LENGTH: 25
<212> TYPE: DNA
<213> ORGANISM: Escherichia coli

<400> SEQUENCE: 44
cacccgcttg cgtggcaagc tgccc                                          25

<210> SEQ ID NO 45
<211> LENGTH: 25
<212> TYPE: DNA
```

<213> ORGANISM: Escherichia coli

<400> SEQUENCE: 45
cgtttgtgga ttccagttcc atccg 25

<210> SEQ ID NO 46
<211> LENGTH: 17
<212> TYPE: DNA
<213> ORGANISM: Escherichia coli

<400> SEQUENCE: 46
tcacccgctt gcgtggc 17

<210> SEQ ID NO 47
<211> LENGTH: 19
<212> TYPE: DNA
<213> ORGANISM: Escherichia coli

<400> SEQUENCE: 47
ggaactggaa tccacaaac 19

<210> SEQ ID NO 48
<211> LENGTH: 25
<212> TYPE: DNA
<213> ORGANISM: Escherichia coli

<400> SEQUENCE: 48
tgaagcactg gccgaaatgc tgcgt 25

<210> SEQ ID NO 49
<211> LENGTH: 25
<212> TYPE: DNA
<213> ORGANISM: Escherichia coli

<400> SEQUENCE: 49
gatgtacagg attcgttgaa ggctt 25

<210> SEQ ID NO 50
<211> LENGTH: 25
<212> TYPE: DNA
<213> ORGANISM: Escherichia coli

<400> SEQUENCE: 50
tagcgaaggc gtagcagaaa ctaac 25

<210> SEQ ID NO 51
<211> LENGTH: 25
<212> TYPE: DNA
<213> ORGANISM: Escherichia coli

<400> SEQUENCE: 51
gcaacccgaa ctcaacgccg gattt 25

<210> SEQ ID NO 52
<211> LENGTH: 25
<212> TYPE: DNA
<213> ORGANISM: Escherichia coli

<400> SEQUENCE: 52
atacacaagg gtcgcatctg cggcc 25

<210> SEQ ID NO 53
<211> LENGTH: 26
<212> TYPE: DNA

<213> ORGANISM: Escherichia coli

<400> SEQUENCE: 53
tgcgtatgca ttgcagacct tgtggc         26

<210> SEQ ID NO 54
<211> LENGTH: 25
<212> TYPE: DNA
<213> ORGANISM: Escherichia coli

<400> SEQUENCE: 54
gctttcactg gatatcgcgc ttggg          25

<210> SEQ ID NO 55
<211> LENGTH: 19
<212> TYPE: DNA
<213> ORGANISM: Escherichia coli

<400> SEQUENCE: 55
gcaacccgaa ctcaacgcc                 19

<210> SEQ ID NO 56
<211> LENGTH: 19
<212> TYPE: DNA
<213> ORGANISM: Escherichia coli

<400> SEQUENCE: 56
gcagatgcga cccttgtgt                 19

<210> SEQ ID NO 57
<211> LENGTH: 23
<212> TYPE: DNA
<213> ORGANISM: Klebsiella pneumoniae

<400> SEQUENCE: 57
gtggtgtcgt tcagcgcttt cac            23

<210> SEQ ID NO 58
<211> LENGTH: 25
<212> TYPE: DNA
<213> ORGANISM: Klebsiella pneumoniae

<400> SEQUENCE: 58
gcgatattca caccctacgc agcca          25

<210> SEQ ID NO 59
<211> LENGTH: 26
<212> TYPE: DNA
<213> ORGANISM: Klebsiella pneumoniae

<400> SEQUENCE: 59
gtcgaaaatg ccggaagagg tatacg         26

<210> SEQ ID NO 60
<211> LENGTH: 26
<212> TYPE: DNA
<213> ORGANISM: Klebsiella pneumoniae

<400> SEQUENCE: 60
actgagctgc agaccggtaa aactca         26

<210> SEQ ID NO 61
<211> LENGTH: 19
<212> TYPE: DNA

<213> ORGANISM: Klebsiella pneumoniae

<400> SEQUENCE: 61
gacagtcagt tcgtcagcc                                                19

<210> SEQ ID NO 62
<211> LENGTH: 19
<212> TYPE: DNA
<213> ORGANISM: Klebsiella pneumoniae

<400> SEQUENCE: 62
cgtagggtgt gaatatcgc                                                19

<210> SEQ ID NO 63
<211> LENGTH: 26
<212> TYPE: DNA
<213> ORGANISM: Klebsiella pneumoniae

<400> SEQUENCE: 63
cgtgatggat attcttaacg aagggc                                        26

<210> SEQ ID NO 64
<211> LENGTH: 23
<212> TYPE: DNA
<213> ORGANISM: Klebsiella pneumoniae

<400> SEQUENCE: 64
accaaactgt tgagccgcct gga                                           23

<210> SEQ ID NO 65
<211> LENGTH: 23
<212> TYPE: DNA
<213> ORGANISM: Klebsiella pneumoniae

<400> SEQUENCE: 65
gtgatcgccc ctcatctgct act                                           23

<210> SEQ ID NO 66
<211> LENGTH: 26
<212> TYPE: DNA
<213> ORGANISM: Klebsiella pneumoniae

<400> SEQUENCE: 66
cgcccttcgt taagaatatc catcac                                        26

<210> SEQ ID NO 67
<211> LENGTH: 19
<212> TYPE: DNA
<213> ORGANISM: Klebsiella pneumoniae

<400> SEQUENCE: 67
tcgcccctca tctgctact                                                19

<210> SEQ ID NO 68
<211> LENGTH: 19
<212> TYPE: DNA
<213> ORGANISM: Klebsiella pneumoniae

<400> SEQUENCE: 68
gatcgtgatg gatattctt                                                19

<210> SEQ ID NO 69
<211> LENGTH: 25
<212> TYPE: DNA

<213> ORGANISM: Klebsiella pneumoniae

<400> SEQUENCE: 69
caggaagatg ctgcaccggt tgttg                                    25

<210> SEQ ID NO 70
<211> LENGTH: 25
<212> TYPE: DNA
<213> ORGANISM: Proteus mirabilis

<400> SEQUENCE: 70
tggttcactg actttgcgat gtttc                                    25

<210> SEQ ID NO 71
<211> LENGTH: 25
<212> TYPE: DNA
<213> ORGANISM: Proteus mirabilis

<400> SEQUENCE: 71
tcgaggatgg catgcactag aaaat                                    25

<210> SEQ ID NO 72
<211> LENGTH: 30
<212> TYPE: DNA
<213> ORGANISM: Proteus mirabilis

<400> SEQUENCE: 72
cgctgattag gtttcgctaa aatcttatta                               30

<210> SEQ ID NO 73
<211> LENGTH: 30
<212> TYPE: DNA
<213> ORGANISM: Proteus mirabilis

<400> SEQUENCE: 73
ttgatcctca ttttattaat cacatgacca                               30

<210> SEQ ID NO 74
<211> LENGTH: 19
<212> TYPE: DNA
<213> ORGANISM: Proteus mirabilis

<400> SEQUENCE: 74
gaaacatcgc aaagtcagt                                           19

<210> SEQ ID NO 75
<211> LENGTH: 20
<212> TYPE: DNA
<213> ORGANISM: Proteus mirabilis

<400> SEQUENCE: 75
ataaaatgag gatcaagttc                                          20

<210> SEQ ID NO 76
<211> LENGTH: 30
<212> TYPE: DNA
<213> ORGANISM: Proteus mirabilis

<400> SEQUENCE: 76
ccgcctttag cattaattgg tgtttatagt                               30

<210> SEQ ID NO 77
<211> LENGTH: 30
<212> TYPE: DNA

<210> SEQ ID NO 77
<211> LENGTH: 30
<212> TYPE: DNA
<213> ORGANISM: Proteus mirabilis

<400> SEQUENCE: 77
cctattgcag ataccttaaa tgtcttgggc                               30

<210> SEQ ID NO 78
<211> LENGTH: 26
<212> TYPE: DNA
<213> ORGANISM: Streptococcus pneumoniae

<400> SEQUENCE: 78
agtaaaatga aataagaaca ggacag                                   26

<210> SEQ ID NO 79
<211> LENGTH: 25
<212> TYPE: DNA
<213> ORGANISM: Streptococcus pneumoniae

<400> SEQUENCE: 79
aaaacaggat aggagaacgg gaaaa                                    25

<210> SEQ ID NO 80
<211> LENGTH: 25
<212> TYPE: DNA
<213> ORGANISM: Proteus mirabilis

<400> SEQUENCE: 80
ttgagtgatg atttcactga ctccc                                    25

<210> SEQ ID NO 81
<211> LENGTH: 25
<212> TYPE: DNA
<213> ORGANISM: Proteus mirabilis

<400> SEQUENCE: 81
gtcagacagt gatgctgacg acaca                                    25

<210> SEQ ID NO 82
<211> LENGTH: 27
<212> TYPE: DNA
<213> ORGANISM: Proteus mirabilis

<400> SEQUENCE: 82
tggttgtcat gctgtttgtg tgaaaat                                  27

<210> SEQ ID NO 83
<211> LENGTH: 19
<212> TYPE: DNA
<213> ORGANISM: Pseudomonas aeruginosa

<400> SEQUENCE: 83
cgagcgggtg gtgttcatc                                           19

<210> SEQ ID NO 84
<211> LENGTH: 19
<212> TYPE: DNA
<213> ORGANISM: Pseudomonas aeruginosa

<400> SEQUENCE: 84
caagtcgtcg tcggaggga                                           19

<210> SEQ ID NO 85
<211> LENGTH: 19
<212> TYPE: DNA

<213> ORGANISM: Pseudomonas aeruginosa

<400> SEQUENCE: 85
tcgctgttca tcaagaccc 19

<210> SEQ ID NO 86
<211> LENGTH: 19
<212> TYPE: DNA
<213> ORGANISM: Pseudomonas aeruginosa

<400> SEQUENCE: 86
ccgagaacca gacttcatc 19

<210> SEQ ID NO 87
<211> LENGTH: 25
<212> TYPE: DNA
<213> ORGANISM: Pseudomonas aeruginosa

<400> SEQUENCE: 87
aatgcggctg tacctcggcg ctggt 25

<210> SEQ ID NO 88
<211> LENGTH: 25
<212> TYPE: DNA
<213> ORGANISM: Pseudomonas aeruginosa

<400> SEQUENCE: 88
ggcggagggc cagttgcacc tgcca 25

<210> SEQ ID NO 89
<211> LENGTH: 25
<212> TYPE: DNA
<213> ORGANISM: Pseudomonas aeruginosa

<400> SEQUENCE: 89
agccctgctc ctcggcagcc tctgc 25

<210> SEQ ID NO 90
<211> LENGTH: 25
<212> TYPE: DNA
<213> ORGANISM: Pseudomonas aeruginosa

<400> SEQUENCE: 90
tggcttttgc aaccgcgttc aggtt 25

<210> SEQ ID NO 91
<211> LENGTH: 25
<212> TYPE: DNA
<213> ORGANISM: Pseudomonas aeruginosa

<400> SEQUENCE: 91
gcgcccgcga gggcatgctt cgatg 25

<210> SEQ ID NO 92
<211> LENGTH: 25
<212> TYPE: DNA
<213> ORGANISM: Pseudomonas aeruginosa

<400> SEQUENCE: 92
acctgggcgc caactacaag ttcta 25

<210> SEQ ID NO 93
<211> LENGTH: 25
<212> TYPE: DNA

-continued

<213> ORGANISM: Pseudomonas aeruginosa

<400> SEQUENCE: 93
ggctacgctg ccgggctgca ggccg                                    25

<210> SEQ ID NO 94
<211> LENGTH: 25
<212> TYPE: DNA
<213> ORGANISM: Pseudomonas aeruginosa

<400> SEQUENCE: 94
ccgatctaca ccatcgagat gggcg                                    25

<210> SEQ ID NO 95
<211> LENGTH: 25
<212> TYPE: DNA
<213> ORGANISM: Pseudomonas aeruginosa

<400> SEQUENCE: 95
gagcgcggct atgtgttcgt cggct                                    25

<210> SEQ ID NO 96
<211> LENGTH: 29
<212> TYPE: DNA
<213> ORGANISM: Staphylococcus saprophyticus

<400> SEQUENCE: 96 cgttttacc cttaccttt cgtactacc                                  29

<210> SEQ ID NO 97
<211> LENGTH: 30
<212> TYPE: DNA
<213> ORGANISM: Staphylococcus saprophyticus

<400> SEQUENCE: 97
tcaggcagag gtagtacgaa aaggtaaggg                               30

<210> SEQ ID NO 98
<211> LENGTH: 26
<212> TYPE: DNA
<213> ORGANISM: Staphylococcus saprophyticus

<400> SEQUENCE: 98 cgttttacc cttaccttt cgtact                                     26

<210> SEQ ID NO 99
<211> LENGTH: 28
<212> TYPE: DNA
<213> ORGANISM: Staphylococcus saprophyticus

<400> SEQUENCE: 99
atcgatcatc acattccatt tgttttta                                 28

<210> SEQ ID NO 100
<211> LENGTH: 27
<212> TYPE: DNA
<213> ORGANISM: Staphylococcus saprophyticus

<400> SEQUENCE: 100
caccaagttt gacacgtgaa gattcat                                  27

<210> SEQ ID NO 101
<211> LENGTH: 30
<212> TYPE: DNA

```
<213> ORGANISM: Staphylococcus saprophyticus

<400> SEQUENCE: 101
atgagtgaag cggagtcaga ttatgtgcag                                30

<210> SEQ ID NO 102
<211> LENGTH: 25
<212> TYPE: DNA
<213> ORGANISM: Staphylococcus saprophyticus

<400> SEQUENCE: 102
cgctcattac gtacagtgac aatcg                                     25

<210> SEQ ID NO 103
<211> LENGTH: 30
<212> TYPE: DNA
<213> ORGANISM: Staphylococcus saprophyticus

<400> SEQUENCE: 103
ctggttagct tgactcttaa caatcttgtc                                30

<210> SEQ ID NO 104
<211> LENGTH: 30
<212> TYPE: DNA
<213> ORGANISM: Staphylococcus saprophyticus

<400> SEQUENCE: 104
gacgcgattg tcactgtacg taatgagcga                                30

<210> SEQ ID NO 105
<211> LENGTH: 28
<212> TYPE: DNA
<213> ORGANISM: Haemophilus influenzae

<400> SEQUENCE: 105
gcgtcagaaa aagtaggcga aatgaaag                                  28

<210> SEQ ID NO 106
<211> LENGTH: 25
<212> TYPE: DNA
<213> ORGANISM: Haemophilus influenzae

<400> SEQUENCE: 106
agcggctcta tcttgtaatg acaca                                     25

<210> SEQ ID NO 107
<211> LENGTH: 25
<212> TYPE: DNA
<213> ORGANISM: Haemophilus influenzae

<400> SEQUENCE: 107
gaaacgtgaa ctcccctcta tataa                                     25

<210> SEQ ID NO 108
<211> LENGTH: 25
<212> TYPE: DNA
<213> ORGANISM: Moraxella catarrhalis

<400> SEQUENCE: 108
gccccaaaac aatgaaacat atggt                                     25

<210> SEQ ID NO 109
<211> LENGTH: 25
<212> TYPE: DNA
```

<213> ORGANISM: Moraxella catarrhalis

<400> SEQUENCE: 109
ctgcagattt tggaatcata tcgcc                                   25

<210> SEQ ID NO 110
<211> LENGTH: 25
<212> TYPE: DNA
<213> ORGANISM: Moraxella catarrhalis

<400> SEQUENCE: 110
tggtttgacc agtatttaac gccat                                   25

<210> SEQ ID NO 111
<211> LENGTH: 25
<212> TYPE: DNA
<213> ORGANISM: Moraxella catarrhalis

<400> SEQUENCE: 111
caacggcacc tgatgtacct tgtac                                   25

<210> SEQ ID NO 112
<211> LENGTH: 18
<212> TYPE: DNA
<213> ORGANISM: Moraxella catarrhalis

<400> SEQUENCE: 112
ggcacctgat gtaccttg                                           18

<210> SEQ ID NO 113
<211> LENGTH: 17
<212> TYPE: DNA
<213> ORGANISM: Moraxella catarrhalis

<400> SEQUENCE: 113
aacagctcac acgcatt                                            17

<210> SEQ ID NO 114
<211> LENGTH: 25
<212> TYPE: DNA
<213> ORGANISM: Moraxella catarrhalis

<400> SEQUENCE: 114
ttacaacctg caccacaagt catca                                   25

<210> SEQ ID NO 115
<211> LENGTH: 25
<212> TYPE: DNA
<213> ORGANISM: Moraxella catarrhalis

<400> SEQUENCE: 115
gtacaaacaa gccgtcagcg actta                                   25

<210> SEQ ID NO 116
<211> LENGTH: 23
<212> TYPE: DNA
<213> ORGANISM: Moraxella catarrhalis

<400> SEQUENCE: 116
caatctgcgt gtgtgcgttc act                                     23

<210> SEQ ID NO 117
<211> LENGTH: 26
<212> TYPE: DNA

<213> ORGANISM: Moraxella catarrhalis

<400> SEQUENCE: 117
gctactttgt cagctttagc cattca                                          26

<210> SEQ ID NO 118
<211> LENGTH: 24
<212> TYPE: DNA
<213> ORGANISM: Moraxella catarrhalis

<400> SEQUENCE: 118
tgttttgagc tttttatttt ttga                                            24

<210> SEQ ID NO 119
<211> LENGTH: 22
<212> TYPE: DNA
<213> ORGANISM: Moraxella catarrhalis

<400> SEQUENCE: 119
cgctgacggc ttgtttgtac ca                                              22

<210> SEQ ID NO 120
<211> LENGTH: 25
<212> TYPE: DNA
<213> ORGANISM: Streptococcus pneumoniae

<400> SEQUENCE: 120
tctgtgctag agactgcccc atttc                                           25

<210> SEQ ID NO 121
<211> LENGTH: 25
<212> TYPE: DNA
<213> ORGANISM: Streptococcus pneumoniae

<400> SEQUENCE: 121
cgatgtcttg attgagcagg gttat                                           25

<210> SEQ ID NO 122
<211> LENGTH: 25
<212> TYPE: DNA
<213> ORGANISM: Artificial Sequence
<220> FEATURE:
<223> OTHER INFORMATION: Oligonucleotide

<400> SEQUENCE: 122
atcccacctt aggcggctgg ctcca                                           25

<210> SEQ ID NO 123
<211> LENGTH: 31
<212> TYPE: DNA
<213> ORGANISM: Artificial Sequence
<220> FEATURE:
<223> OTHER INFORMATION: Oligonucleotide

<400> SEQUENCE: 123
acgtcaagtc atcatggccc ttacgagtag g                                    31

<210> SEQ ID NO 124
<211> LENGTH: 25
<212> TYPE: DNA
<213> ORGANISM: Artificial Sequence
<220> FEATURE:
<223> OTHER INFORMATION: Oligonucleotide

<400> SEQUENCE: 124

```
gtgtgacggg cggtgtgtac aaggc                                          25

<210> SEQ ID NO 125
<211> LENGTH: 28
<212> TYPE: DNA
<213> ORGANISM: Artificial Sequence
<220> FEATURE:
<223> OTHER INFORMATION: Oligonucleotide

<400> SEQUENCE: 125
gagttgcaga ctccaatccg gactacga                                       28

<210> SEQ ID NO 126
<211> LENGTH: 20
<212> TYPE: DNA
<213> ORGANISM: Artificial Sequence
<220> FEATURE:
<223> OTHER INFORMATION: Oligonucleotide

<400> SEQUENCE: 126
ggaggaaggt ggggatgacg                                                20

<210> SEQ ID NO 127
<211> LENGTH: 20
<212> TYPE: DNA
<213> ORGANISM: Artificial Sequence
<220> FEATURE:
<223> OTHER INFORMATION: Oligonucleotide

<400> SEQUENCE: 127
atggtgtgac gggcggtgtg                                                20

<210> SEQ ID NO 128
<211> LENGTH: 32
<212> TYPE: DNA
<213> ORGANISM: Artificial Sequence
<220> FEATURE:
<223> OTHER INFORMATION: Oligonucleotide

<400> SEQUENCE: 128
ccctatacat caccttgcgg tttagcagag ag                                  32

<210> SEQ ID NO 129
<211> LENGTH: 28
<212> TYPE: DNA
<213> ORGANISM: Artificial Sequence
<220> FEATURE:
<223> OTHER INFORMATION: Oligonucleotide

<400> SEQUENCE: 129 gggggggacca tcctccaagg ctaaatac                                      28

<210> SEQ ID NO 130
<211> LENGTH: 32
<212> TYPE: DNA
<213> ORGANISM: Artificial Sequence
<220> FEATURE:
<223> OTHER INFORMATION: Oligonucleotide

<400> SEQUENCE: 130
cgtccacttt cgtgtttgca gagtgctgtg tt                                  32

<210> SEQ ID NO 131
<211> LENGTH: 20
<212> TYPE: DNA
<213> ORGANISM: Escherichia coli
```

```
<400> SEQUENCE: 131
caggagtacg gtgatttta                                              20

<210> SEQ ID NO 132
<211> LENGTH: 20
<212> TYPE: DNA
<213> ORGANISM: Escherichia coli

<400> SEQUENCE: 132
atttctggtt tggtcataca                                             20

<210> SEQ ID NO 133
<211> LENGTH: 20
<212> TYPE: DNA
<213> ORGANISM: Proteus mirabilis

<400> SEQUENCE: 133
cgggagtcag tgaaatcatc                                             20

<210> SEQ ID NO 134
<211> LENGTH: 20
<212> TYPE: DNA
<213> ORGANISM: Proteus mirabilis

<400> SEQUENCE: 134
ctaaaatcgc cacacctctt                                             20

<210> SEQ ID NO 135
<211> LENGTH: 18
<212> TYPE: DNA
<213> ORGANISM: Klebsiella pneumoniae

<400> SEQUENCE: 135
gcagcgtggt gtcgttca                                               18

<210> SEQ ID NO 136
<211> LENGTH: 18
<212> TYPE: DNA
<213> ORGANISM: Klebsiella pneumoniae

<400> SEQUENCE: 136
agctggcaac ggctggtc                                               18

<210> SEQ ID NO 137
<211> LENGTH: 20
<212> TYPE: DNA
<213> ORGANISM: Klebsiella pneumoniae

<400> SEQUENCE: 137
attcacaccc tacgcagcca                                             20

<210> SEQ ID NO 138
<211> LENGTH: 20
<212> TYPE: DNA
<213> ORGANISM: Klebsiella pneumoniae

<400> SEQUENCE: 138
atccggcagc atctctttgt                                             20

<210> SEQ ID NO 139
<211> LENGTH: 25
<212> TYPE: DNA
<213> ORGANISM: Staphylococcus saprophyticus
```

```
<400> SEQUENCE: 139
ctggttagct tgactcttaa caatc                                              25

<210> SEQ ID NO 140
<211> LENGTH: 25
<212> TYPE: DNA
<213> ORGANISM: Staphylococcus saprophyticus

<400> SEQUENCE: 140
tcttaacgat agaatggagc aactg                                              25

<210> SEQ ID NO 141
<211> LENGTH: 20
<212> TYPE: DNA
<213> ORGANISM: Streptococcus pyogenes

<400> SEQUENCE: 141
tgaaaattct tgtaacaggc                                                    20

<210> SEQ ID NO 142
<211> LENGTH: 20
<212> TYPE: DNA
<213> ORGANISM: Streptococcus pyogenes

<400> SEQUENCE: 142
ggccaccagc ttgcccaata                                                    20

<210> SEQ ID NO 143
<211> LENGTH: 20
<212> TYPE: DNA
<213> ORGANISM: Streptococcus pyogenes

<400> SEQUENCE: 143
atattttctt tatgagggtg                                                    20

<210> SEQ ID NO 144
<211> LENGTH: 20
<212> TYPE: DNA
<213> ORGANISM: Streptococcus pyogenes

<400> SEQUENCE: 144
atccttaaat aaagttgcca                                                    20

<210> SEQ ID NO 145
<211> LENGTH: 25
<212> TYPE: DNA
<213> ORGANISM: Staphylococcus epidermidis

<400> SEQUENCE: 145
atcaaaaagt tggcgaacct tttca                                              25

<210> SEQ ID NO 146
<211> LENGTH: 25
<212> TYPE: DNA
<213> ORGANISM: Staphylococcus epidermidis

<400> SEQUENCE: 146
caaaagagcg tggagaaaag tatca                                              25

<210> SEQ ID NO 147
<211> LENGTH: 30
<212> TYPE: DNA
<213> ORGANISM: Staphylococcus epidermidis
```

-continued

```
<400> SEQUENCE: 147
tctcttttaa tttcatcttc aattccatag                                          30

<210> SEQ ID NO 148
<211> LENGTH: 30
<212> TYPE: DNA
<213> ORGANISM: Staphylococcus epidermidis

<400> SEQUENCE: 148
aaacacaatt acagtctggt tatccatatc                                          30

<210> SEQ ID NO 149
<211> LENGTH: 30
<212> TYPE: DNA
<213> ORGANISM: Staphylococcus aureus

<400> SEQUENCE: 149
cttcatttta cggtgacttc ttagaagatt                                          30

<210> SEQ ID NO 150
<211> LENGTH: 30
<212> TYPE: DNA
<213> ORGANISM: Staphylococcus aureus

<400> SEQUENCE: 150
tcaactgtag cttctttatc catacgttga                                          30

<210> SEQ ID NO 151
<211> LENGTH: 30
<212> TYPE: DNA
<213> ORGANISM: Staphylococcus aureus

<400> SEQUENCE: 151
atattttagc ttttcagttt ctatatcaac                                          30

<210> SEQ ID NO 152
<211> LENGTH: 30
<212> TYPE: DNA
<213> ORGANISM: Staphylococcus aureus

<400> SEQUENCE: 152
aatctttgtc ggtacacgat attcttcacg                                          30

<210> SEQ ID NO 153
<211> LENGTH: 30
<212> TYPE: DNA
<213> ORGANISM: Staphylococcus aureus

<400> SEQUENCE: 153
cgtaatgaga tttcagtaga taatacaaca                                          30

<210> SEQ ID NO 154
<211> LENGTH: 25
<212> TYPE: DNA
<213> ORGANISM: Haemophilus influenzae

<400> SEQUENCE: 154
tttaacgatc cttttactcc ttttg                                               25

<210> SEQ ID NO 155
<211> LENGTH: 25
<212> TYPE: DNA
<213> ORGANISM: Haemophilus influenzae
```

```
<400> SEQUENCE: 155
actgctgttg taaagaggtt aaaat                                           25

<210> SEQ ID NO 156
<211> LENGTH: 20
<212> TYPE: DNA
<213> ORGANISM: Streptococcus pneumoniae

<400> SEQUENCE: 156
atttggtgac gggtgacttt                                                 20

<210> SEQ ID NO 157
<211> LENGTH: 20
<212> TYPE: DNA
<213> ORGANISM: Streptococcus pneumoniae

<400> SEQUENCE: 157
gctgaggatt tgttcttctt                                                 20

<210> SEQ ID NO 158
<211> LENGTH: 20
<212> TYPE: DNA
<213> ORGANISM: Streptococcus pneumoniae

<400> SEQUENCE: 158
gagcggtttc tatgattgta                                                 20

<210> SEQ ID NO 159
<211> LENGTH: 20
<212> TYPE: DNA
<213> ORGANISM: Streptococcus pneumoniae

<400> SEQUENCE: 159
atctttcctt tcttgttctt                                                 20

<210> SEQ ID NO 160
<211> LENGTH: 18
<212> TYPE: DNA
<213> ORGANISM: Moraxella catarrhalis

<400> SEQUENCE: 160
gctcaaatca gggtcagc                                                   18

<210> SEQ ID NO 161
<211> LENGTH: 861
<212> TYPE: DNA
<213> ORGANISM: Escherichia coli

<400> SEQUENCE: 161
atgagtattc aacatttccg tgtcgccctt attcccttttt ttgcggcatt ttgccttcct    60 gttttttgctc acccagaaac gctggtgaaa gtaaaagatg ctgaagatca gttgggtgca   120
cgagtgggtt acatcgaact ggatctcaac agcggtaaga tccttgagag ttttcgcccc   180
gaagaacgtt ttccaatgat gagcactttt aaagttctgc tatgtggcgc ggtattatcc   240
cgtgttgacg ccgggcaaga gcaactcggt cgccgcatac actattctca gaatgacttg   300
gttgagtact caccagtcac agaaaagcat cttacggatg gcatgacagt aagagaatta   360
tgcagtgctg ccataaccat gagtgataac actgcggcca acttacttct gacaacgatc   420
ggaggaccga aggagctaac cgcttttttg cacaacatgg gggatcatgt aactcgcctt   480
gatcgttggg aaccggagct gaatgaagcc ataccaaacg acgagcgtga ccacacgatg   540
```

| | |
|---|---:|
| cctgcagcaa tggcaacaac gttgcgcaaa ctattaactg gcgaactact tactctagct | 600 |
| tcccggcaac aattaataga ctggatggag gcggataaag ttgcaggacc acttctgcgc | 660 |
| tcggcccttc cggctggctg gtttattgct gataaatctg gagccggtga gcgtgggtct | 720 |
| cgcggtatca ttgcagcact ggggccagat ggtaagccct cccgtatcgt agttatctac | 780 |
| acgacgggga gtcaggcaac tatggatgaa cgaaatagac agatcgctga gataggtgcc | 840 |
| tcactgatta agcattggta a | 861 |

<210> SEQ ID NO 162
<211> LENGTH: 918
<212> TYPE: DNA
<213> ORGANISM: Pasteurella haemolytica

<400> SEQUENCE: 162

| | |
|---|---:|
| atgttaaata agttaaaaat cggcacatta ttattgctga cattaacggc ttgttcgccc | 60 |
| aattctgttc attcggtaac gtctaatccg cagcctgcta gtgcgcctgt gcaacaatca | 120 |
| gccacacaag ccacctttca acagactttg gcgaatttgg aacagcagta tcaagcccga | 180 |
| attggcgttt atgtatggga tacagaaacg ggacattctt tgtcttatcg tgcagatgaa | 240 |
| cgctttgctt atgcgtccac tttcaaggcg ttgttggctg gggcggtgtt gcaatcgctg | 300 |
| cctgaaaaag atttaaatcg taccatttca tatagccaaa aagatttggt tagttattct | 360 |
| cccgaaaccc aaaaatacgt tggcaaaggc atgacgattg cccaattatg tgaagcagcc | 420 |
| gtgcggttta gcgacaacag cgcgaccaat ttgctgctca agaattgggt ggcgtggaa | 480 |
| caatatcaac gtattttgcg acaattaggc gataacgtaa cccataccaa tcggctagaa | 540 |
| cccgatttaa atcaagccaa acccaacgat attcgtgata cgagtacacc caaacaaatg | 600 |
| gcgatgaatt taaatgcgta tttattgggc aacacattaa ccgaatcgca aaaaacgatt | 660 |
| ttgtggaatt ggttggacaa taacgcaaca ggcaatccat tgattcgcgc tgctacgcca | 720 |
| acatcgtgga aagtgtacga taaaagcggg gcgggtaaat atggtgtacg caatgatatt | 780 |
| gcggtggttc gcataccaaa tcgcaaaccg attgtgatgg caatcatgag tacgcaattt | 840 |
| accgaagaag ccaaattcaa caataaatta gtagaagatg cagcaaagca agtatttcat | 900 |
| actttacagc tcaactaa | 918 |

<210> SEQ ID NO 163
<211> LENGTH: 864
<212> TYPE: DNA
<213> ORGANISM: Klebsiella pneumoniae

<400> SEQUENCE: 163

| | |
|---|---:|
| atgcgttata ttcgcctgtg tattatctcc ctgttagcca ccctgccgct ggcggtacac | 60 |
| gccagcccgc agccgcttga gcaaattaaa ctaagcgaaa gccagctgtc gggccgcgta | 120 |
| ggcatgatag aaatggatct ggccagcggc cgcacgctga ccgcctggcg cgccgatgaa | 180 |
| cgctttccca tgatgagcac ctttaaagta gtgctctgcg gcgcagtgct ggcgcgggtg | 240 |
| gatgccggtg acgaacagct ggagcgaaag atccactatc gccagcagga tctggtggac | 300 |
| tactcgccgg tcagcgaaaa acaccttgcc gacgcaatga cggtcggcga actctgcgcc | 360 |
| gccgccatta ccatgagcga taacagcgcc gccaatctgc tactggccac cgtcggcggc | 420 |
| cccgcaggat tgactgcctt tttgcgccag atcggcgaca acgtcacccg ccttgaccgc | 480 |
| tgggaaacgg aactgaatga ggcgcttccc ggcgacgccc gcgacaccac tacccccggc | 540 |
| agcatggccg cgaccctgcg caacgttggc ctgaccagcc agcgtctgag cgcccgttcg | 600 |

```
caacggcagc tgctgcagtg gatggtggac gatcgggtcg ccggaccgtt gatccgctcc    660
gtgctgccgg cgggctggtt tatcgccgat aagaccggag ctggcgagcg gggtgcgcgc    720
gggattgtcg ccctgcttgg cccgaataac aaagcagagc gcattgtggt gatttatctg    780
cgggatcccc cggcgagcat ggccgagcga atcagcaaa tcgccgggat cggcaaggcg     840
ctgtacgagc actggcaacg ctaa                                           864
```

<210> SEQ ID NO 164
<211> LENGTH: 534
<212> TYPE: DNA
<213> ORGANISM: Klebsiella pneumoniae

<400> SEQUENCE: 164

```
atggacacaa cgcaggtcac attgatacac aaaattctag ctgcggcaga tgagcgaaat     60
ctgccgctct ggatcggtgg gggctgggcg atcgatgcac ggctagggcg tgtaacacgc    120
aagcacgatg atattgatct gacgtttccc ggcgagaggc gcggcgagct cgaggcaata    180
gttgaaatgc tcggcgggcg cgtcatggag gagttggact atggattctt agcggagatc    240
ggggatgagt tacttgactg cgaacctgct tggtgggcag acgaagcgta tgaaatcgcg    300
gaggctccgc agggctcgtg cccagaggcg gctgagggcg tcatcgccgg cggccagtc     360 cgttgtaaca gctgggaggc gatcatctgg gattactttt actatgccga tgaagtacca    420
ccagtggact ggcctacaaa gcacatagag tcctacaggc tcgcatgcac ctcactcggg    480
gcggaaaagg ttgaggtctt gcgtgccgct ttcaggtcgc gatatgcggc ctaa          534
```

<210> SEQ ID NO 165
<211> LENGTH: 465
<212> TYPE: DNA
<213> ORGANISM: Unknown Organism
<220> FEATURE:
<223> OTHER INFORMATION: Enterobacteriaceae

<400> SEQUENCE: 165

```
atgggcatca ttcgcacatg taggctcggc cctgaccaag tcaaatccat gcgggctgct     60
cttgatcttt tcggtcgtga gttcggagac gtagccacct actcccaaca tcagccggac    120
tccgattacc tcgggaactt gctccgtagt aagacattca tcgcgcttgc tgccttcgac    180
caagaagcgg ttgttggcgc tctcgcggct tacgttctgc ccaggtttga gcagccgcgt    240
agtgagatct atatctatga tctcgcagtc tccggcgagc accggaggca gggcattgcc    300
accgcgctca tcaatctcct caagcatgag gccaacgcgc ttggtgctta tgtgatctac    360
gtgcaagcag attacggtga cgatcccgca gtggctctct atacaaagtt gggcatacgg    420
gaagaagtga tgcactttga tatcgaccca agtaccgcca cctaa                    465
```

<210> SEQ ID NO 166
<211> LENGTH: 861
<212> TYPE: DNA
<213> ORGANISM: Escherichia coli

<400> SEQUENCE: 166

```
atgcatacgc ggaaggcaat aacggaggcg cttcaaaaac tcggagtcca aaccggtgac     60
ctattgatgg tgcatgcctc acttaaagcg attggtccgg tcgaaggagg agcggagacg    120
gtcgttgccg cgttacgctc cgcggttggg ccgactggca ctgtgatggg atacgcatcg    180
tgggaccgat cacctacga ggagactcgt aatggcgctc ggttggatga caaaacccgc    240
cgtacctggc cgccgttcga tcccgcaacg gccgggactt accgtgggtt cggcctgctg    300
```

| | |
|---|---|
| aatcagtttc tggttcaagc ccccggcgcg cggcgcagcg cgcaccccga tgcatcgatg | 360 |
| gtcgcggttg gtccactggc tgaaacgctg acggagcctc acaagctcgg tcacgccttg | 420 |
| ggggaagggt cgcccgtcga gcggttcgtt cgccttggcg ggaaggccct gctgttgggt | 480 |
| gcgccgctaa actccgttac cgcattgcac tacgccgagg cggttgccga tatcccaac | 540 |
| aaacggcggg tgacgtatga gatgccgatg cttggaagca acggcgaagt cgcctggaaa | 600 |
| acggcatcgg attacgattc aaacggcatt ctcgattgct ttgctatcga aggaaagccg | 660 |
| gatgcggtcg aaactatagc aaatgcttac gtgaagctcg gtcgccatcg agaaggtgtc | 720 |
| gtgggctttg ctcagtgcta cctgttcgac gcgcaggaca tcgtgacgtt cggcgtcacc | 780 |
| tatcttgaga agcatttcgg aaccactccg atcgtgccag cacacgaagt cgccgagtgc | 840 |
| tcttgcgagc cttcaggtta g | 861 |

<210> SEQ ID NO 167
<211> LENGTH: 816
<212> TYPE: DNA
<213> ORGANISM: Pseudomonas aeruginosa

<400> SEQUENCE: 167

| | |
|---|---|
| atgaccgatt tgaatatccc gcatacacac gcgcaccttg tagacgcatt tcaggcgctc | 60 |
| ggcatccgcg cggggcaggc gctcatgctg cacgcatccg ttaaagcagt gggcgcggtg | 120 |
| atgggcggcc ccaatgtgat cttgcaggcg ctcatggatg cgctcacgcc cgacggcacg | 180 |
| ctgatgatgt atgcgggatg caagacatc cccgactta tcgactcgct gccggacgcg | 240 |
| ctcaaggccg tgtatcttga gcagcaccca ccctttgacc ccgccaccgc ccgcgccgtg | 300 |
| cgcgaaaaca gcgtgctagc ggaattttg cgcacatggc cgtgcgtgca tcgcagcgca | 360 |
| aaccccgaag cctctatggt ggcggtaggc aggcaggccg ctttgctgac cgctaatcac | 420 |
| gcgctggatt atggctacgg agtcgagtcg ccgctggcta aactggtggc aatagaagga | 480 |
| tacgtgctga tgcttggcgc gccgctggat accatcacac tgctgcacca cgcggaatat | 540 |
| ctggccaaga tgcgccacaa gaacgtggtc cgctacccgt gcccgattct gcggacggg | 600 |
| cgcaaagtgt gggtgaccgt tgaggactat gacaccggtg atccgcacga cgattatagt | 660 |
| tttgagcaaa tcgcgcgcga ttatgtggcg cagggcggcg gcacacgcgg caaagtcggt | 720 |
| gatgcggatg cttacctgtt cgccgcgcag gacctcacac ggtttgcggt gcagtggctt | 780 |
| gaatcacggt tcggtgactc agcgtcatac ggatag | 816 |

<210> SEQ ID NO 168
<211> LENGTH: 498
<212> TYPE: DNA
<213> ORGANISM: Pseudomonas aeruginosa

<400> SEQUENCE: 168

| | |
|---|---|
| atgctctatg agtggctaaa tcgatctcat atcgtcgagt ggtggggcgg agaagaagca | 60 |
| cgcccgacac ttgctgacgt acaggaacag tacttgccaa gcgttttagc gcaagagtcc | 120 |
| gtcactccat acattgcaat gctgaatgga gagccgattg gtatgcccca gtcgtacgtt | 180 |
| gctcttggaa gcggggacgg atggtgggaa gaagaaaccg atccaggagt acgcggaata | 240 |
| gaccagttac tggcgaatgc atcacaactg gcaaaggct tggaaccaa gctggttcga | 300 |
| gctctggttg agttgctgtt caatgatccc gaggtcacca agatccaaac ggaccgtcg | 360 |
| ccgagcaact tgcgagcgat ccgatgctac gagaaagcgg ggtttgagag gcaaggtacc | 420 |
| gtaaccaccc cagatggtcc agccgtgtac atggttcaaa cacgccaggc attcgagcga | 480 |

```
acacgcagtg atgcctaa                                                    498
```

<210> SEQ ID NO 169
<211> LENGTH: 2007
<212> TYPE: DNA
<213> ORGANISM: Staphylococcus aureus

<400> SEQUENCE: 169

```
atgaaaaaga taaaaattgt tccacttatt ttaatagttg tagttgtcgg gtttggtata      60
tatttttatg cttcaaaaga taaagaaatt aataatacta ttgatgcaat tgaagataaa     120
aatttcaaac aagtttataa agatagcagt tatatttcta aaagcgataa tggtgaagta     180
gaaatgactg aacgtccgat aaaaatatat aatagtttag gcgttaaaga tataaacatt     240
caggatcgta aaataaaaaa agtatctaaa aataaaaaac gagtagatgc tcaatataaa     300
attaaaacaa actacggtaa cattgatcgc aacgttcaat ttaattttgt taaagaagat     360
ggtatgtgga agttagattg ggatcatagc gtcattattc caggaatgca gaaagaccaa     420
agcatacata ttgaaaattt aaaatcagaa cgtggtaaaa ttttagaccg aaacaatgtg     480
gaattggcca atacaggaac acatatgaga ttaggcatcg ttccaaagaa tgtatctaaa     540
aaagattata agcaatcgc taaagaacta agtatttctg aagactatat caacaacaaa     600
tggatcaaaa ttgggtacaa gatgatacct tcgttccact ttaaaaccgt taaaaaaatg     660
gatgaatatt taagtgattt cgcaaaaaaa tttcatctta caactaatga aacagaaagt     720
cgtaactatc ctctagaaaa agcgacttca catctattag gttatgttgg tcccattaac     780
tctgaagaat taaacaaaa agaatataaa ggctataaag atgatgcagt tattggtaaa     840
aagggactcg aaaaacttta cgataaaaag ctccaacatg aagatggcta tcgtgtcaca     900
atcgttgacg ataatagcaa tacaatcgca catacattaa tagagaaaaa gaaaaaagat     960
ggcaaagata ttcaactaac tattgatgct aaagttcaaa agagtattta taacaacatg    1020
aaaaatgatt atggctcagg tactgctatc caccctcaaa caggtgaatt attagcactt    1080
gtaagcacac cttcatatga cgtctatcca tttatgtatg gcatgagtaa cgaagaatat    1140
aataaattaa ccgaagataa aaaagaacct ctgctcaaca gttccagat tacaacttca    1200
ccaggttcaa ctcaaaaaat attaacagca atgattgggt taaataacaa aacattagac    1260
gataaaacaa gttataaaat cgatggtaaa ggttggcaaa aagataaatc ttggggtggt    1320
tacaacgtta caagatatga agtggtaaat ggtaatatcg acttaaaaca agcaatagaa    1380
tcatcagata cattttcctt tgctagagta gcactcgaat taggcagtaa gaaatttgaa    1440
aaaggcatga aaaaactagg tgttggtgaa gatataccaa gtgattatcc atttataat    1500
gctcaaattt caaacaaaaa tttagataat gaaatattat tagctgattc aggttacgga    1560
caaggtgaaa tactgattaa cccagtacag atccctttcaa tctatagcgc attagaaaat    1620
aatgcaata ttaacgcacc tcacttatta aagacacga aaacaaagt ttggaagaaa    1680
aatattattt ccaaagaaaa tatcaatcta ttaaatgatg gtatgcaaca agtcgtaaat    1740
aaaacacata agaagatat ttatagatct tatgcaaact taattggcaa atccggtact    1800
gcagaactca aaatgaaaca aggagaaagt ggcagacaaa ttgggtggtt tatatcatat    1860
gataaagata atccaaacat gatgatggct attaatgtta aagatgtaca agataaagga    1920
atggctagct acaatgccaa aatctcaggt aaagtgtatg atgagctata tgagaacggt    1980
aataaaaaat acgatataga tgaataa                                         2007
```

<210> SEQ ID NO 170

<211> LENGTH: 2607
<212> TYPE: DNA
<213> ORGANISM: Enterococcus faecium

<400> SEQUENCE: 170

```
atgaataaca tcggcattac tgtttatgga tgtgagcagg atgaggcaga tgcattccat      60
gctctttcgc ctcgctttgg cgttatggca acgataatta acgccaacgt gtcggaatcc     120
aacgccaaat ccgcgccttt caatcaatgt atcagtgtgg acataaatc agagatttcc      180
gcctctattc ttcttgcgct gaagagagcc ggtgtgaaat atattctac ccgaagcatc      240
ggctgcaatc atatagatac aactgctgct aagagaatgg gcatcactgt cgacaatgtg     300
gcgtactcgc cggatagcgt tgccgattat actatgatgc taattcttat ggcagtacgc     360
aacgtaaaat cgattgtgcg ctctgtggaa aaacatgatt tcaggttgga cagcgaccgt     420
ggcaaggtac tcagcgacat gacagttggt gtggtgggaa cgggccagat aggcaaagcg     480
gttattgagc ggctgcgagg atttggatgt aaagtgttgg cttatagtcg cagccgaagt     540
atagaggtaa actatgtacc gtttgatgag ttgctgcaaa atagcgatat cgttacgctt     600
catgtgccgc tcaatacgga tacgcactat attatcagcc acgaacaaat acagagaatg     660
aagcaaggag catttcttat caatactggg cgcggtccac ttgtagatac ctatgagttg     720
gttaaagcat tagaaaacgg gaactgggc ggtgccgcat ggatgtatt ggaaggagag       780
gaagagttt tctactctga ttgcacccaa aaaccaattg ataatcaatt tttacttaaa      840
cttcaaagaa tgcctaacgt gataatcaca ccgcatacgg cctattatac cgagcaagcg     900
ttgcgtgata ccgttgaaaa accattaaaa actgtttgg attttgaaag gagacaggag     960
catgaataga ataaaagttg caatactgtt tgggggttgc tcagaggagc atgacgtatc    1020
ggtaaaatct gcaatagaga tagccgctaa cattaataaa gaaaaatacg agccgttata   1080
cattggaatt acgaaatctg gtgtatgaa atgtgcgaa aaaccttgcg cggaatggga     1140
aaacgacaat tgctattcag ctgtactctc gccggataaa aaaatgcacg gattacttgt   1200
taaaagaac catgaatatg aaatcaacca tgttgatgta gcattttcag ctttgcatgg   1260
caagtcaggt gaagatggat ccatacaagg tctgttgaa ttgtccggta tccctttgt    1320
aggctgcgat attcaaagct cagcaatttg tatggacaaa tcgttgacat acatcgttgc   1380
gaaaaatgct gggatagcta ctcccgcctt ttgggttatt aataaagatg ataggccggt   1440
ggcagctacg tttacctatc ctgttttgt taagccggcg cgttcaggct catccttcgg    1500
tgtgaaaaaa gtcaatagcg cggacgaatt ggactacgca attgaatcgg caagacaata   1560
tgacagcaaa atcttaattg agcaggctgt ttcgggctgt gaggtcggtt gtgcggtatt   1620
gggaaacagt gccgcgttag ttgttggcga ggtggaccaa atcaggctgc agtacggaat   1680
ctttcgtatt catcaggaag tcgagccgga aaaaggctct gaaaacgcag ttataaccgt   1740
tcccgcagac ctttcagcag aggagcgagg acggatacag gaaacggcaa aaaaatata    1800
taaagcgctc ggctgtagag gtctagcccg tgtggatatg ttttttacaag ataacggccg   1860
cattgtactg aacgaagtca atactctgcc cggtttcacg tcatacagtc gttatccccg    1920
tatgatggcc gctgcaggta ttgcacttcc cgaactgatt gaccgcttga tcgtattagc    1980
gttaaagggg tgataagcat ggaaatagga tttactttt tagatgaaat agtacacgg      2040
gttcgtttgg acgctaaata tgccacttgg gataatttca ccggaaaacc ggttgacggt   2100
tatgaagtaa atcgcattgt agggacatac gagttggctg aatcgctttt gaaggcaaaa   2160
gaactggctg ctacccaagg gtacggattg cttctatggg acggttaccg tcctaagcgt   2220
```

```
gctgtaaact gttttatgca atgggctgca cagccggaaa ataacctgac aaaggaaagt    2280
tattatccca atattgaccg aactgagatg atttcaaaag gatacgtggc ttcaaaatca    2340
agccatagcc gcggcagtgc cattgatctt acgctttatc gattagacac gggtgagctt    2400
gtaccaatgg ggagccgatt tgattttatg gatgaacgct ctcatcatgc ggcaaatgga    2460
atatcatgca atgaagcgca aaatcgcaga cgtttgcgct ccatcatgga aaacagtggg    2520
tttgaagcat atagcctcga atggtggcac tatgtattaa agacgaacc atacccaat     2580 agctattttg atttccccgt taaataa                                        2607
```

<210> SEQ ID NO 171
<211> LENGTH: 1288
<212> TYPE: DNA
<213> ORGANISM: Pseudomonas aeruginosa

<400> SEQUENCE: 171

```
ggatccatca ggcaacgacg ggctgctgcc ggccatcagc ggacgcaggg aggactttcc     60
gcaaccggcc gttcgatgcg gcaccgatgg ccttcgcgca ggggtagtga atccgccagg    120
attgacttgc gctgccctac ctctcactag tgaggggcgg cagcgcatca agcggtgagc    180
gcactccggc accgccaact ttcagcacat gcgtgtaaat catcgtcgta gagacgtcgg    240
aatggccgag cagatcctgc acggttcgaa tgtcgtaacc gctgcggagc aaggccgtcg    300
cgaacgagtg gcggagggtg tgcggtgtgg cgggcttcgt gatgcctgct tgttctacgg    360 cacgttttgaa ggcgcgctga aaggtctggt catacatgtg atggcgacgc acgacaccgc    420
tccgtggatc ggtcgaatgc gtgtgctgcg caaaaaccca gaaccacggc caggaatgcc    480
cggcgcgcgg atacttccgc tcaagggcgt cgggaagcgc aacgccgctg cggccctcgg    540
cctggtcctt cagccaccat gcccgtgcac gcgacagctg ctcgcgcagg ctgggtgcca    600
agctctcggg taacatcaag gcccgatcct tggagccctt gccctcccgc acgatgatcg    660
tgccgtgatc gaaatccaga tccttgaccc gcagttgcaa accctcactg atccgcatgc    720
ccgttccata cagaagctgg gcgaacaaac gatgctcgcc ttccagaaaa ccgaggatgc    780
gaaccacttc atccggggtc agcaccaccg gcaagcgccg cgacgccga ggtcttccga     840 tctcctgaag ccagggcaga tccgtgcaca gcaccttgcc gtagaagaac agcaaggccg    900
ccaatgcctg acgatgcgtg gagaccgaaa ccttgcgctc gttcgccagc caggacagaa    960
atgcctcgac ttcgctgctg cccaaggttg ccgggtgacg cacaccgtgg aaacggatga   1020
aggcacgaac ccagtggaca taagcctgtt cggttcgtaa gctgtaatgc aagtagcgta   1080
tgcgctcacg caactggtcc agaaccttga ccgaacgcag cggtggtaac ggcgcagtgg   1140
cggttttcat ggcttgttat gactgttttt ttgtacagtc tatgcctcgg gcatccaagc   1200
agcaagcgcg ttacgccgtg ggtcgatgtt tgatgttatg gagcagcaac gatgttacgc   1260
agcagggcag tcgccctaaa acaaagtt                                      1288
```

<210> SEQ ID NO 172
<211> LENGTH: 1650
<212> TYPE: DNA
<213> ORGANISM: Pseudomonas aeruginosa

<400> SEQUENCE: 172

```
gttagatgca ctaagcacat aattgctcac agccaaacta tcaggtcaag tctgctttta     60
ttatttttaa gcgtgcataa taagccctac acaaattggg agatatatca tgaaaggctg    120 gcttttctt gttatcgcaa tagttggcga agtaatcgca acatccgcat taaaatctag    180
```

```
cgagggcttt actaagcttg cccctteegc cgttgtcata atcggttatg gcatcgcatt    240
ttattttctt tctctggttc tgaaatccat ccctgtcggt gttgcttatg cagtctggtc    300
gggactcggc gtcgtcataa ttacagccat tgcctggttg cttcatgggc aaaagcttga    360
tgcgtggggc tttgtaggta tggggctcat aattgctgcc tttttgctcg cccgatcccc    420
atcgtggaag tcgctgcgga ggccgacgcc atggtgacgg tgttcggcat tctgaatctc    480
accgaggact ccttcttcga tgagagccgg cggctagacc cgccggcgc tgtcaccgcg     540
gcgatcgaaa tgctgcgagt cggatcagac gtcgtggatg tcggaccggc cgccagccat    600
ccggacgcga ggcctgtatc gccggccgat gagatcagac gtattgcgcc gctcttagac    660
gccctgtccg atcagatgca ccgtgtttca atcgacagct ccaaccgga aaccccagcgc    720
tatgcgctca agcgcggcgt gggctacctg aacgatatcc aaggatttcc tgaccctgcg    780
ctctatcccg atattgctga ggcggactgc aggctggtgg ttatgcactc agcgcagcgg    840
gatggcatcg ccacccgcac cggtcacctt cgacccgaag acgcgctcga cgagattgtg    900
cggttcttcg aggcgcgggt ttccgccttg cgacggagcg gggtcgctgc cgaccggctc    960
atcctcgatc cggggatggg attttcttg agccccgcac cggaaacatc gctgcacgtg    1020
ctgtcgaacc ttcaaaagct gaagtcggcg ttggggcttc cgctattggt ctcggtgtcg    1080
cggaaatcct tcttgggcgc caccgttggc cttcctgtaa aggatctggg tccagcgagc    1140
cttgcggcgg aacttcacgc gatcggcaat ggcgctgact acgtccgcac ccacgcgcct    1200
ggagatctgc gaagcgcaat caccttctcg gaaaccctcg cgaaatttcg cagtcgcgac    1260
gccagagacc gagggttaga tcatgcctag cattcacctt ccggccgccc gctagcggac    1320
cctggtcagg ttccgcgaag gtgggcgcag acatgctggg ctcgtcagga tcaaactgca    1380
ctatgaggcg gcggttcata ccgcgccagg ggagcgaatg gacagcgagg agcctccgaa    1440
cgttcgggtc gcctgctcgg gtgatatcga cgaggttgtg cggctgatgc acgacgctgc    1500
ggcgtggatg tccgccaagg gaacgcccgc ctgggacgtc gcgcggatcg accggacatt    1560
cgcggagacc ttcgtcctga gatccgagct cctagtcgcg agttgcagcg acggcatcgt    1620
cggctgttgc accttgtcgg ccgaggatcc                                    1650

<210> SEQ ID NO 173
<211> LENGTH: 630
<212> TYPE: DNA
<213> ORGANISM: Enterococcus faecium

<400> SEQUENCE: 173
atgggtccga atcctatgaa atgtatcct atagaaggaa acaaatcagt acaatttatc     60
aaacctattt tagaaaaatt agaaaatgtt gaggttggag aatactcata ttatgattct    120
aagaatggag aaacttttga taagcaaatt ttatatcatt atccaatctt aaacgataag    180
ttaaaaatag gtaaattttg ctcaatagga ccaggtgtaa ctattattat gaatggagca    240
aatcatagaa tggatggctc aacatatcca tttaatttat ttggtaatgg atgggagaaa    300
catatgccaa aattagatca actacctatt aaggggata caataatagg taatgatgta    360
tggataggaa aagatgttgt aattatgcca ggagtaaaaa tcggggatgg tgcaatagta    420
gctgctaatt ctgttgttgt aaaagatata gcgccataca tgttagctgg aggaaatcct    480
gctaacgaaa taaaacaaag atttgatcaa gatacaataa atcagctgct tgatataaaa    540
tggtggaatt ggccaataga cattattaat gagaatatag ataaaattct tgataatagc    600
atcattagag aagtcatatg gaaaaaatga                                    630
```

<210> SEQ ID NO 174
<211> LENGTH: 1440
<212> TYPE: DNA
<213> ORGANISM: Enterococcus faecalis

<400> SEQUENCE: 174

```
atgaatatag ttgaaaatga aatatgtata agaactttaa tagatgatga ttttcctttg      60
atgttaaaat ggttaactga tgaaagagta ttagaatttt atggtggtag agataaaaaa     120
tatacattag aatcattaaa aaaacattat acagagcctt gggaagatga agttttttaga    180
gtaattattg aatataacaa tgttcctatt ggatatggac aaatatataa aatgtatgat     240
gagttatata ctgattatca ttatccaaaa actgatgaga gagtctatgg tatggatcaa    300
tttataggag agccaaatta ttggagtaaa ggaattggta caagatatat taaattgatt     360
tttgaatttt tgaaaaaaga aagaaatgct aatgcagtta ttttagaccc tcataaaaat     420
aatccaagag caataagggc ataccaaaaa tctggtttta gaattattga agatttgcca     480
gaacatgaat tacacgaggg caaaaaagaa gattgttatt aatggaata tagatatgat     540
gataatgcca caaatgttaa ggcaatgaaa tatttaattg agcattactt tgataatttc     600
aaagtagata gtattgaaat aatcggtagt ggttatgata gtgtggcata tttagttaat     660
aatgaataca tttttaaaac aaaatttagt actaataaga aaaaggtta tgcaaaagaa     720
aaagcaatat ataattttttt aaatacaaat ttagaaacta atgtaaaaat tcctaatatt     780
gaatattcgt atattagtga tgaattatct atactaggtt ataaagaaat taaaggaact     840
tttttaacac cagaaaattta ttctactatg tcagaagaag aacaaaattt gttaaaacga     900
gatattgcca gttttttaag acaaatgcac ggtttagatt atacagatat tagtgaatgt     960
actattgata ataaacaaaa tgtattagaa gagtatatat tgttgcgtga aactatttat    1020
aatgatttaa ctgatataga aaagattat atagaaagtt ttatgaaaag actaaatgca    1080
acaacagttt tgagggtaa aaagtgttta tgccataatg attttagttg taatcatcta    1140
ttgttagatg gcaataatag attaactgga ataattgatt ttggagattc tggaattata    1200
gatgaatatt gtgattttat atacttactt gaagatagta agaagaaat aggaacaaat    1260
tttggagaag atatattaag aatgtatgga aatatagata ttgagaaagc aaaagaatat    1320
caagatatag ttgaagaata ttatcctatt gaaactattg tttatggaat taaaaatatt    1380
aaacaggaat ttatcgaaaa tggtagaaaa gaaatttata aaaggactta taagattga    1440
```

<210> SEQ ID NO 175
<211> LENGTH: 660
<212> TYPE: DNA
<213> ORGANISM: Staphylococcus aureus

<400> SEQUENCE: 175

```
ttgaattaa acaatgacca tggacctgat cccgaaaata ttttaccgat aaaagggaat      60
cggaatcttc aatttataaa acctactata acgaacgaaa acattttggt gggaatat      120
tcttattatg atagtaagcg aggagaatcc tttgaagatc aagtcttata tcattatgaa     180
gtgattggag ataagttgat tataggaaga ttttgttcaa ttggtcccgg aacaacattt     240
attatgaatg gtgcaaacca tcggatggat ggatcaacat atcctttca tctattcagg     300
atgggttggg agaagtatat gccttcctta aaagatcttc ccttgaaagg ggacattgaa     360
attggaaatg atgtatggat aggtagagat gtaaccatta tgcctggggt gaaaattggg     420
gacggggcaa tcattgctgc agaagctgtt gtcacaaaga atgttgctcc ctattctatt     480
```

```
gtcggtggaa atcccttaaa atttataaga aaaaggtttt ctgatggagt tatcgaagaa      540
tggttagctt tacaatggtg gaatttagat atgaaaatta ttaatgaaaa tcttcccttc      600
ataataaatg gagatatcga aatgctgaag agaaaaagaa aacttctaga tgacacttga      660
```

<210> SEQ ID NO 176
<211> LENGTH: 1569
<212> TYPE: DNA
<213> ORGANISM: Staphylococcus aureus

<400> SEQUENCE: 176

```
atgaaaataa tgttagaggg acttaatata aaacattatg ttcaagatcg tttattgttg       60
aacataaatc gcctaaagat ttatcagaat gatcgtattg gtttaattgg taaaaatgga      120
agtggaaaaa caacgttact tcacatatta tataaaaaaa ttgtgcctga agaaggtatt      180
gtaaaacaat tttcacattg tgaacttatt cctcaattga agctcataga atcaactaaa      240
agtggtggtg aagtaacacg aaactatatt cggcaagcgc ttgataaaaa tccagaactg      300
ctattagcag atgaaccaac aactaactta gataataact atatagaaaa attagaacag      360
gatttaaaaa attggcatgg agcatttatt atagtttcac atgatcgcgc tttttttagat      420 aacttgtgta ctactatatg ggaaattgac gagggaagaa taactgaata taaggggaat      480
tatagtaact atgttgaaca aaaagaatta gaaagacatc gagaagaatt agaatatgaa      540
aaatatgaaa agaaaagaa acgattggaa aaagctataa atataaaaga acagaaagct      600
caacgagcaa ctaaaaaacc gaaaaactta agtttatctg aaggcaaaat aaaaggagca      660
aagccatact ttgcaggtaa gcaaaagaag ttacgaaaaa ctgtaaaatc tctagaaacc      720
agactagaaa aacttgaaag cgtcgaaaag agaaacgaac ttcctccact taaaatggat      780
ttagtgaact tagaaagtgt aaaaaaatag actataaatac gtggtgaaga tgtctcgggt      840
acaattgaag gacgggtatt gtggaaagca aaaagttta gtattcgcgg aggagacaag      900
atggcaatta tcggatctaa tggtacagga aagacaacgt ttattaaaaa aattgtgcat      960
gggaatcctg gtatttcatt atcgccatct gtcaaaatcg ttattttag ccaaaaaata     1020 gatacattag aattagataa gagcatttta gaaaatgttc aatcttcttc acaacaaaat     1080
gaaactctta ttcgaactat tctagctaga atgcattttt ttagagatga tgtttataaa     1140
ccaataagtg tcttaagtgg tggagagcga gttaaagtag cactaactaa agtattctta     1200
agtgaagtta atacgttggt actagatgaa ccaacaaact ttcttgatat ggaagctata     1260
gaggcgtttg aatctttgtt aaaggaatat aatggcagta taatctttgt atctcacgat     1320
cgtaaattta tcgaaaaagt agccactcga ataatgacaa ttgataataa agaaataaaa     1380
atatttgatg gcacatatga acaatttaaa caagctgaaa agccaacaag gaatattaaa     1440
gaagataaaa aacttttact tgagacaaaa attacagaag tactcagtcg attgagtatt     1500
gaaccttcgg aagaattaga acaagagttt caaaacttaa taaatgaaaa agaaatttg     1560 gataaataa                                                            1569
```

<210> SEQ ID NO 177
<211> LENGTH: 1467
<212> TYPE: DNA
<213> ORGANISM: Staphylococcus epidermidis

<400> SEQUENCE: 177

```
atggaacaat atacaattaa atttaaccaa atcaatcata aattgacaga tttacgatca       60
cttaacatcg atcatcttta tgcttaccaa tttgaaaaaa tagcacttat tgggggtaat      120
```

-continued

```
ggtactggta aaaccacatt actaaatatg attgctcaaa aaacaaaacc agaatctgga      180
acagttgaaa cgaatggcga aattcaatat tttgaacagc ttaacatgga tgtggaaaat      240
gattttaaca cgttagacgg tagtttaatg agtgaactcc atatacctat gcatacaacc      300
gacagtatga gtggtggtga aaaagcaaaa tataaattac gtaatgtcat atcaaattat      360
agtccgatat tacttttaga tgaacctaca aatcacttgg ataaaattgg taaagattat      420
ctgaataata ttttaaaata ttactatggt actttaatta tagtaagtca cgatagagca      480
cttatagacc aaattgctga cacaatttgg gatatacaag aagatggcac aataagagtg      540
tttaaaggta attacacaca gtatcaaaat caatatgaac aagaacagtt agaacaacaa      600
cgtaaatatg aacagtatat aagtgaaaaa caaagattgt cccaagccag taaagctaaa      660
cgaaatcaag cgcaacaaat ggcacaagca tcatcaaaac aaaaaaataa aagtatagca      720
ccagatcgtt taagtgcatc aaaagaaaaa ggcacggttg agaaggctgc tcaaaaacaa      780
gctaagcata ttgaaaaaag aatggaacat ttggaagaag ttgaaaaacc acaaagttat      840
catgaattca attttccaca aaataaaatt tatgatatcc ataataatta tccaatcatt      900
gcacaaaatc taacattggt taaggaagt caaaaactgc taacacaagt acgattccaa      960
ataccatatg gcaaaaatat agcgctcgta ggtgcaaatg gtgtaggtaa gacaacttta     1020
cttgaagcta tttaccacca aatagaggga attgattgtt ctcctaaagt gcaaatggca     1080
tactatcgtc aacttgctta tgaagacatg cgtgacgttt cattattgca atatttaatg     1140
gatgaaacgg attcatcaga atcattcagt agagctattt taaataactt gggtttaaat     1200
gaagcacttg agcgttcttg taatgttttg agtggtgggg aaagaacgaa attatcgtta     1260
gcagtattat tttcaacgaa agcgaatatg ttaattttgg atgaaccaac taattttta     1320 gatattaaaa cattagaagc attagaaatg tttatgaata aatatcctgg aatcattttg     1380
tttacatcac atgatacaag gtttgttaaa catgtatcag ataaaaaatg ggaattaaca     1440
ggacaatcta ttcatgatat aacttaa                                         1467
```

PROBES AND PRIMERS FOR DETECTION OF BACTERIAL PATHOGENS AND ANTIBIOTIC RESISTANCE GENES

CROSS-REFERENCE TO RELATED APPLICATIONS

This application is a continuation of U.S. patent application Ser. No. 10/121,120 to Bergeron et al., entitled "Specific and universal probes and amplification primers to rapidly detect and identify common bacterial pathogens and antibiotic resistance genes from clinical specimens for routine diagnosis in microbiology laboratories," filed Apr. 11, 2002, which is a continuation of U.S. patent application Ser. No. 09/452,599, filed Dec. 1, 1999, now abandoned, which is a continuation of U.S. patent application Ser. No. 08/526,840, filed Sep. 11, 1995, now U.S. Pat. No. 6,001,564, which is a continuation-in-part of U.S. patent application Ser. No. 08/304,732, filed Sep. 12, 1994, now abandoned.

REFERENCE TO SEQUENCE LISTING, TABLE, OR COMPUTER PROGRAM LISTING

The present application is being filed along with duplicate copies of a CD-ROM marked "Copy 1" and "Copy 2" containing a Sequence Listing in electronic format. The duplicate copies of CD-ROM entitled The "Copy 1" and "Copy 2" each contains a file entitled GENOM.046CP1CCC.txt created on May 1, 2006 which is 125,952 Bytes in size. The information on these duplicate CD-ROMs is incorporated herein by reference in its entirety.

BACKGROUND OF THE INVENTION

Classical Identification of Bacteria

Bacteria are classically identified by their ability to utilize different substrates as a source of carbon and nitrogen through the use of biochemical tests such as the API20E™ system. Susceptibility testing of Gram negative bacilli has progressed to microdilution tests. Although the API and the microdilution systems are cost-effective, at least two days are required to obtain preliminary results due to the necessity of two successive overnight incubations to isolate and identify the bacteria from the specimen. Some faster detection methods with sophisticated and expensive apparatus have been developed. For example, the fastest identification system, the autoSCAN-Walk-Away system™ identifies both Gram negative and Gram positive from isolated bacterial colonies in 2 hours and susceptibility patterns to antibiotics in only 7 hours. However, this system has an unacceptable margin of error, especially with bacterial species other than Enterobacteriaceae (York et al., 1992. J. Clin. Microbiol. 30:2903-2910). Nevertheless, even this fastest method requires primary isolation of the bacteria as a pure culture, a process which takes at least 18 hours if there is a pure culture or 2 to 3 days if there is a mixed culture.

Urine Specimens

A large proportion (40-50%) of specimens received in routine diagnostic microbiology laboratories for bacterial identification are urine specimens (Pezzlo, 1988, Clin. Microbiol. Rev. 1:268-280). Urinary tract infections (UTI) are extremely common and affect up to 20% of women and account for extensive morbidity and increased mortality among hospitalized patients (Johnson and Stamm, 1989; Ann. Intern. Med. 111:906-917). UTI are usually of bacterial etiology and require antimicrobial therapy. The Gram negative bacillus Escherichia coli is by far the most prevalent urinary pathogen and accounts for 50 to 60% of UTI (Pezzlo, 1988, op. cit.). The prevalence for bacterial pathogens isolated from urine specimens observed recently at the "Centre Hospitalier de l'Universit Laval (CHUL)" is given in Tables 1 and 2.

Conventional pathogen identification in urine specimens. The search for pathogens in urine specimens is so preponderant in the routine microbiology laboratory that a myriad of tests have been developed. The gold standard is still the classical semi-quantitative plate culture method in which a calibrated loop of urine is streaked on plates and incubated for 18-24 hours. Colonies are then counted to determine the total number of colony forming units (CFU) per liter of urine. A bacterial UTI is normally associated with a bacterial count of .gtoreq.10.sup.7 CFU/L in urine. However, infections with less than 10.sup.7 CFU/L in urine are possible, particularly in patients with a high incidence of diseases or those catheterized (Stark and Maki, 1984, N. Engl. J. Med. 311:560-564). Importantly, close to 80% of urine specimens tested are considered negative (<10.sup.7 CFU/L; Table 3).

Accurate and rapid urine screening methods for bacterial pathogens would allow a faster identification of negative results and a more efficient clinical investigation of the patient. Several rapid identification methods (Uriscreen™, UTIscreen™, Flash Track™ DNA probes and others) were recently compared to slower standard biochemical methods which are based on culture of the bacterial pathogens. Although much faster, these rapid tests showed low sensitivities and specificities as well as a high number of false negative and false positive results (Koening et al., 1992. J. Clin. Microbiol. 30:342-345; Pezzlo et al., 1992. J. Clin. Microbiol. 30:640-684).

Urine specimens found positive by culture are further characterized using standard biochemical tests to identify the bacterial pathogen and are also tested for susceptibility to antibiotics.

Any Clinical Specimens

As with urine specimen which was used here as an example, our probes and amplification primers are also applicable to any other clinical specimens. The DNA-based tests proposed in this invention are superior to standard methods currently used for routine diagnosis in terms of rapidity and accuracy. While a high percentage of urine specimens are negative, in many other clinical specimens more than 95% of cultures are negative (Table 4). These data further support the use of universal probes to screen out the negative clinical specimens. Clinical specimens from organisms other than humans (e.g. other primates, mammals, farm animals or live stocks) may also be used.

Towards the Development of Rapid DNA-based Diagnostic

A rapid diagnostic test should have a significant impact on the management of infections. For the identification of pathogens and antibiotic resistance genes in clinical samples, DNA probe and DNA amplification technologies offer several advantages over conventional methods. There is no need for subculturing, hence the organism can be detected directly in clinical samples thereby reducing the costs and time associated with isolation of pathogens. DNA-based technologies have proven to be extremely useful for specific applications in the clinical microbiology laboratory. For example, kits for the detection of fastidious organisms based on the use of hybridization probes or DNA amplification for the direct detection of pathogens in clinical specimens are commercially available (Persing et al, 1993. Diagnostic Molecular Microbiology: Principles and Applications, American Society for Microbiology, Washington, D.C.).

The present invention is an advantageous alternative to the conventional culture identification methods used in hospital clinical microbiology laboratories and in private clinics for routine diagnosis. Besides being much faster, DNA-based diagnostic tests are more accurate than standard biochemical tests presently used for diagnosis because the bacterial genotype (e.g. DNA level) is more stable than the bacterial phenotype (e.g. biochemical properties). The originality of this invention is that genomic DNA fragments (size of at least 100 base pairs) specific for 12 species of commonly encountered bacterial pathogens were selected from genomic libraries or from data banks. Amplification primers or oligonucleotide probes (both less than 100 nucleotides in length) which are both derived from the sequence of species-specific DNA fragments identified by hybridization from genomic libraries or from selected data bank sequences are used as a basis to develop diagnostic tests. Oligonucleotide primers and probes for the detection of commonly encountered and clinically important bacterial resistance genes are also included. For example, Annexes I and II present a list of suitable oligonucleotide probes and PCR primers which were all derived from the species-specific DNA fragments selected from genomic libraries or from data bank sequences. It is clear to the individual skilled in the art that oligonucleotide sequences appropriate for the specific detection of the above bacterial species other than those listed in Annexes 1 and 2 may be derived from the species-specific fragments or from the selected data bank sequences. For example, the oligonucleotides may be shorter or longer than the ones we have chosen and may be selected anywhere else in the identified species-specific sequences or selected data bank sequences. Alternatively, the oligonucleotides may be designed for use in amplification methods other than PCR. Consequently, the core of this invention is the identification of species-specific genomic DNA fragments from bacterial genomic DNA libraries and the selection of genomic DNA fragments from data bank sequences which are used as a source of species-specific and ubiquitous oligonucleotides. Although the selection of oligonucleotides suitable for diagnostic purposes from the sequence of the species-specific fragments or from the selected data bank sequences requires much effort it is quite possible for the individual skilled in the art to derive from our fragments or selected data bank sequences suitable oligonucleotides which are different from the ones we have selected and tested as examples (Annexes I and II).

Others have developed DNA-based tests for the detection and identification of some of the bacterial pathogens for which we have identified species-specific sequences (PCT patent application Ser. No. WO 93/03186). However, their strategy was based on the amplification of the highly conserved 16S rRNA gene followed by hybridization with internal species-specific oligonucleotides. The strategy from this invention is much simpler and more rapid because it allows the direct amplification of species-specific targets using oligonucleotides derived from the species-specific bacterial genomic DNA fragments.

Since a high percentage of clinical specimens are negative, oligonucleotide primers and probes were selected from the highly conserved 16S or 23S rRNA genes to detect all bacterial pathogens possibly encountered in clinical specimens in order to determine whether a clinical specimen is infected or not. This strategy allows rapid screening out of the numerous negative clinical specimens submitted for bacteriological testing.

We are also developing other DNA-based tests, to be performed simultaneously with bacterial identification, to determine rapidly the putative bacterial susceptibility to antibiotics by targeting commonly encountered and clinically relevant bacterial resistance genes. Although the sequences from the selected antibiotic resistance genes are available and have been used to develop DNA-based tests for their detection (Ehrlich and Greenberg, 1994. PCR-based Diagnostics in Infectious Diseases, Blackwell Scientific Publications, Boston, Mass.; Persing et al, 1993. Diagnostic Molecular Microbiology: Principles and Applications, American Society for Microbiology, Washington, D.C.), our approach is innovative as it represents major improvements over current "gold standard" diagnostic methods based on culture of the bacteria because it allows the rapid identification of the presence of a specific bacterial pathogen and evaluation of its susceptibility to antibiotics directly from the clinical specimens within one hour.

We believe that the rapid and simple diagnostic tests not based on cultivation of the bacteria that we are developing will gradually replace the slow conventional bacterial identification methods presently used in hospital clinical microbiology laboratories and in private clinics. In our opinion, these rapid DNA-based diagnostic tests for severe and common bacterial pathogens and antibiotic resistance will (i) save lives by optimizing treatment, (ii) diminish antibiotic resistance by reducing the use of broad spectrum antibiotics and (iii) decrease overall health costs by preventing or shortening hospitalizations.

SUMMARY OF THE INVENTION

In accordance with the present invention, there is provided sequence from genomic DNA fragments (size of at least 100 base pairs and all described in the sequence listing) selected either by hybridization from genomic libraries or from data banks and which are specific for the detection of commonly encountered bacterial pathogens (i.e. *Escherichia coli, Klebsiella pneumoniae, Pseudomonas aeruginosa, Proteus mirabilis, Streptococcus pneumoniae, Staphylococcus aureus, Staphylococcus epidermidis, Enterococcus faecalis, Staphylococcus saprophyticus, Streptococcus pyogenes, Haemophilus influenzae* and *Moraxella catarrhalis*) in clinical specimens. These bacterial species are associated with approximately 90% of urinary tract infections and with a high percentage of other severe infections including septicemia, meningitis, pneumonia, intraabdominal infections, skin infections and many other severe respiratory tract infections. Overall, the above bacterial species may account for up to 80% of bacterial pathogens isolated in routine microbiology laboratories.

Synthetic oligonucleotides for hybridization (probes) or DNA amplification (primers) were derived from the above species-specific DNA fragments (ranging in sizes from 0.25 to 5.0 kilobase pairs (kbp)) or from selected data bank sequences (GenBank and EMBL). Bacterial species for which some of the oligonucleotide probes and amplification primers were derived from selected data bank sequences are *Escherichia coli, Enterococcus faecalis, Streptococcus pyogenes* and *Pseudomonas aeruginosa*. The person skilled in the art understands that the important innovation in this invention is the identification of the species-specific DNA fragments selected either from bacterial genomic libraries by hybridization or from data bank sequences. The selection of oligonucleotides from these fragments suitable for diagnostic purposes is also innovative. Specific and ubiquitous oligonucleotides different from the ones tested in the practice are considered as embodiments of the present invention.

The development of hybridization (with either fragment or oligonucleotide probes) or of DNA amplification protocols for the detection of pathogens from clinical specimens renders possible a very rapid bacterial identification. This will greatly reduce the time currently required for the identification of pathogens in the clinical laboratory since these technologies can be applied for bacterial detection and identification directly from clinical specimens with minimum pretreatment of any biological specimens to release bacterial DNA. In addition to being 100% specific, probes and amplification primers allow identification of the bacterial species directly from clinical specimens or, alternatively, from an isolated colony. DNA amplification assays have the added advantages of being faster and more sensitive than hybridization assays, since they allow rapid and exponential in vitro replication of the target segment of DNA from the bacterial genome. Universal probes and amplification primers selected from the 16S or 23S rRNA genes highly conserved among bacteria, which permit the detection of any bacterial pathogens, will serve as a procedure to screen out the numerous negative clinical specimens received in diagnostic laboratories. The use of oligonucleotide probes or primers complementary to characterized bacterial genes encoding resistance to antibiotics to identify commonly encountered and clinically important resistance genes is also under the scope of this invention.

DETAILED DESCRIPTION OF THE PREFERRED EMBODIMENT

Development of Species-specific DNA Probes

DNA fragment probes were developed for the following bacterial species: *Escherichia coli, Klebsiella pneumoniae, Pseudomonas aeruginosa, Proteus mirabilis, Streptococcus pneumoniae, Staphylococcus aureus, Staphylococcus epidermidis, Staphylococcus saprophyticus, Haemophilus influenzae* and *Moraxella catarrhalis*. (For *Enterococcus faecalis* and *Streptococcus pyogenes*, oligonucleotide sequences were exclusively derived from selected data bank sequences). These species-specific fragments were selected from bacterial genomic libraries by hybridization to DNA from a variety of Gram positive and Gram negative bacterial species (Table 5).

The chromosomal DNA from each bacterial species for which probes were seeked was isolated using standard methods. DNA was digested with a frequently cutting restriction enzyme such as Sau3AI and then ligated into the bacterial plasmid vector pGEM3Zf (Promega) linearized by appropriate restriction endonuclease digestion. Recombinant plasmids were then used to transform competent *E. coli* strain DH5α thereby yielding a genomic library. The plasmid content of the transformed bacterial cells was analyzed using standard methods. DNA fragments of target bacteria ranging in size from 0.25 to 5.0 kilobase pairs (kbp) were cut out from the vector by digestion of the recombinant plasmid with various restriction endonucleases. The insert was separated from the vector by agarose gel electrophoresis and purified in low melting point agarose gels. Each of the purified fragments of bacterial genomic DNA was then used as a probe for specificity tests.

For each given species, the gel-purified restriction fragments of unknown coding potential were labeled with the radioactive nucleotide $\alpha 32P(dATP)$ which was incorporated into the DNA fragment by the random priming labeling reaction. Non-radioactive modified nucleotides could also be incorporated into the DNA by this method to serve as a label.

Each DNA fragment probe (i.e. a segment of bacterial genomic DNA of at least 100 bp in length cut out from clones randomly selected from the genomic library) was then tested for its specificity by hybridization to DNAs from a variety of bacterial species (Table 5). The double-stranded labeled DNA probe was heat-denatured to yield labeled single-stranded DNA which could then hybridize to any single-stranded target DNA fixed onto a solid support or in solution. The target DNAs consisted of total cellular DNA from an array of bacterial species found in clinical samples (Table 5). Each target DNA was released from the bacterial cells and denatured by conventional methods and then irreversibly fixed onto a solid support (e.g. nylon or nitrocellulose membranes) or free in solution. The fixed single-stranded target DNAs were then hybridized with the single-stranded probe. Pre-hybridization, hybridization and post-hybridization conditions were as follows: (i) Pre-hybridization; in 1 M NaCl+10% dextran sulfate+1% SDS (sodium dodecyl sulfate)+1.mu.g/ml salmon sperm DNA at 650.degree. C. for 15 min. (ii) Hybridization; in fresh pre-hybridization solution containing the labeled probe at 650.degree. C. overnight. (iii) Post-hybridization; washes twice in 3.times.SSC containing 1% SDS (1.times.SSC is 0.15M NaCl, 0.015M NaCitrate) and twice in 0.1.times.SSC containing 0.1% SDS; all washes were at 650.degree. C. for 15 min. Autoradiography of washed filters allowed the detection of selectively hybridized probes. Hybridization of the probe to a specific target DNA indicated a high degree of similarity between the nucleotide sequence of these two DNAs. Species-specific DNA fragments selected from various bacterial genomic libraries ranging in size from 0.25 to 5.0 kbp were isolated for 10 common bacterial pathogens (Table 6) based on hybridization to chromosomal DNAs from a variety of bacteria performed as described above. All of the bacterial species tested (66 species listed in Table 5) were likely to be pathogens associated with common infections or potential contaminants which can be isolated from clinical specimens. A DNA fragment probe was considered specific only when it hybridized solely to the pathogen from which it was isolated. DNA fragment probes found to be specific were subsequently tested for their ubiquity (i.e. ubiquitous probes recognized most isolates of the target species) by hybridization to bacterial DNAs from approximately 10 to 80 clinical isolates of the species of interest (Table 6). The DNAs were denatured, fixed onto nylon membranes and hybridized as described above.

Sequencing of the Species-Specific Fragment Probes

The nucleotide sequence of the totality or of a portion of the species-specific DNA fragments isolated (Table 6) was determined using the dideoxynucleotide termination sequencing method which was performed using Sequenase™ (USB Biochemicals) or T7 DNA polymerase (Pharmacia). These nucleotide sequences are shown in the sequence listing. Alternatively, sequences selected from data banks (GenBank and EMBL) were used as sources of oligonucleotides for diagnostic purposes for *Escherichia coli, Enterococcus faecalis, Streptococcus pyogenes* and *Pseudomonas aeruginosa*. For this strategy, an array of suitable oligonucleotide primers or probes derived from a variety of genomic DNA fragments (size of more than 100 bp) selected from data banks was tested for their specificity and ubiquity in PCR and hybridization assays as described later. It is important to note that the data bank sequences were selected based on their potential of being species-specific according to available sequence information. Only data bank sequences from which species-specific oligonucleotides could be derived are included in this invention.

Oligonucleotide probes and amplification primers derived from species-specific fragments selected from the genomic libraries or from data bank sequences were synthesized using an automated DNA synthesizer (Millipore). Prior to synthesis, all oligonucleotides (probes for hybridization and primers for DNA amplification) were evaluated for their suitability for hybridization or DNA amplification by polymerase chain reaction (PCR) by computer analysis using standard programs (e.g. Genetics Computer Group (GCG) and Oligo™ 4.0 (National Biosciences)). The potential suitability of the PCR primer pairs was also evaluated prior to the synthesis by verifying the absence of unwanted features such as long stretches of one nucleotide, a high proportion of G or C residues at the 3' end and a 3'-terminal T residue (Persing et al, 1993. Diagnostic Molecular Microbiology: Principles and Applications, American Society for Microbiology, Washington, D.C.).

Hybridization with Oligonucleotide Probes

In hybridization experiments, oligonucleotides (size less than 100 nucleotides) have some advantages over DNA fragment probes for the detection of bacteria such as ease of preparation in large quantities, consistency in results from batch to batch and chemical stability. Briefly, for the hybridizations, oligonucleotides were 5' end-labeled with the radionucleotide $^\gamma$32P(ATP) using T4 polynucleotide kinase (Pharmacia). The unincorporated radionucleotide was removed by passing the labeled single-stranded oligonucleotide through a Sephadex G50 column. Alternatively, oligonucleotides were labeled with biotin, either enzymatically at their 3' ends or incorporated directly during synthesis at their 5' ends, or with digoxigenin. It will be appreciated by the person skilled in the art that labeling means other than the three above labels may be used.

The target DNA was denatured, fixed onto a solid support and hybridized as previously described for the DNA fragment probes. Conditions for pre-hybridization and hybridization were as described earlier. Post-hybridization washing conditions were as follows: twice in 3×SSC containing 1% SDS, twice in 2×SSC containing 1% SDS and twice in 1×SSC containing 1% SDS (all of these washes were at 65° C. for 15 min), and a final wash in 0.1×SSC containing 1% SDS at 25° C. for 15 min. For probes labeled with radioactive labels the detection of hybrids was by autoradiography as described earlier. For non-radioactive labels detection may be calorimetric or by chemiluminescence.

The oligonucleotide probes may be derived from either strand of the duplex DNA. The probes may consist of the bases A, G, C, or T or analogs. The probes may be of any suitable length and may be selected anywhere within the species-specific genomic DNA fragments selected from the genomic libraries or from data bank sequences.

DNA Amplification

For DNA amplification by the widely used PCR (polymerase chain reaction) method, primer pairs were derived either from the sequenced species-specific DNA fragments or from data bank sequences or, alternatively, were shortened versions of oligonucleotide probes. Prior to synthesis, the potential primer pairs were analyzed by using the program oligo™ 4.0 (National Biosciences) to verify that they are likely candidates for PCR amplifications.

During DNA amplification by PCR, two oligonucleotide primers binding respectively to each strand of the denatured double-stranded target DNA from the bacterial genome are used to amplify exponentially in vitro the target DNA by successive thermal cycles allowing denaturation of the DNA, annealing of the primers and synthesis of new targets at each cycle (Persing et al, 1993. Diagnostic Molecular Microbiology: Principles and Applications, American Society for Microbiology, Washington, D.C.). Briefly, the PCR protocols were as follows. Clinical specimens or bacterial colonies were added directly to the 50 µL PCR reaction mixtures containing 50 mM KCl, 10 mM Tris-HCl pH 8.3, 2.5 mM $MgCl_2$, 0.4 µM of each of the two primers, 200 µM of each of the four dNTPs and 1.25 Units of Taq DNA polymerase (Perkin Elmer). PCR reactions were then subjected to thermal cycling (3 min at 95°0 C. followed by 30 cycles of 1 second at 95° C. and 1 second at 55° C.) using a Perkin Elmer 480™ thermal cycler and subsequently analyzed by standard ethidium bromide-stained agarose gel electrophoresis. It is clear that other methods for the detection of specific amplification products, which may be faster and more practical for routine diagnosis, may be used. Such methods may be based on the detection of fluorescence after amplification (e.g. Taq-Man™ system from Perkin Elmer or Amplisensor™ from Biotronics) or liquid hybridization with an oligonucleotide probe binding to internal sequences of the specific amplification product. These novel probes can be generated from our species-specific fragment probes. Methods based on the detection of fluorescence are particularly promising for utilization in routine diagnosis as they are, very rapid and quantitative and can be automated.

To assure PCR efficiency, glycerol or dimethyl sulfoxide (DMSO) or other related solvents, can be used to increase the sensitivity of the PCR and to overcome problems associated with the amplification of target with a high GC content or with strong secondary structures. The concentration ranges for glycerol and DMSO are 5-15% (v/v) and 3-10% (v.backslash.v), respectively. For the PCR reaction mixture, the concentration ranges for the amplification primers and the $MgCl_2$ are 0.1-1.0 µM and 1.5-3.5 mM, respectively. Modifications of the standard PCR protocol using external and nested primers (i.e. nested PCR) or using more than one primer pair (i.e. multiplex PCR) may also be used (Persing et al, 1993. Diagnostic Molecular Microbiology: Principles and Applications, American Society for Microbiology, Washington, D.C.). For more details about the PCR protocols and amplicon detection methods see examples 7 and 8.

The person skilled in the art of DNA amplification knows the existence of other rapid amplification procedures such as ligase chain reaction (LCR), transcription-based amplification systems (TAS), self-sustained sequence replication (3SR), nucleic acid sequence-based amplification (NASBA), strand displacement amplification (SDA) and branched DNA (bDNA) (Persing et al, 1993. Diagnostic Molecular Microbiology: Principles and Applications, American Society for Microbiology, Washington, D.C.). The scope of this invention is not limited to the use of amplification by PCR, but rather includes the use of any rapid nucleic acid amplification methods or any other procedures which may be used to increase rapidity and sensitivity of the tests. Any oligonucleotides suitable for the amplification of nucleic acid by approaches other than PCR and derived from the species-specific fragments and from selected antibiotic resistance gene sequences included in this document are also under the scope of this invention.

Specificity and Ubiquity Tests for Oligonucleotide Probes and Primers

The specificity of oligonucleotide probes, derived either from the sequenced species-specific fragments or from data bank sequences, was tested by hybridization to DNAs from the array of bacterial species listed in Table 5 as previously described. Oligonucleotides found to be specific were subsequently tested for their ubiquity by hybridization to bacterial DNAs from approximately 80 isolates of the target species as described for fragment probes. Probes were considered ubiquitous when they hybridized specifically with the DNA from at least 80% of the isolates. Results for specificity and ubiquity tests with the oligonucleotide probes are summarized in Table 6. The specificity and ubiquity of the amplification primer pairs were tested directly from cultures (see example 7) of the same bacterial strains. For specificity and ubiquity tests, PCR assays were performed directly from bacterial colonies of approximately 80 isolates of the target species. Results are summarized in Table 7. All specific and ubiquitous oligonucleotide probes and amplification primers for each of the 12 bacterial species investigated are listed in Annexes I and II, respectively. Divergence in the sequenced DNA fragments can occur and, insofar as the divergence of these sequences or a part thereof does not affect the specificity of the probes or amplification primers, variant bacterial DNA is under the scope of this invention.

Universal Bacterial Detection

In the routine microbiology laboratory a high percentage of clinical specimens sent for bacterial identification is negative (Table 4). For example, over a 2 year period, around 80% of urine specimens received by the laboratory at the "Centre Hospitalier de l'Université Laval (CHUL)" were negative (i.e. <$10^7$ CFU/L) (Table 3). Testing clinical samples with universal probes or universal amplification primers to detect the presence of bacteria prior to specific identification and screen out the numerous negative specimens is thus useful as it saves costs and may rapidly orient the clinical management of the patients. Several oligonucleotides and amplification primers were therefore synthesized from highly conserved portions of bacterial 16S or 23S ribosomal RNA gene sequences available in data banks (Annexes III and IV). In hybridization tests, a pool of seven oligonucleotides (Annex I; Table 6) hybridized strongly to DNA from all bacterial species listed in Table 5. This pool of universal probes labeled with radionucleotides or with any other modified nucleotides is consequently very useful for detection of bacteria in urine samples with a sensitivity range of $\geq 10^7$ CFU/L. These probes can also be applied for bacterial detection in other clinical samples.

Amplification primers also derived from the sequence of highly conserved ribosomal RNA genes were used as an alternative strategy for universal bacterial detection directly from clinical specimens (Annex IV; Table 7). The DNA amplification strategy was developed to increase the sensitivity and the rapidity of the test. This amplification test was ubiquitous since it specifically amplified DNA from 23 different bacterial species encountered in clinical specimens.

Well-conserved bacterial genes other than ribosomal RNA genes could also be good candidates for universal bacterial detection directly from clinical specimens. Such genes may be associated with processes essential for bacterial survival (e.g. protein synthesis, DNA synthesis, cell division or DNA repair) and could therefore be highly conserved during evolution. We are working on these candidate genes to develop new rapid tests for the universal detection of bacteria directly from clinical specimens.

Antibiotic Resistance Genes

Antimicrobial resistance complicates treatment and often leads to therapeutic failures. Furthermore, overuse of antibiotics inevitably leads to the emergence of bacterial resistance. Our goal is to provide the clinicians, within one hour, the needed information to prescribe optimal treatments. Besides the rapid identification of negative clinical specimens with DNA-based tests for universal bacterial detection and the identification of the presence of a specific pathogen in the positive specimens with DNA-based tests for specific bacterial detection, the clinicians also need timely information about the ability of the bacterial pathogen to resist antibiotic treatments. We feel that the most efficient strategy to evaluate rapidly bacterial resistance to antimicrobials is to detect directly from the clinical specimens the most common and important antibiotic resistance genes (i.e. DNA-based tests for the detection of antibiotic resitance genes). Since the sequence from the most important and common bacterial antibiotic resistance genes are available from data banks, our strategy is to use the sequence from a portion or from the entire gene to design specific oligonucleotides which will be used as a basis for the development of rapid DNA-based tests. The sequence from the bacterial antibiotic resistance genes selected on the basis of their clinical relevance (i.e. high incidence and importance) is given in the sequence listing. Table 8 summarizes some characteristics of the selected antibiotic resistance genes.

EXAMPLES

The following examples are intended to be illustrative of the various methods and compounds of the invention.

Example 1

Isolation and cloning of fragments. Genomic DNAs from *Escherichia coli* strain ATCC 25922, *Klebsiella pneumoniae* strain CK2, *Pseudomonas aeruginosa* strain ATCC 27853, *Proteus mirabilis* strain ATCC 35657, *Streptococcus pneumoniae* strain ATCC 27336, *Staphylococcus aureus* strain ATCC 25923, *Staphylococcus epidermidis* strain ATCC 12228, *Staphylococcus saprophyticus* strain ATCC 15305, *Haemophilus influenzae* reference strain Rd and *Moraxella catarrhalis* strain ATCC 53879 were prepared using standard procedures. It is understood that the bacterial genomic DNA may have been isolated from strains other than the ones mentioned above. (For *Enterococcus faecalis* and *Streptococcus pyogenes* oligonucleotide sequences were derived exclusively from data banks). Each DNA was digested with a restriction enzyme which frequently cuts DNA such as Sau3AI. The resulting DNA fragments were ligated into a plasmid vector (pGEM3Zf) to create recombinant plasmids and transformed into competent *E. coli* cells (DH5α). It is understood that the vectors and corresponding competent cells should not be limited to the ones herein above specifically exemplified. The objective of obtaining recombinant plasmids and transformed cells is to provide an easily reproducible source of DNA fragments useful as probes. Therefore, insofar as the inserted fragments are specific and selective for the target bacterial DNA, any recombinant plasmids and corresponding transformed host cells are under the scope of this invention. The plasmid content of the transformed bacterial cells was analyzed using standard methods. DNA fragments from target bacteria ranging in size from 0.25 to 5.0 kbp were cut out from the vector by digestion of the recombinant plasmid with various restriction endonucleases. The insert was separated from the vector by agarose gel electrophoresis and purified in a low melting point agarose gel. Each of the purified fragments was then used for specificity tests.

Labeling of DNA fragment probes. The label used was $^{\alpha}32P$(dATP), a radioactive nucleotide which can be incorporated enzymatically into a double-stranded DNA molecule. The fragment of interest is first denatured by heating at 95° C. for 5 min, then a mixture of random primers is allowed to anneal to the strands of the fragments. These primers, once annealed, provide a starting point for synthesis of DNA. DNA polymerase, usually the Klenow fragment, is provided along with the four nucleotides, one of which is radioactive. When the reaction is terminated, the mixture of new DNA molecules is once again denatured to provide radioactive single-stranded DNA molecules (i.e. the probe). As mentioned earlier, other modified nucleotides may be used to label the probes.

Specificity and ubiquity tests for the DNA fragment probes. Species-specific DNA fragments ranging in size from 0.25 to 5.0 kbp were isolated for 10 common bacterial pathogens (Table 6) based on hybridization to chromosomal DNAs from a variety of bacteria. Samples of whole cell DNA for each bacterial strain listed in Table 5 were transferred onto a nylon membrane using a dot blot apparatus, washed and denatured before being irreversibly fixed. Hybridization conditions were as described earlier. A DNA fragment probe was considered specific only when it hybridized solely to the pathogen from which it was isolated. Labeled DNA fragments hybridizing specifically only to target bacterial species (i.e. specific) were then tested for their ubiquity by hybridization to DNAs from approximately 10 to 80 isolates of the species of interest as described earlier. The conditions for pre-hybridization, hybridization and post-hybridization washes were as described earlier. After autoradiography (or other detection means appropriate for the non-radioactive label used), the specificity of each individual probe can be determined. Each probe found to be specific (i.e. hybridizing only to the DNA from the bacterial species from which it was isolated) and ubiquitous (i.e. hybridizing to most isolates of the target species) was kept for further experimentations.

Example 2

Same as example 1 except that testing of the strains is by colony hybridization. The bacterial strains were inoculated onto a nylon membrane placed on nutrient agar. The membranes were incubated at 37° C. for two hours and then bacterial lysis and DNA denaturation were carried out according to standard procedures. DNA hybridization was performed as described earlier.

Example 3

Same as example 1 except that bacteria were detected directly from clinical samples. Any biological samples were loaded directly onto a dot blot apparatus and cells were lysed in situ for bacterial detection. Blood samples should be heparizined in order to avoid coagulation interfering with their convenient loading on a dot blot apparatus.

Example 4

Nucleotide sequencing of DNA fragments. The nucleotide sequence of the totality or a portion of each fragment found to be specific and ubiquitous (Example 1) was determined using the dideoxynucleotide termination sequencing method (Sanger et al., 1977, Proc. Natl. Acad. Sci. USA. 74:5463-5467). These DNA sequences are shown in the sequence listing. Oligonucleotide probes and amplification primers were selected from these nucleotide sequences, or alternatively, from selected data banks sequences and were then synthesized on an automated Biosearch synthesizer (Millipore™) using phosphoramidite chemistry.

Labeling of oliaonucleotides. Each oligonucleotide was 5' end-labeled with $\gamma$32P-ATP by the T4 polynucleotide kinase (Pharmacia) as described earlier. The label could also be non-radioactive.

Specificity test for oligonucleotide probes. All labeled oligonucleotide probes were tested for their specificity by hybridization to DNAs from a variety of Gram positive and Gram negative bacterial species as described earlier. Species-specific probes were those hybridizing only to DNA from the bacterial species from which it was isolated. Oligonucleotide probes found to be specific were submitted to ubiquity tests as follows.

Ubiquity test for oligonucleotide probes. Specific oligonucleotide probes were then used in ubiquity tests with approximately 80 strains of the target species. Chromosomal DNAs from the isolates were transferred onto nylon membranes and hybridized with labeled oligonucleotide probes as described for specificity tests. The batteries of approximately 80 isolates constructed for each target species contain reference ATCC strains as well as a variety of clinical isolates obtained from various sources. Ubiquitous probes were those hybridizing to at least 80% of DNAs from the battery of clinical isolates of the target species. Examples of specific and ubiquitous oligonucleotide probes are listed in Annex I.

Example 5

Same as example 4 except that a pool of specific oligonucleotide probes is used for bacterial identification (i) to increase sensitivity and assure 100% ubiquity or (ii) to identify simultaneously more than one bacterial species. Bacterial identification could be done from isolated colonies or directly from clinical specimens Example 6

PCR amplification. The technique of PCR was used to increase sensitivity and rapidity of the tests. The PCR primers used were often shorter derivatives of the extensive sets of oligonucleotides previously developed for hybridization assays (Table 6). The sets of primers were tested in PCR assays performed directly from a bacterial colony or from a bacterial suspension (see Example 7) to determine their specificity and ubiquity (Table 7). Examples of specific and ubiquitous PCR primer pairs are listed in annex II.

Specificity and ubiquity tests for amplification primers. The specificity of all selected PCR primer pairs was tested against the battery of Gram negative and Gram positive bacteria used to test the oligonucleotide probes (Table 5). Primer pairs found specific for each species were then tested for their ubiquity to ensure that each set of primers could amplify at least 80% of DNAs from a battery of approximately 80 isolates of the target species. The batteries of isolates constructed for each species contain reference ATCC strains and various clinical isolates representative of the clinical diversity for each species.

Standard precautions to avoid false positive PCR results should be taken. Methods to inactivate PCR amplification products such as the inactivation by uracil-N-glycosylase may be used to control PCR carryover.

Example 7

Amplification directly from a bacterial colony or suspension. PCR assays were performed either directly from a bacterial colony or from a bacterial suspension, the latter being adjusted to a standard McFarland 0.5 (corresponds to $1.5 \times 10^8$ bacteria/mL). In the case of direct amplification from a colony, a portion of the colony was transferred directly to a 50 μL PCR reaction mixture (containing 50 mM KCl, 10 mM Tris pH 8.3, 2.5 mM $MgCl_2$, 0.4 μ.M of each of the two primers, 200 μM of each of the four dNTPs and 1.25 Unit of Taq DNA polymerase (Perkin Elmer)) using a plastic rod. For the bacterial suspension, 4 μL of the cell suspension was added to 46 μL of the same PCR reaction mixture. For both strategies, the reaction mixture was overlaid with 50 μL of mineral oil and PCR amplifications were carried out using an initial denaturation step of 3 min. at 95° C. followed by 30 cycles consisting of a 1 second denaturation step at 95° C. and of a 1 second annealing step at 55° C. in a Perkin Elmer 480™ thermal cycler. PCR amplification products were then analyzed by standard agarose gel (2%) electrophoresis. Amplification products were visualized in agarose gels containing 2.5 μg/mL of ethidium bromide under UV at 254 nm. The entire PCR assay can be completed in approximately one hour.

Alternatively, amplification from bacterial cultures was performed as described above but using a "hot start" protocol. In that case, an initial reaction mixture containing the target DNA, primers and dNTPs was heated at 85° C. prior to the addition of the other components of the PCR reaction mixture. The final concentration of all reagents was as described above. Subsequently, the PCR reactions were submitted to thermal cycling and analysis as described above.

Example 8

Amplification directly from clinical specimens. For amplification from urine specimens, 4.mu.L of undiluted or diluted (1:10) urine was added directly to 46 μL of the above PCR reaction mixture and amplified as described earlier.

To improve bacterial cell lysis and eliminate the PCR inhibitory effects of clinical specimens, samples were routinely diluted in lysis buffer containing detergent(s). Subsequently, the lysate was added directly to the PCR reaction mixture. Heat treatments of the lysates, prior to DNA amplification, using the thermocycler or a microwave oven could also be performed to increase the efficiency of cell lysis.

Our strategy is to develop rapid and simple protocols to eliminate PCR inhibitory effects of clinical specimens and lyse bacterial cells to perform DNA amplification directly from a variety of biological samples. PCR has the advantage of being compatible with crude DNA preparations. For example, blood, cerebrospinal fluid and sera may be used directly in PCR assays after a brief heat treatment. We intend to use such rapid and simple strategies to develop fast protocols for DNA amplification from a variety of clinical specimens.

Example 9

Detection of antibiotic resistance genes. The presence of specific antibiotic resistance genes which are frequently encountered and clinically relevant is identified using the PCR amplification or hybridization protocols described in previous sections. Specific oligonucleotides used as a basis for the DNA-based tests are selected from the antibiotic resistance gene sequences. These tests can be performed either directly from clinical specimens or from a bacterial colony and should complement diagnostic tests for specific bacterial identification.

Example 10

Same as examples 7 and 8 except that assays were performed by multiplex PCR (i.e. using several pairs of primers in a single PCR reaction) to (i) reach an ubiquity of 100% for the specific target pathogen or (ii) to detect simultaneously several species of bacterial pathogens.

For example, the detection of *Escherichia coli* requires three pairs of PCR primers to assure a ubiquity of 100%. Therefore, a multiplex PCR assay (using the "hot-start" protocol (Example 7)) with those three primer pairs was developed. This strategy was also used for the other bacterial pathogens for which more than one primer pair was required to reach a ubiquity of 100%.

Multiplex PCR assays could also be used to (i) detect simultaneously several bacterial species or, alternatively, (ii) to simultaneously identify the bacterial pathogen and detect specific antibiotic resistance genes either directly from a clinical specimen or from a bacterial colony.

For these applications, amplicon detection methods should be adapted to differentiate the various amplicons produced. Standard agarose gel electrophoresis could be used because it discriminates the amplicons based on their sizes. Another useful strategy for this purpose would be detection using a variety of fluorochromes emitting at different wavelengths which are each coupled with a specific oligonucleotide linked to a fluorescence quencher which is degraded during amplification to release the fluorochrome (e.g. TaqMan™, Perkin Elmer).

Example 11

Detection of amplification Products. The person skilled in the art will appreciate that alternatives other than standard agarose gel electrophoresis (Example 7) may be used for the revelation of amplification products. Such methods may be based on the detection of fluorescence after amplification (e.g. Amplisensor™, Biotronics; TaqMan™) or other labels such as biotin (SHARP Signal™ system, Digene Diagnostics). These methods are quantitative and easily automated. One of the amplification primers or an internal oligonucleotide probe specific to the amplicon(s) derived from the species-specific fragment probes is coupled with the fluorochrome or with any other label. Methods based on the detection of fluorescence are particularly suitable for diagnostic tests since they are rapid and flexible as fluorochromes emitting different wavelengths are available (Perkin Elmer).

Example 12

Species-specific, universal and antibiotic resistance gene amplification primers can be used in other rapid amplification procedures such as the ligase chain reaction (LCR), transcription-based amplification systems (TAS), self-sustained sequence replication (3SR), nucleic acid sequence-based amplification (NASBA), strand displacement amplification (SDA) and branched DNA (bDNA) or any other methods to increase the sensitivity of the test. Amplifications can be performed from an isolated bacterial colony or directly from clinical specimens. The scope of this invention is therefore not limited to the use of PCR but rather includes the use of any procedures to specifically identify bacterial DNA and which may be used to increase rapidity and sensitivity of the tests.

Example 13

A test kit would contain sets of probes specific for each bacterium as well as a set of universal probes. The kit is provided in the form of test components, consisting of the set of universal probes labeled with non-radioactive labels as well as labeled specific probes for the detection of each bacterium of interest in specific clinical samples. The kit will also include test reagents necessary to perform the pre-hybridization, hybridization, washing steps and hybrid detection. Finally, test components for the detection of known antibiotic resistance genes (or derivatives therefrom) will be included.

Of course, the kit will include standard samples to be used as negative and positive controls for each hybridization test.

Components to be included in the kits will be adapted to each specimen type and to detect pathogens commonly encountered in that type of specimen. Reagents for the universal detection of bacteria will also be included. Based on the sites of infection, the following kits for the specific detection of pathogens may be developed:

A kit for the universal detection of bacterial pathogens from most clinical specimens which contains sets of probes specific for highly conserved regions of the bacterial genomes.

A kit for the detection of bacterial pathogens retrieved from urine samples, which contains eight specific test components (sets of probes for the detection of *Escherichia coli, Enterococcus faecalis, Klebsiella pneumoniae, Proteus mirabilis, Pseudomonas aeruginosa, Staphylococcus saprophyticus, Staphylococcus aureus* and *Staphylococcus epidermidis*).

A kit for the detection of respiratory pathogens which contains seven specific test components (sets of probes for detecting *Streptococcus pneumoniae, Moraxella catarrhalis, Haemophilus influenzae, Klebsiella pneumoniae, Pseudomonas aeruginosa, Streptococcus pyogenes* and *Staphylococcus aureus*).

A kit for the detection of pathogens retrieved from blood samples, which contains eleven specific test components (sets of probes for the detection of *Streptococcus pneumoniae, Moraxella catarrhalis, Haemophilus influenzae, Proteus mirabilis, Klebsiella pneumoniae, Pseudomonas aeruginosa, Escherichia coli, Enterococcus faecalis, Staphylococcus aureus, Streptococcus pyogenes* and *Staphylococcus epidermidis*).

A kit for the detection of pathogens causing meningitis, which contains four specific test components (sets of probes for the detection of *Haemophilus influenzae, Streptococcus pneumoniae, Escherichia coli* and *Pseudomonas aeruginosa*).

A kit for the detection of clinically important antibiotic resistance genes which contains sets of probes for the specific detection of at least one of the 19 following genes associated with bacterial resistance: $bla_{tem}$, $bla_{rob}$, $bla_{shv}$, aadB, aacC1, aacC2, aacC3, aacA4, mecA, vanA, vanH, vanX, satA, aacA-aphD, vat, vga, msrA, sul and int.

Other kits adapted for the detection of pathogens from skin, abdominal wound or any other clinically relevant kits will be developed.

Example 14

Same as example 13 except that the test kits contain all reagents and controls to perform DNA amplification assays. Diagnostic kits will be adapted for amplification by PCR (or other amplification methods) performed directly either from clinical specimens or from a bacterial colony. Components required for universal bacterial detection, bacterial identification and antibiotic resistance genes detection will be included.

Amplification assays could be performed either in tubes or in microtitration plates having multiple wells. For assays in plates, the wells will be coated with the specific amplification primers and control DNAs and the detection of amplification products will be automated. Reagents and amplification primers for universal bacterial detection will be included in kits for tests performed directly from clinical specimens. Components required for bacterial identification and antibiotic resistance gene detection will be included in kits for testing directly from colonies as well as in kits for testing directly from clinical specimens.

The kits will be adapted for use with each type of specimen as described in example 13 for hybridization-based diagnostic kits.

Example 15

It is understood that the use of the probes and amplification primers described in this invention for bacterial detection and identification is not limited to clinical microbiology applications. In fact, we feel that other sectors could also benefit from these new technologies. For example, these tests could be used by industries for quality control of food, water, pharmaceutical products or other products requiring microbiological control. These tests could also be applied to detect and identify bacteria in biological samples from organisms other than humans (e.g. other primates, mammals, farm animals and live stocks). These diagnostic tools could also be very useful for research purposes including clinical trials and epidemiological studies.

TABLE 1

Distribution of urinary isolates from positive urine samples ($\geq 10^7$CFU/L) at the Centre Hospitalier de l'Université Laval (CHUL) for the 1992-1994 period

| | % of isolates | | | |
| --- | --- | --- | --- | --- |
| Organisms | November 1992 n = 267[a] | April 1993 n = 265 | July 1993 n = 238 | January 1994 n = 281 |
| *Escherichia coli* | 53.2 | 51.7 | 53.8 | 54.1 |
| *Enterococcus faecalis* | 13.8 | 12.4 | 11.7 | 11.4 |
| *Klebsiella pneumoniae* | 6.4 | 6.4 | 5.5 | 5.3 |
| *Staphylococcus epidermidis* | 7.1 | 7.9 | 3.0 | 6.4 |
| *Proteus mirabilis* | 2.6 | 3.4 | 3.8 | 2.5 |
| *Pseudomonas aeruginosa* | 3.7 | 3.0 | 5.0 | 2.9 |
| *Staphylococcus saprophyticus* | 3.0 | 1.9 | 5.4 | 1.4 |
| Others[b] | 10.2 | 13.3 | 11.8 | 16.0 |

[a] n = total number of isolates for the indicated month
[b] See Table 2

TABLE 2

Distribution of uncommon[a] urinary isolates from positive urine samples ($\geq 10^7$CFU/L) at the Centre Hospitalier de l'Université Laval (CHUL) for the 1992-1994 period

| | % of isolates | | | |
| --- | --- | --- | --- | --- |
| Organisms | November 1992 | April 1993 | July 1993 | January 1994 |
| *Staphylococcus aureus* | 0.4 | 1.1 | 1.3 | 1.4 |
| *Staphylococcus* spp. | 2.2 | 4.9 | 1.7 | 6.0 |
| *Micrococcus* spp. | 0.0 | 0.0 | 0.4 | 0.7 |
| *Enterococcus faecium* | 0.4 | 0.4 | 1.3 | 1.4 |
| *Citrobacter* spp. | 1.4 | 0.8 | 0.4 | 0.7 |
| *Enterobacter* spp. | 1.5 | 1.1 | 1.3 | 1.4 |
| *Klebsiella oxytoca* | 1.1 | 1.5 | 2.5 | 1.8 |
| *Serratia* spp. | 0.8 | 0.0 | 0.5 | 0.0 |
| *Proteus* spp. | 0.4 | 0.4 | 0.0 | 1.1 |
| *Moganella* and *Providencia* | 0.4 | 0.8 | 0.4 | 0.0 |

TABLE 2-continued

Distribution of uncommon[a] urinary isolates from positive urine samples
(≧10⁷CFU/L) at the Centre Hospitalier de l'Université Laval
(CHUL) for the 1992-1994 period

| | % of isolates | | | |
|---|---|---|---|---|
| Organisms | November 1992 | April 1993 | July 1993 | January 1994 |
| Hafania alvei | 0.8 | 0.0 | 0.0 | 0.0 |
| NFB[b] (Stenotrophomonas, Acinetobacter | 0.0 | 0.4 | 1.3 | 1.1 |
| Candida spp. | 0.8 | 1.9 | 0.7 | 0.4 |

[a]Uncommon urinary isolates are those identified as "Others" in Table 1.
[b]NFB: non-fermentative bacilli

TABLE 3

Distribution of positive[a] (bacterial count ≧10⁷CFU/L) and negative
samples (bacterial count ≦10⁷CFU/L) urine specimens tested at the
Centre Hospitalier de l'Université Laval (CHUL) for the
1992-1994 period

| | Number of isolates | | | |
|---|---|---|---|---|
| | November 1992 n = 267[a] | April 1993 n = 265 | July 1993 n = 238 | January 1994 n = 281 |
| received | 53.2 | 51.7 | 53.8 | 54.1 |
| positive | 13.8 | 12.4 | 11.7 | 11.4 |
| negative | 6.4 | 6.4 | 5.5 | 5.3 |

[a]n = total number of isolates for the indicated month

TABLE 4

Distribution of positive and negative clinical specimens
tested in the Microbiology Laboratory of the CHUL

| Clinical Specimens[a] | No. of samples tested | % of positive specimens | % of negative specimens |
|---|---|---|---|
| Urine | 17,981 | 19.4 | 80.6 |
| Haemocluture/marrow | 10.010 | 6.9 | 93.1 |
| Sputum | 1,266 | 68.4 | 31.6 |
| Superficial pus | 1,136 | 72.3 | 27.7 |
| Cerebrospinal fluid | 553 | 1.0 | 99.0 |
| Synovial fluid-articular | 523 | 2.7 | 97.3 |
| Bronch./Trach./Amyg/Throat | 502 | 56.6 | 43.4 |
| Deep pus | 473 | 56.8 | 43.2 |
| Ears | 289 | 47.1 | 52.9 |
| Pleural and pericardial fluid | 132 | 1.0 | 99.0 |
| Peritonial fluid | 101 | 28.6 | 71.4 |

[a]Specimens tested from February 1994 to January 1995

TABLE 5

Bacterial Species (66) used for testing the specificity of DNA
fragment probes, oligonucleotides probes and PCR primers

| Bacterial species Gram negative: | Number of strains tested | Bacterial species Gram negative: | Number of strains tested |
|---|---|---|---|
| Proteus mirabilis | 5 | Streptococcus pneumoniae | 7 |
| Klebsiella pneumoniae | 5 | Streptococcus salivarius | 2 |
| Pseudomonas aeruginosa | 5 | Streptococcus viridans | 2 |
| Escherichia coli | 5 | Streptococcus pyogenes | 2 |
| Moraxella catarrhalis | 5 | Staphylococcus aureus | 2 |
| Proteus vulgaris | 2 | Staphylococcus epidermidis | 2 |
| Morganella morganii | 2 | | |

TABLE 5-continued

Bacterial Species (66) used for testing the specificity of DNA
fragment probes, oligonucleotides probes and PCR primers

| Bacterial species Gram negative: | Number of strains tested | Bacterial species Gram negative: | Number of strains tested |
|---|---|---|---|
| Enterobater cloacae | 2 | Staphylococcus saprophyticus | 5 |
| Providencia stuartii | 1 | | |
| Providencia spp. | 1 | Micrococcus species | 2 |
| Enterobacter agglomerans | 2 | Corynebacterium species | 2 |
| Providencia rettgeri | 2 | Streptococcus group B | 2 |
| Neisseria mucosa | 1 | | |
| Providencia alcalifaciens | 1 | Staphylococcus simulans | 2 |
| Providencia rustigianii | 1 | Staphylococcus ludgunesis | 1 |
| | | Staphylococcus capitis | 2 |
| Burkholderia cepacia | 2 | Staphylococcus haemolyticus | 2 |
| Enterobacter aerogenes | 2 | | |
| Stenotrophomonas maltophilia | 2 | Staphylococcus hominis | 2 |
| | | Enterococcus faecalis | 2 |
| Pseudomonas fluorescens | 1 | Enterococcus faecium | 1 |
| | | Staphylococcus warneri | 1 |
| Comamonas acidovorans | 2 | Enterococcus durans | 1 |
| Pseudomonas putida | 2 | Streptococcus bovis | 1 |
| Haemophilus influenzae | 5 | Diphteriods | 2 |
| Haemophilus parainfluenzae | 2 | Lactobacillus acidophilus | 1 |
| Bordetella pertussis | 2 | | |
| Haemophilus parahaemolyticus | 2 | | |
| Haemophilus aegyptius | 2 | | |
| Kingella indologenes | 1 | | |
| Moraxella atlantae | 1 | | |
| Neisseria cavaie | 1 | | |
| Neisseria subflava | 1 | | |
| Moraxella urethralis | 1 | | |
| Shigella sonnei | 1 | | |
| Shigella flexneri | 1 | | |
| Klebsiella oxytoca | 2 | | |
| Serratia marcescens | 2 | | |
| Salmonella typhimurium | 1 | | |
| Yersinia enterocolitica | 1 | | |
| Acinetobacter calcoaceticus | 1 | | |
| Acinetobacter lwoffi | 1 | | |
| Hafnia alvei | 2 | | |
| Citrobacter diversus | 1 | | |
| Citrobacter freundii | 1 | | |
| Salmonella species | 1 | | |

TABLE 6

Species-specific DNA fragment and oligonucleotide
probes for hybridization

| | Number of fragment probes | | | Number of oligonucleotide probes | | |
|---|---|---|---|---|---|---|
| Organisms | Tested | Specific | Ubiquitous | Synthesized | Specific | Ubiquitous |
| E. coli[d] | — | — | — | 20 | 12 | 9[f] |
| E. coli | 14 | 2 | 2[e] | — | — | — |
| K. pneumoniae[d] | — | — | — | 15 | 1 | 1 |
| K. pneumoniae | 33 | 3 | 3 | 18 | 12 | 8 |
| P. mirabilis[d] | — | — | — | 3 | 3 | 2 |
| P. mirabilis | 14 | 3 | 3[e] | 15 | 8 | 7 |
| P. aeruginosa[d] | — | — | — | 26 | 13 | 9 |

TABLE 6-continued

Species-specific DNA fragment and oligonucleotide probes for hybridization

| Organisms | Number of fragment probes | | | Number of oligonucleotide probes | | |
|---|---|---|---|---|---|---|
| | Tested | Specific | Ubiquitous | Synthesized | Specific | Ubiquitous |
| P. aeruginosa | 6 | 2 | 2[e] | 6 | 0 | 0 |
| S. saprophyticus | 7 | 4 | 4 | 20 | 9 | 7 |
| H. influenzae[d] | — | — | — | 16 | 2 | 2 |
| H. influenzae | 1 | 1 | 1 | 20 | 1 | 1 |
| S. pneumoniae[d] | — | — | — | 6 | 1 | 1 |
| M. catarrhalis | 2 | 2 | 2 | 9 | 8 | 8 |
| S. epidermidis | 62 | 1 | 1 | — | — | — |
| S. aureus | 30 | 1 | 1 | — | — | — |
| Universal probes[d] | — | — | — | 7 | — | 7g |

[a]No DNA fragment or oligonucleotide probes were tested for E. faecalis and S. pyogenes.
[b]Sizes of DNA fragments range from 0.25 to 5.0 kbp
[c]A specific probe was considered ubiquitous when at least 80% of isolates of the target species (approximately 80 isolates) were recognized by each specific probe. When 2 or more probes are combined, 100% of the isolates are recognized.
[d]These sequences were selected from data banks.
[e]Ubiquity tested with approximately 10 isolates of the target species
[f]A majority of probes (8/9) do not discriminate E. coli and Shigella spp.
gUbiquity testes with a pool of the 7 probes detected all 66 bacterial species listed in Table 5.

TABLE 7

PCR amplification for bacterial pathogens commonly encountered in urine, sputum, blood, cerebrospinal fluid and other specimens

| Organism | Primer pair #(SEQ ID NO:) | Amplicon size (bp) | Ubiquity[b] | DNA amplification from colonies[c] | from specimens[d] |
|---|---|---|---|---|---|
| E. coli | 1[e] (55-56) | 107 | 75/80 | + | + |
| | 2[e] (46-47) | 297 | 77/80 | + | + |
| | 3 (42-43) | 102 | 78/80 | + | + |
| | 4 (131-132) | 134 | 73/80 | + | + |
| | 1 + 2 + 3 + 4 | — | 80/80 | + | + |
| E. faecalis | 1[e] (38-39) | 200 | 71/80 | + | + |
| | 2[e] (40-41) | 121 | 79/80 | + | + |
| | 1 + 2 | — | 80/80 | + | + |
| K. pneumoniae | 1 (67-68) | 198 | 76/80 | + | + |
| | 2 (61-62) | 143 | 67/80 | + | + |
| | 3[h] (135-136) | 148 | 78/80 | + | N.T.[i] |
| | 4 (137-138) | 116 | 69/80 | + | N.T. |
| | 1 + 2 + 3 | — | 80/80 | + | N.T. |
| P. mirabilis | 1 (74-75) | 167 | 73/80 | + | N.T. |
| | 2 (133-134) | 123 | 8080 | + | N.T. |
| P. aeruginosa | 1[e] (83-84) | 139 | 79/80 | + | N.T. |
| | 2[e] (85-86) | 223 | 80/80 | + | N.T. |
| S. saprophyticus | 1 (98-99) | 126 | 79/80 | + | + |
| | 2 (139-140) | 190 | 80/80 | + | N.T. |
| M. catarrhalis | 1 (112-113) | 157 | 79/80 | + | N.T. |
| | 2 (118-119) | 118 | 80/80 | + | N.T. |
| | 3 (160-119) | 137 | 80/80 | + | N.T. |
| H. influenzae | 1[e] (154-155) | 217 | 80/80 | + | N.T. |
| S. pneumoniae | 1[e] (156-157) | 134 | 80/80 | + | N.T. |
| | 2[e] (158-159) | 197 | 74/80 | + | N.T. |
| | 3 (78-79) | 175 | 67/80 | + | N.T. |
| S. epidermidis | 1 (147-148) | 175 | 80/80 | + | N.T. |
| | 2 (145-146) | 125 | 80/80 | + | N.T. |
| S. aureus | 1 (152-153) | 108 | 80/80 | + | N.T. |
| | 2 (149-150) | 151 | 80/80 | + | N.T. |
| | 3 (149-151) | 176 | 80/80 | + | N.T. |
| S. pyogenes[f] | 1[e] (141-142) | 213 | 80/80 | + | N.T. |
| | 2[e] (143-144) | 157 | 24/24 | + | N.T. |
| Universal | 1[e] (126-127) | 241 | 194/195g | + | N.T. |

[a]All primer pairs are specific in PCR assays since no amplification was observed with DNA from 66 different species of both Gram positive and Gram negative bacteria other than the species of interest.
[b]The ubiquity was normally tested on 80 strains of the species of interest. All retained primer pairs amplified at least 90% of the isolates. When combinations of primers were used, a ubiquity of 100% was reached.
[c]For all primer pairs and multiplex combinations, PCR amplifications directly performed from a bacterial colony were 100% species specific.
[d]PCR assays performed directly from urine specimens.
[e]Primer pairs derived from data bank sequences. Primer pairs with no "e" are derived from our species-specific fragments.
[f]For S. pyogenes, primer pair #1 is specific for Group A Streptococci (GAS). Primer pair #2 is specific for GAS-producing exotoxin A gene (SpeA)
gUbiquity tested on 195 isolates from 23 species representative of bacterial pathogens commonly encountered in clinical specimens.
[h]Optimizations are in progress to eliminate non-specific amplification observed with some bacterial species other than the target species.
[i]N.T.: not tested.

TABLE 8

Selected antibiotic resistance genes for diagnostic purposes

| Genes | Antibiotics | Bacteria[a] | SEQ ID NO: |
|---|---|---|---|
| (bla$_{tem}$) TEM-1 | β-lactams | Enterobacteriaceae, Pseudomonadaceae, Haemophilus, Neisseria | 161 |
| (bla$_{rob}$) ROB-1 | β-lactams | Haemophilus, Pasteurella | 162 |
| (bla$_{shv}$) SHV-1 | β-lactams | Klebsiella and other Enterobacteriaceae | 163 |
| aadB, aacC1, aacC2, aacC3, aacC4, aacA4 | Aminoglycosides | Enterobacteriaceae, Pseudomonadaceae | 164, 165, 166, 167, 168 |
| mecA | β-lactams | Staphylococci | 169 |
| vanH, vanA, vanX | Vancomycin | Enterococci | 170 |
| satA | Macrolides | Enterococci | 173 |
| aacA-aphD | Aminoglycosides | Enterococci, Staphylococci | 174 |
| vat | Macrolides | Staphylococci | 175 |
| vga | Macrolides | Staphylococci | 176 |
| msrA | Erythromycin | Staphylococci | 177 |
| Int and Sul | β-lactams, trimethoprim | Enterobacteriaceae | 171, 172 |
| conserved sequences | aminoglycosides, antiseptic, chloramphenicol | Pseudomonadaecae | |

[a]Bacteria having high incidence for the specified antibiotic resistance genes. The presence in other bacteria is not excluded.

ANNEX I

Annex I: Specific and ubiquitous oligonucleotide probes for hybridization

| SEQ ID NO: | Nucleotide Sequence | Originating DNA fragment SEQ ID NO: | Nucleotide position |
|---|---|---|---|

Bacterial species: Escherichia coli

| SEQ ID NO: | Nucleotide Sequence | Originating SEQ ID NO: | Nucleotide position |
|---|---|---|---|
| 44 | 5'-CAC CCG CTT GCG TGG CAA GCT GCC C | 5[a] | 213-237 |
| 45 | 5'-CGT TTG TGG ATT CCA GTT CCA TCC G | 5[a] | 489-513 |
| 48 | 5'-TGA AGC ACT GGC CGA AAT GCT GCG T | 6[a] | 759-783 |
| 49 | 5'-GAT GTA CAG GAT TCG TTG AAG GCT T | 6[a] | 898-922 |
| 50 | 5'-TAG CGA AGG CGT AGC AGA AAC TAA C | 7[a] | 1264-1288 |
| 51 | 5'-GCA ACC CGA ACT CAA CGC CGG ATT T | 7[a] | 1227-1251 |
| 52 | 5'-ATA CAC AAG GGT CGC ATC TGC GGC C | 7[a] | 1313-1337 |
| 53 | 5'-TGC GTA TGC ATT GCA GAC CTT GTG GC | 7[a] | 111-136 |
| 54 | 5'-GCT TTC ACT GGA TAT CGC GCT TGG G | 7[a] | 373-397 |

Bacterial species: Proteus mirabilis

| SEQ ID NO: | Nucleotide Sequence | Originating SEQ ID NO: | Nucleotide position |
|---|---|---|---|
| 70[b] | 5'-TGG TTC ACT GAC TTT GCG ATG TTT C | 12 | 23-47 |
| 72 | 5'-TCG AGG ATG GCA TGC ACT AGA AAA T | 12 | 53-77 |
| 72[b] | 5'-CGC TGA TTA GGT TTC GCT AAA ATC TTA TTA | 12 | 80-109 |
| 73 | 5'-TTG ATC CTC ATT TTA TTA ATC ACA TGA CCA | 12 | 174-203 |
| 76 | 5'-CCG CCT TTA GCA TTA ATT GGT GTT TAT AGT | 13 | 246-275 |
| 77 | 5'-CCT ATT GCA GAT ACC TTA AAT GTC TTG GGC | 13 | 291-320 |
| 80[b] | 5'-TTG AGT GAT GAT TTC ACT GAC TCC C | 14 | 18-42 |
| 81 | 5'-GTG AGA CAG TGA TGG TGA GGA CAC A | 15[a] | 1185-1203 |
| 82 | 5'-TGG TTG TCA TGC TGT TTG TGT GAA AAT | 15[a] | 1224-1230 |

Bacterial species: Klebsiella pneumoniae

| SEQ ID NO: | Nucleotide Sequence | Originating SEQ ID NO: | Nucleotide position |
|---|---|---|---|
| 57 | 5'-GTG GTG TCG TTC AGG GGT TTC AC | 8 | 45-67 |
| 58 | 5'-GCG ATA TTC ACA CCC TAC GCA GCC A | 9 | 161-185 |
| 59[b] | 5'-GTC GAA AAT GCC GGA AGA GGT ATA CG | 9 | 203-228 |
| 60[b] | 5'-ACT GAG CTG CAG ACC GGT AAA ACT CA | 9 | 233-258 |
| 63[b] | 5'-CGT GAT GGA TAT TCT TAA CGA AGG GC | 10 | 250-275 |
| 64[b] | 5'-ACC AAA CTG TTG AGC CGC CTG GA | 10 | 201-223 |
| 65 | 5'-GTG ATC GCC CCT CAT CTG CTA CT | 10 | 77-99 |
| 66 | 5'-CGC CCT TCG TTA AGA ATA TCC ATC AC | 10 | 249-274 |
| 69 | 5'-CAG GAA GAT GCT GCA CCG GTT GTT G | 11[a] | 296-320 |

Bacterial species: Pseudomonas aeruginosa

| SEQ ID NO: | Nucleotide Sequence | Originating SEQ ID NO: | Nucleotide position |
|---|---|---|---|
| 87 | 5'-AAT GCG GCT GTA CCT CGG CGC TGG T | 18[a] | 2985-3009 |
| 88 | 5'-GGC GGA GGG CCA GTT GCA CCT GCC A | 18[a] | 2929-2953 |
| 89 | 5'-AGC CCT GCT CCT CGG CAG CCT CTG C | 18[a] | 2821-2845 |
| 90 | 5'-TGG CTT TTG CAA CCG CGT TCA GGT T | 18[a] | 1079-1103 |
| 91 | 5'-GCG CCC GCG AGG GCA TGC TTC GAT G | 19[a] | 705-729 |
| 92 | 5'-ACC TGG GCG CCA ACT ACA AGT TCT A | 19[a] | 668-692 |

ANNEX I-continued

Annex I: Specific and ubiquitous oligonucleotide probes for hybridization

| SEQ ID NO: | Nucleotide Sequence | Originating DNA fragment SEQ ID NO: | Nucleotide position |
|---|---|---|---|
| 93 | 5'-GGC TAC GCT GCC GGG CTG CAG GCC G | 19[a] | 505-529 |
| 94 | 5'-CCG ATC TAG ACC ATC GAG ATG GGC G | 20[a] | 1211-1235 |
| 95 | 5'-GAG CGC GGC TAT GTG TTC GTC GGC T | 20[a] | 2111-2135 |

Bacterial species: *Streptococcus pneumoniae*

| 120 | 5'-TCT GTG CTA GAG ACT GCC CCA TTT C | 30 | 423-447 |
| 121 | 5'-CGA TGT CTT GAT TGA GCA GGG TTA T | 31[a] | 1198-1222 |

Bacterial species: *Staphylococcus saprophyticus*

| 96 | 5'-CGT TTT TAC CCT TAC CTT TTC GTA CTA CC | 21 | 45-73 |
| 97[b] | 5'-TCA GGC AGA GGT AGT ACG AAA AGG TAA GGG | 21 | 53-82 |
| 100 | 5'-CAC CAA GTT TGA CAC GTG AAG ATT CAT | 22 | 89-115 |
| 101[b] | 5'-ATG AGT GAA GCG GAG TCA GAT TAT GTG CAG | 23 | 105-134 |
| 102 | 5'-CGC TCA TTA CGT ACA GTG ACA ATC G | 24 | 20-44 |
| 103 | 5'-CTG GTT AGC TTG ACT CTT AAC AAT CTT GTC | 24 | 61-90 |
| 104[b] | 5'-GAC GCG ATT GTC ACT GTA CGT AAT GAG CGA | 24 | 19-48 |

Bacterial species: *Moraxella catarrhalis*

| 108 | 5'-GCC CCA AAA CAA TGA AAC ATA TGG T | 28 | 81-105 |
| 109 | 5'-CTG CAG ATT TTG GAA TCA TAT CGC C | 28 | 126-130 |
| 110 | 5'-TGG TTT GAC CAG TAT TTA ACG CCA T | 28 | 165-189 |
| 111 | 5'-CAA CGG CAC CTG ATG TAC CTT GTA C | 28 | 232-256 |
| 114 | 5'-TTA CAA CCT GCA CCA CAA GTC ATC A | 29 | 97-121 |
| 115 | 5'-GTA CAA ACA AGC CGT CAG CGA CTT A | 29 | 139-163 |
| 116 | 5'-CAA TCT GCG TGT GTG CGT TCA CT | 29 | 178-200 |
| 117 | 5'-GCT ACT TTG TCA GCT TTA GCC ATT CA | 29 | 287-312 |

Bacterial species: *Haemophilus influenzae*

| 105[b] | 5'-GCG TCA GAA AAA GTA GGC GAA ATG AAA G | 25 | 138-165 |
| 106[b] | 5'-AGC GGC TCT ATC TTG TAA TGA CAC A | 26[a] | 770-794 |
| 107[b] | 5'-GAA ACG TGA ACT CCC CTC TAT ATA A | 27[a] | 5184-5208 |

Universal probes[c]

| 122[b] | 5'-ATC CCA CCT TAG GCG GCT GGC TCC A | — | — |
| 123 | 5'-ACG TCA AGT CAT CAT GGC CCT TAC GAG TAG G | — | — |
| 124[b] | 5'-GTG TGA CGG GCG GTG TGT ACA AGG C | — | — |
| 125[b] | 5'-GAG TTG CAG ACT CCA ATC CGG ACT ACG A | — | — |
| 128[b] | 5'-CCC TAT ACA TCA CCT TGC GGT TTA GCA GAG AG | — | — |
| 129 | 5'-GGG GGG ACC ATC CTC CA GGC TAA ATA C | — | — |
| 130[b] | 5'-CGT CCA CTT TCG TGT TTG CAG AGT GCT GTG TT | — | — |

[a] Sequence from data banks
[b] These sequences are from the opposite DNA strand of the sequences given in the Sequence listing.

ANNEX II

ANNEX II: Specific and ubiquitous primers for DNA amplification

| SEQ ID NO: | Nucleotide Sequence | Originating DNA fragment SEQ ID NO: | Nucleotide position |
|---|---|---|---|

Bacterial species: *Escherichia coli*

| 42 | 5'-GCT TTC CAG CGT CAT ATT G | 4 | 177-195 |
| 43[b] | 5'-GAT CTC GAC AAA ATG GTG A | 4 | 260-278 |
| 46 | 5'-TCA CCC GCT TGC GTG GC | 5[a] | 212-228 |
| 47[b] | 5'-GGA ACT GGA ATC CAC AAA C | 5[a] | 490-508 |
| 55 | 5'-GCA ACC CGA ACT CAA CGC C | 7[a] | 1227-1245 |
| 56[b] | 5'-GCA GAT GCG ACC CTT GTG T | 7[a] | 1315-1333 |

ANNEX II-continued

ANNEX II: Specific and ubiquitous primers for DNA amplification

| SEQ ID NO: | Nucleotide Sequence | Originating DNA fragment SEQ ID NO: | Nucleotide position |
|---|---|---|---|
| 131 | 5'-CAG GAG TAC GGT GAT TTT TA | 3 | 60-79 |
| 132[b] | 5'-ATT TCT GGT TTG GTC ATA CA | 3 | 174-193 |

Bacterial species: *Enterococcus faecalis*

| 38 | 5'-GCA ATA CAG GGA AAA ATG TC | 1[a] | 69-88 |
| 39[b] | 5'-CTT CAT CAA ACA ATT AAC TC | 1[a] | 249-268 |
| 40 | 5'-GAA CAG AAG AAG CCA AAA AA | 2[a] | 569-588 |
| 41[b] | 5'-GCA ATC CCA AAT AAT ACG GT | 2[a] | 670-689 |

Bacterial species: *Kiebsiella pneumoniae*

| 61 | 5'-GAC AGT CAG TTC GTC AGC C | 9 | 37-55 |
| 62[b] | 5'-CGT AGG GTG TGA ATA TCG C | 9 | 161-179 |
| 67 | 5'-TCG CCC CTC ATC TGC TAC T | 10 | 81-99 |
| 68[b] | 5'-GAT CGT GAT GGA TAT TCT T | 10 | 260-278 |
| 135 | 5'-GCA GCG TGG TGT CGT TCA | 8 | 40-57 |
| 136[b] | 5'-AGC TGG CAA CGG CTG GTC | 8 | 170-187 |
| 137 | 5'-ATT CAC ACC CTA CGC AGC CA | 9 | 166-185 |
| 138[b] | 5'-ATC CGG CAG CAT CTC TTT GT | 9 | 262-281 |

Bacterial species: *Proteus mirabilis*

| 74 | 5'-GAA ACA TCG CAA AGT CAG T | 12 | 23-41 |
| 75[b] | 5'-ATA AAA TGA GGA TCA AGT TC | 12 | 170-189 |
| 133 | 5'-CGG GAG TCA GTG AAA TCA TC | 14 | 17-36 |
| 134[b] | 5'-CTA AAA TCG CCA CAC CTC TT | 14 | 120-139 |

Bacterial species: *Staphylococcus saprophyticus*

| 98 | 5'-CGT TTT TAC CCT TAC CTT TTC GTA CT | 21 | 45-70 |
| 99[b] | 5'-ATC GAT CAT CAC ATT CCA TTT GTT TTT A | 21 | 143-170 |
| 139 | 5'-CTG GTT AGC TTG ACT CTT AAC AAT C | 24 | 61-85 |
| 140[b] | 5'-TCT TAA CGA TAG AAT GGA GCA ACT G | 24 | 26-250 |

Bacterial species: *Psuedomonas aeruginosa*

| 83 | 5'-CGA GCG GGT GGT GTT CAT C | 16[a] | 554-572 |
| 84[b] | 5'-CAA GTC GTG GTG GGA GGG A | 16[a] | 674-692 |
| 85 | 5'-TCG CTG TTC ATC AAG ACC C | 17[a] | 1423-1441 |
| 86[b] | 5'-CCG AGA ACC AGA CTT CAT C | 17[a] | 1627-1645 |

Bacterial species: *Moraxella catarrhalis*

| 112 | 5'-GGC ACC TGA TGT ACC TTG | 28 | 235-252 |
| 113[b] | 5'-AAC AGC TCA CAC GCA TT | 28 | 375-391 |
| 118 | 5'-TGT TTT GAG CTT TTT ATT TTT TGA | 29 | 41-64 |
| 119[g] | 5'-CGC TGA CGG CTT GTT TGT ACC A | 29 | 137-158 |
| 160 | 5'-GCT CAA ATC AGG GTC AGC | 29 | 22-39 |
| 119[b] | 5'-CGC TGA CGG CTT GTT TGT ACG A | 29 | 137-158 |

Bacterial species: *Staphylococcus epidermidis*

| 145 | 5'-ATC AAA AAG TTG GCG AAC CTT TTC A | 36 | 21-45 |
| 146[b] | 5'-CAA AAG AGC GTG GAG AAA AGT ATC A | 36 | 121-145 |
| 147 | 5'-TCT CTT TTA ATT TCA TCT TCA ATT CCA TAG | 36 | 448-477 |
| 148[b] | 5'-AAA CAC AAT TAC AGT CTG GTT ATC CAT ATC | 36 | 593-622 |

Bacterial species: *Staphylococcus aureus*

| 149[b] | 5'-CTT CAT TTT ACG GTG ACT TCT TAG AAG ATT | 37 | 409-438 |
| 150 | 5'-TCA ACT GTA GCT TCT TTA TCC ATA CGT TGA | 37 | 288-317 |
| 149[b] | 5'-CTT CAT TTT ACG GTG ACT TCT TAG AAG ATT | 37 | 409-438 |
| 151 | 5'-ATA TTT TAG CTT TTC AGT TTC TAT ATC AAC | 37 | 263-292 |
| 152 | 5'-AAT CTT TGT CGG TAC ACG ATA TTC TTC ACG | 37 | 5-34 |
| 153[b] | 5'-CGT AAT GAG ATT TCA GTA GAT AAT ACA ACA | 37 | 83-112 |

Bacterial species: *Haemophilus influenzae*

| 154 | 5'-TTT AAC GAT CCT TTT ACT CCT TTT G | 27[a] | 5074-5098 |
| 155[b] | 5'-ACT GCT GTT GTA AAG AGG TTA AAA T | 27[a] | 5266-5290 |

ANNEX II-continued

ANNEX II: Specific and ubiquitous primers for DNA amplification

| SEQ ID NO: | Nucleotide Sequence | Originating DNA fragment SEQ ID NO: | Nucleotide position |
|---|---|---|---|
| Bacterial species: *Streptococcus pneumoniae* | | | |
| 78 | 5'-AGT AAA ATG AAA TAA GAA CAG GAC AG | 34 | 164-189 |
| 79[b] | 5'-AAA ACA GGA TAG GAG AAC GGG AAA A | 34 | 314-338 |
| 156 | 5'-ATT TGG TGA CGG GTG ACT TT | 31[a] | 1401-1420 |
| 157[b] | 5'-GCT GAG GAT TTG TTC TTC TT | 31[a] | 1515-1534 |
| 158 | 5'-GAG CGG TTT CTA TGA TTG TA | 35[a] | 1342-1361 |
| 159[b] | 5'-ATC TTT CCT TTC TTG TTC TT | 35[a] | 1519-1538 |
| Bacterial species: *Steptococcus pyogenes* | | | |
| 149 | 5'-TGA AAA TTC TTG TAA CAG GC | 32[a] | 286-305 |
| 142[b] | 5'-GGC CAC CAG CTT GCC CAA TA | 32[a] | 479-498 |
| 143 | 5'-ATA TTT TCT TTA TGA GGG TG | 33[a] | 966-985 |
| 144[b] | 5'-ATC CTT AAA TAA AGT TGC CA | 33[a] | 1103-1122 |
| Universal primers[c] | | | |
| 126 | 5'-GGA GGA AGG TGG GGA TGA CG | — | — |
| 127[b] | 5'-ATG GTG TGA CGG GCG GTG TG | — | — |

[a] Sequence from data banks
[b] These sequences are from the opposite DNA strand of the sequences given in the Sequence listing.

ANNEX III

ANNEX III
Selection of Universal Probes by Alignment of the Sequences of Bacterial
16S and 23S Ribosomal RNA Genes

```
Reverse strand of              TGGACGG AGCCGCCTA GGTGGGAT
SEQ ID NO: 122
                        1251                                                    1300
Streptococcus salivarius TGAGGTAACC TTTTGGAGCC AGCCGCCTAA GGTGGGATAG ATGANNGGGG
Proteus vulgaris         TAGCTTAACC TTCGGGAGGG CGCTTACCAC TTTGTGATTC ATGACTGGGG
Pseudomonas aeruginosa   TAGTCTAACC GCAAGGGGGA CGGTTACCAC GGAGTGATTC ATGACTGGGG
Neiserria gonorrhoeae    TAGGGTAACC GCAAGGAGTC CGCTTACCAC GGTATGCTTC ATGACTGGGG
Streptococcus lactis     TTGCCTAACC GCAAGGAGGG CGCTTCCTAA GGTAAGACCG ATGACNNGGG SEQ ID NO: 123                       ACGTCAAGTC ATCATGGC CCTTACGAGT AGG
                        1251                                                    1300
Haemophilus influenzae   GGTNGGGATG ACGTCAAGTC ..ATCATGGC CCTTACGAGT AGGGCTACAC
Neiserria gonorrhoeae    GGTGGGGATG ACGTCAAGTC ..CTCATGGC CCTTATGACC AGGGCTTCAC
Pseudomonas cepacia      GGTNGGGATG ACGTCAAGTC ..CTCATGGC CCTTATGGGT AGGGCTTCAC
Serratia marcescens      GGTGGGGATG ACGTCAAGTC ..CTCATGGC CCTTATGGGT AGGGCTTCAC
Escherichia coli         GGTGGGGATG ACGTCAAGTC ..ATCATGGC CCTTACGACC AGGGCTACAC
Proteus vulgaris         GGTGGGGATG ACGTTAAGTC GTATCATGGC CCTTACGAGT AGGGCTACAC
Pseudomonas aeruginosa   GGTGGGGATG ACGTCAAGTC ..ATCATGGC CCTTACGGCN AGGGCTACAC
Clostridium pefringens   GGTGGGGATG ACGTNNAATC ..ATCATGCC CNTTATGTGT AGGGCTACAC
Mycoplasma hominis       GGTGGGGATG ACGTCAAATC ..ATCATGCC TCTTACGAGT GGGGCCACAC
Helicobacter pylori      GGTGGGGACG ACGTCAAGTC ..ATCATGGC CCTTACGCCT AGGGCTACAC
Mycoplasma pneumoniae    GGAAGGGATG ACGTCAAATC ..ATCATGCC CCTTATGTCT AGGGCTGCAA Reverse of the probe                GCCTTGTACA CACCGCCCGT CACAC
SEQ ID NO: 124
                        1451                                                    1490
Escherichia coli         ACGTTCCCGG GCCTTGTACA CACCGCCCGT CACACCATGG
Neiserria ghonorrhoeae   ACGTTCCCNG NNCTTGTACA CACCGCCCGT CACACCATGG
Pseudomonas cepacia      ACGTTCCCGG GTCTTGTACA CACNGCCCGT CACACCATGG
Serratia marcescens      ACGTTCCCGG GCCTTGTACA CACCGCCCGT CACACCATGG
Proteus vulgaris         ACGTTCCCGG GCCTTGTACA CACCGCCCGT CACACCATGG
Haemophilus influenzae   ACGTTCCCGG GCNTTGTACA CACCGCCCGT CACACCATGG
Pseudomonas aeruginosa   ACGTTCCCGG GCCTTGTACA CACCGCCCGT CACACCATGG
Clostridium pefringens   ACGTTCCCNG GTCTTGTACA CACCGCNCGT CACACCATGA
```

ANNEX III-continued

ANNEX III
Selection of Universal Probes by Alignment of the Sequences of Bacterial 16S and 23S Ribosomal RNA Genes

| | |
|---|---|
| *Mycoplasma hominis* | ACGTTCTCGG GTCTTGTACA CACCGCCCGT CACACCATGG |
| *Helicobacter pylori* | ACGTTCCCGG GTCTTGTACT CACCGCCCGT CACACCATGG |
| *Mycoplasma pneumoniae* | ACGTTCTCGG GTCTTGTACA CACCGCCCGT CAAACTATGA |

Reverse strand of
SEQ ID NO: 125            TCG TAGTCCGGAT TGGAGTCTGC AACTC
                   1361                                    1400

| | |
|---|---|
| *Escherichia coli* | AAGTGCGTCG TAGTCCGGAT TGGAGTCTGC AACTCGACTC |
| *Neiserria ghonorrhoeae* | AAACCGATCG TAGTCCGGAT TGCACTCTGC AACTCGAGTG |
| *Pseudomonas cepacia* | AAACCGATCG TAGTCCGGAT TGCACTCTGC AACTCGAGTG |
| *Serratia marcescens* | AAGTATGTCG TAGTCCGGAT TGGAGTCTGC AACTCGACTC |
| *Proteus vulgaris* | AAGTCTGTCG TAGTCCGGAT TGGAGTCTGC AACTCGACTC |
| *Haemophilus influenzae* | AAGTACGTCT AAGTCCGGAT TGGAGTCTGC AACTCGACTC |
| *Pseudomonas aeruginosa* | AAACCGATCG TAGTCCGGAT CGCAGTCTGC AACTCGACTG |
| *Clostridium pefringens* | AAACCAGTCT CAGTTCGGAT TGTAGGCTGA AACTCGCCTA |
| *Mycoplasma hominis* | AAGCCGATCT CAGTTCGGAT TGGAGTCTGC AATTCGACTC |
| *Helicobacter pylori* | ACACC..TCT CAGTTCGGAT TGTAGGCTGC AACTCGCCTG |
| *Mycoplasma pneumoniae* | AAGTTGGTCT CAGTTCGGAT TGAGGGCTGC AATTCGTCTT |

Reverse strand of
SEQ ID NO: 128
                    481                                            530

| | |
|---|---|
| *Lactobacillus lactis* | AAACACAGCT CTCTGCTAAA CCGCAAGGTG ATGTATAGGG GGTGACGCCT |
| *Escherichia coli* | AAACACAGCA CTGTGCAAAC ACGAAAGTGG ACGTATACGG TGTGACGCCT |
| *Pseudomonas aeruginosa* | AAACACAGCA CTCTGCAAAC ACGAAAGTGG ACGTATAGGG TGTGACGCCT |
| *Pseudomonas cepacia* | AAACACAGCA CTCTGCAAAC ACGAAAGTGG ACGTATAAGG TGTGACGCCT |
| *Bacillus stearothermophilus* | AAACACAGGT CTCTGCGAAG TCGTAAGGCG ACGTATAGGG GCTGACACCT |
| *Micrococcus luteus* | AAACACAGGT CCATGCGAAG TCGTAAGACG ATGTATATGG ACTGACTCCT |

SEQ ID NO: 129            GGGGGGACC ATCCTCCAAG GCTAAATAC
                   1991                                    2040

| | |
|---|---|
| *Escherichia coli* | TGTCTGAATG TGGGGGGACC ATCCTCCAAG GATAAATACT CCTGACTGAC |
| *Pseudomonas aeruginosa* | TGTCTGAACA TGGGGGGACC ATCCTCCAAG GCTAAATACT ACTGACTGAC |
| *Pseudomonas cepacia* | TGTCTGAAGA TGGGGGGACC ATCCTCCAAG GCTAAATACT CGTGATCGAC |
| *Lactobacillus lactis* | AGTTTGAATC GCCCAGGACC ATCTCCCAAC CCTAAATACT CCTTAGTGAC |
| *Micrococcus luteus* | CGTGTGAATC TGCCAGGACC ACCTGGTAAG CCTGAATACT ACCTGTTGAC |

Reverse strand of
SEQ ID NO: 130            AACACAGCA CTCTGCAAAC ACGAAAGTGG ACG
                   1981                                    2030

| | |
|---|---|
| *Pseudomonas aeruginosa* | TGTTTATTAA AAACACAGCA CTCTGCAAAC ACGAAAGTGG ACGTATAGGG |
| *Escherichia coli* | TGTTTATTAA AAACACAGCA CTGTGCAAAC ACGAAAGTGG ACGTATACGG |
| *Bacillus stearothermophilus* | TGTTTAATAA AAACACAGCA CTCTGCAAAC ACGAAAGTGG ACGTATAGGG |
| *Lactobacillus lactis* | TGTTTATCAA AAACACAGCT CTCTGCTAAA CCACAAGGTG ATGTATAGGG |
| *Micrococcus luteus* | TGTTTATCAA AAACACAGGT CCATGCGAAG TCGTAAGACG ATGTATATGG |

SEQ ID NO: 126            GGAGGAA GGTGGGGATG ACG
Reverse strand of

SEQ ID NO: 127                                                      CA CACCGCCCGT CACACCAT

| | |
|---|---|
| *Escherichia coli* | ACTGGAGGAA GGTGGGGATG ACGTCAAGTC...GCCTTGTACA CACCGCCCGT CACACCATGG |
| *Neiserria ghonorrhoeae* | GCCGGAGGAA GGTGGGGATG ACGTCAAGTC...NNCTTGTACA CACCGCCCGT CACACCATGG |
| *Pseudomonas cepacia* | ACCGGAGGAA GGTNGGGATG ACGTCAAGTC...GTCTTGTACA CACNGCCCGT CACACCATGG |
| *Serratia marcescens* | ACTGGAGGAA GGTGGGGATG ACGTCAAGTC...GCCTTGTACA CACCGCCCGT CACACCATGG |
| *Proteus vulgaris* | ACCGGAGGAA GGTGGGGATG ACGTTAAGTC...GCCTTGTACA CACCGCCCGT CACACCATGG |
| *Haemophilus influenzae* | ACTGGAGGAA GGTNGGGATG ACGTCAAGTC...GCNTTGTACA CACCGCCCGT CACACCATGG |
| *Legionella pneumophila* | ACCGGAGGAA GGCGGGGATG ACGTCAAGTC...GCCTTGTACA CACCGCCCGT CACACCATGG |
| *Pseudomonas aeruginosa* | ACCGGAGGAA GGTGGGGATG ACGTCAAGTC...GCCTTGTACA CACCGCCCGT CACACCATGG |
| *Clostridium pefringens* | CCAGGAGGAA GGTGGGGATG ACGTNNAATC...GTCTTGTACA CACCGCNCGT CACACCATGA |
| *Mycoplasma hominis* | CTGGGAGGAA GGTGGGGATG ACGTCAAATC...GTCTTGTACA CACCGCCCGT CACACCATGG |
| *Helicobacter pylori* | GGAGGAGGAA GGTGGGGACG ACGTCAAGTC...GTCTTGTACT CACCGCCCGT CACACCATGG |
| *Mycoplasma pneumoniae* | ATTGGAGGAA GGAAGGGATG ACGTCAAATC...GTCTTGTACA CACCGCCCGT CAAACTATGA |

What is claimed is:

1. A method of simultaneously assaying for the presence and identity of a plurality of target bacterial species selected from the group consisting of *Klebsiella pneumoniae, Pseudomonas aeruginosa, Proteus mirabilis, Streptococcus pneumoniae, Staphylococcus aureus, Staphylococcus epidermidis, Enterococcus faecalis, Staphylococcus saprophyticus, Streptococcus pyogenes, Haemophilus influenzae,* and *Moraxella catarrhalis*, and at least one target bacterial antibiotic resistance gene selected from the group consisting of $bla_{tem}$, $bla_{rob}$, $bla_{shv}$, aadB, aacC1, aacC2, aacC3, aacA4, mecA, vanA, vanH, vanX, satA, aacA-aphD, vat, vga, msrA, sul, and int, by performing an assay comprising:

simultaneously contacting a sample with a set of amplification primers comprising a plurality of primer pairs, said plurality of primer pairs comprising:

a plurality of species-specific primer pairs, wherein each species-specific primer pair hybridizes in said assay to a target nucleic acid sequence of only one of said target bacterial species, and wherein the plurality of species specific primer pairs collectively hybridize to a plurality of the target bacterial species, and wherein said plurality of species-specific primer pairs comprise at least a first, second and third primer pair that hybridize in the assay solely to a first, second, and third target bacterial species, respectively; and one or more antibiotic resistance gene primer pairs, wherein said one or more antibiotic resistance gene primer pairs hybridizes in said assay to a target nucleic acid from said antibiotic resistance gene, and wherein the plurality of primer pairs and the one or more antibiotic resistance gene primer pairs are chosen to allow amplification under a single amplification protocol;

amplifying target nucleic acids from the sample under the single amplification protocol; and determining the presence or amount of target nucleic acids from the first, second and third target bacterial species, wherein at least one target nucleic acid is selected from the group consisting of: SEQ ID NO. 37 and a complementary sequence thereof, for determining the presence or amount of *Staphylococcus aureus* and detecting the presence and/or amount of amplified product(s) as an indication of the presence or amount of said target bacterial species and bacterial antibiotic resistance genes in the sample.

2. The method claim 1, wherein the method is performed directly on a sample obtained from human patients, animals, environment or food.

3. The method claim 1, wherein the method is performed directly on a sample consisting of one or more bacterial colonies.

4. The method of claim 1, comprising amplifying said target bacterial nucleic acids by multiplex PCR.

5. The method of claim 4, comprising performing, for each amplification cycle, an annealing step of only one second at 55° C. and a denaturation step of only one second at 95° C. without any time specifically allowed to an elongation step.

6. The method of claim 1, wherein the detecting step comprises hybridizing said target region and/or amplified target region with a probe.

7. The method of claim 1, wherein said plurality of primer pairs comprises at least one pair of primers selected from:
SEQ ID NO: 149 and SEQ ID NO: 150; SEQ ID NO: 149 and SEQ ID NO: 151; and SEQ ID NO: 152 and SEQ ID NO: 153; for the detection of *Staphylococcus aureus*.

8. The method of claim 1, wherein each of the primers of said at least one antibiotic resistance gene primer pair has at least twelve nucleotides in length capable of hybridizing with any one of the nucleotide sequences of:
SEQ ID NO. 169 or a sequence complementary thereto, for the detection of a bacterial resistance to β-lactam antibiotics mediated by the bacterial antibiotic resistance gene mecA;
SEQ ID NO. 170 or a sequence complementary thereto, for the detection of a bacterial resistance to vancomycin mediated by the bacterial antibiotic resistance genes vanH, vanA and vanX;
SEQ ID NO. 173 or a sequence complementary thereto, for the detection of a bacterial resistance to streptogramin A mediated by the bacterial antibiotic resistance gene satA;
SEQ ID NO. 174 or a sequence complementary thereto, for the detection of a bacterial resistance to aminoglycoside antibiotics mediated by the bacterial antibiotic resistance gene aacA-aphD;
SEQ ID NO. 175 or a sequence complementary thereto, for the detection of a bacterial resistance to virginiamycin mediated by the bacterial antibiotic resistance gene vat;
SEQ ID NO. 176 or a sequence complementary thereto, for the detection of a bacterial resistance to virginiamycin mediated by the bacterial antibiotic resistance gene vga;
SEQ ID NO. 177 or a sequence complementary thereto; for the detection of a bacterial resistance to erythromycin mediated by the bacterial antibiotic resistance gene msrA.

9. The method of claim 1, further comprising contacting said sample with a universal probe for detecting any bacterial species, wherein said probe comprises at least one single stranded nucleic acid comprising a nucleotide sequence having at least twelve nucleotides in length and is capable of hybridizing with any bacterial species and with at least one of SEQ ID NO: 122, SEQ ID NO: 123, SEQ ID NO: 124, SEQ ID NO: 125, SEQ ID NO: 128, SEQ ID NO: 129, SEQ ID NO: 130 and a sequence complementary thereto.

10. The method of claim 9, further comprising contacting said sample with universal primers, wherein said universal primers comprise at least one single stranded nucleic acid, wherein its nucleotide sequence has at least twelve nucleotides in length capable of hybridizing with any bacterial species and with at least one of SEQ ID NO: 126 and SEQ ID NO: 127 and a sequence complementary thereto.

11. The method of claim 1, wherein the at least one antibiotic resistance gene comprises mecA.

12. The method of claim 11, wherein the plurality of amplification primers comprises a primer that has at least twelve nucleotides in length capable of hybridizing with the nucleotide sequence of SEQ ID NO: 169.

13. A method for simultaneously assaying for the presence and identity of *S. aureus* and at least one additional target bacterial species and at least one antibiotic resistance gene, by performing an assay comprising:
simultaneously contacting a sample with a set of amplification primers comprising a plurality of primer pairs, wherein the plurality of primer pairs allows amplification under a single amplification protocol, said plurality of primer pairs comprising:
a primer pair that hybridizes to a target nucleic acid sequence of only *Staphylococcus aureus*;
at least one additional species-specific primer pair that hybridizes to target nucleic acids of only one target bacterial species selected from the group consisting of *Klebsiella pneumoniae, Pseudomonas aeuroginosa, Proteus mirabilis, Streptococcus pneumoniae, Staphylococcus epidermidis, Enterococcus faecalis, Staphylococcus saprophyticus, Streptococcus pyogenes, Haemophilus influenzae*, and *Moraxella catarrhalis*; and
at least one primer pair that hybridizes only to target nucleic acids of one bacterial antibiotic resistance gene selected from the group consisting of $bla_{tem}$, $bla_{rob}$, $bla_{shv}$, aadB, aacC1, aacC2, aacC3, aacA4, mecA, vanA, vanH, vanX, satA, aacA-aphD, vat, vga, msrA, sul, and int,
amplifying target nucleic acids from the sample under the single amplification protocol; and
detecting the presence or amount of amplified product(s) as an indication of the presence or amount of *Staphylococcus aureus*, the at least one additional target bacterial species, and the at least one bacterial antibiotic resistance gene in the sample, wherein said *Staphylococcus aureus* target nucleic acid is selected from the group consisting of SEQ ID NO:37 and a complementary sequence thereof.

14. The method of claim 13, wherein the at least one antibiotic resistance gene comprises mecA.

15. The method of claim 14, wherein the plurality of amplification primers comprises a primer that has at least twelve nucleotides in length capable of hybridizing with the nucleotide sequence of SEQ ID NO: 169.

16. The method of claim 13, wherein each of the primers of said at least one antibiotic resistance gene primer pair has at least twelve nucleotides in length capable of hybridizing with any one of the nucleotide sequences of:
SEQ ID NO. 169 or a sequence complementary thereto, for the detection of a bacterial resistance to β-lactam antibiotics mediated by the bacterial antibiotic resistance gene mecA;
SEQ ID NO. 170 or a sequence complementary thereto, for the detection of a bacterial resistance to vancomycin mediated by the bacterial antibiotic resistance genes vanH, vanA and vanX;
SEQ ID NO. 173 or a sequence complementary thereto, for the detection of a bacterial resistance to streptogramin A mediated by the bacterial antibiotic resistance gene satA;
SEQ ID NO. 174 or a sequence complementary thereto, for the detection of a bacterial resistance to aminoglycoside antibiotics mediated by the bacterial antibiotic resistance gene aacA-aphD;

SEQ ID NO. 175 or a sequence complementary thereto, for the detection of a bacterial resistance to virginiamycin mediated by the bacterial antibiotic resistance gene vat;

SEQ ID NO. 176 or a sequence complementary thereto, for the detection of a bacterial resistance to virginiamycin mediated by the bacterial antibiotic resistance gene vga;

SEQ ID NO. 177 or a sequence complementary thereto; for the detection of a bacterial resistance to erythromycin mediated by the bacterial antibiotic resistance gene msrA.

* * * * *